(12) United States Patent
Schofield et al.

(10) Patent No.: US 8,927,244 B2
(45) Date of Patent: Jan. 6, 2015

(54) ORGANOPHOSPHORUS HYDROLASE

(75) Inventors: David Alexander Schofield, Hollywood, SC (US); Augustine Anthony Dinovo, Charleston, SC (US)

(73) Assignee: Guild Associates, Inc., Dublin, OH (US)

( * ) Notice: Subject to any disclaimer, the term of this patent is extended or adjusted under 35 U.S.C. 154(b) by 1628 days.

(21) Appl. No.: 12/241,574

(22) Filed: Sep. 30, 2008

(65) Prior Publication Data

US 2012/0135497 A1 May 31, 2012

Related U.S. Application Data

(60) Provisional application No. 60/976,602, filed on Oct. 1, 2007.

(51) Int. Cl.
| | | |
|---|---|---|
| *C12N 9/00* | (2006.01) | |
| *C07K 14/00* | (2006.01) | |
| *C12Q 1/34* | (2006.01) | |
| *C12Q 1/02* | (2006.01) | |
| *G01N 33/84* | (2006.01) | |

(52) U.S. Cl.
CPC ............... *C12Q 1/025* (2013.01); *G01N 33/84* (2013.01); *G01N 2333/39* (2013.01)
USPC .............................. 435/183; 435/18; 530/350

(58) Field of Classification Search
None
See application file for complete search history.

(56) References Cited

FOREIGN PATENT DOCUMENTS

| | | | | |
|---|---|---|---|---|
| EP | 510907 | 4/1992 | | |
| WO | WO99/27351 | 6/1999 | ............. | G01N 21/76 |
| WO | WO 99/53037 | 10/1999 | ............. | C12N 9/00 |
| WO | WO 00/65081 | 11/2000 | ............. | C12Q 1/00 |
| WO | WO02/092803 | 11/2002 | ............. | C12N 9/14 |
| WO | 2004/027020 | 4/2004 | | |
| WO | WO2005/069738 | 8/2005 | | |
| WO | 2006/060051 | 6/2006 | | |
| WO | WO 2007/145661 | 12/2007 | ............. | C12Q 1/68 |
| WO | 2008/018854 | 2/2008 | | |
| WO | WO2009/082525 | 7/2009 | ............. | C12Q 1/42 |

OTHER PUBLICATIONS

European Office Action; Application No. 08 863 866.3-2401; pp. 7, Jun. 1, 2011.
International Preliminary report on Patentability and Written Opinion; Application No. PCT/US2008/078256; pp. 12, Apr. 15, 2010.
International Search Report and Written Opinion; International Application No. PCT/US2008/050378; pp. 17, Jan. 14, 2009.
Blanquet et al.; "The 'Biodrug' Concept: An Innovative Approach to Therapy"; Trends in Biotechnology; vol. 19, No. 10; pp. 393-400, Oct. 2001.
Yoong et al.; "PlyPH, a Bacteriolytic Enzyme With a Broad pH Range of Activity and Lytic Action Against *Bacillus anthracis*"; Journal of Bacteriology, vol. 188, No. 7; pp. 2711-2714, Apr. 2006.
Takahashi-Ando et al.; "Efficient Decontamination of Zearalenone, the Mycotoxin of Cereal Pathogen, by Transgenic Yeasts Through the Expression of a Sythetic Lactonohydrolase Gene"; Applied Microbiol Biotechnology; vol. 67; pp. 838-844, 2005.
Stuart; "Degradation of Biological Weapons Agents in the Environment: Implications for Terrorism Response"; Environ. Sci. Technol., vol. 39, pp. 2736-2743, 2005.
Fischetti; "Bacteriophage Lytic Enzymes: Novel Anti-Infectives"; Trends in Microbilogy, vol. 13, No. 10; pp. 491-496, Oct. 2005.
Borysowski et al.; "Bacteriophage Endolysins as a Novel Class of Antibacterial Agents"; Society for Experimental biology and Medicine, vol. 231; pp. 366-377, 2006.
Loessner; "Bacteriophage Endolysins—Current State of Research and Applications"; Current Opinion in Microbiology, vol. 8; pp. 480-487, 2005.
Schuch et al.; "A Bacteriolytic Agent That Detects and Kills *Bacillus anthracis*"; Nature, vol. 418; pp. 884-889, Aug. 22, 2002.
European Office Action; Application No. 08 795 774.2-1212; pp. 7, Apr. 22, 2010.
Erickson et al.; "*Bacillus anthracis*: Current Knowledge in Relation to Contamination of Food"; XP008099902; Journal of Food Protection; vol. 66, No. 4; pp. 691-699, 2003.
European Office Action; Application No. 06 851 299.5-2402; pp. 5, Jan. 15, 2010.
Schofield et al.; "Development of a yeast biosensor-biocatalyst for the detection and biodegradation of the organophosphate paraoxon"; Appl Microbiol Biotechnol, vol. 76; pp. 12, 2007.
Database Gene sequence; "Flavobacterium Opd Polypeptide"; XP002536209; retrieved from EBI accenssion No. GSP:ABB82802; pp. 2, Jul. 9, 2009.
Takahashi et al.; "Multiple Reporter Gene Assays for the Assessment and Estimation of Chemical Toxicity"; Environmental Sciences, vol. 11, No. 5; pp. 269-282, 2004.
Invitation to Pay Additional Fees and, Where Applicable, Protest Fee; PCT/US2008/078256; pp. 7, Aug. 10, 2009.
Biran et al., "Online and in situ Monitoring of Environmental Pollutants: Electrochemical Biosensing of Cadmium", Environmental Microbiology, vol. 3, No. 2, pp. 285-290, 2000.
Kitagawa et al., "Effects of the Pesticide Thiuram: Genome-Wide Screening of Indicator Genes by Yeast DNA Microarray", Environmental Science and Technology, vol. 36, No. 18, pp. 3908-3915, Sep. 15, 2002.
International Search Report and Written Opinion for International Application No. PCT/US2008/078256, mailing date Nov. 11, 2009, 21 pages.

(Continued)

*Primary Examiner* — Michele K Joike
(74) *Attorney, Agent, or Firm* — Baker Botts L.L.P.

(57) ABSTRACT

The present disclosure provides methods, devices, systems and compositions for detecting and/or modifying chemical agents. In some embodiments, a biosensor may be configured to detect a chemical agent, modify that agent to a form with reduced toxicity, and/or detect the modified form of the chemical agent. The present disclosure also relates, in some embodiments, to variant organophosphorus hydrolase having one or more desirable amino acid substitutions.

56 Claims, 23 Drawing Sheets

(56) References Cited

OTHER PUBLICATIONS

Preliminary Report on Patentability PCT/US2006/045761, 7 pages, Jun. 12, 2008.
European Office Action; Application No. 06 851 299.5-2402; pp. 6, Jan. 12, 2009.
Extended European Search Report; Application No. 11189801.1-2401; pp. 9, Mar. 19, 2012.
Gopal et al.; "Mutagenesis of Organophosphorus Hydrolase to Enhance Hydrosis of the Nerve Agent VX"; Biochemical and Biophysical Research Communications; 279; pp. 516-519, 2000.
Di Sioudi et al.; "Rational design of organophosphorus hydrolase for altered substrate specificities"; Chemico-Biological Interactions; pp. 211-223, 1999.
Cho et al.; "Functional Analysis of organopphosphorus hydrolase variants with high degradation activity towards organophosphate pesticides"; Protein Engineering, Design & Selection, vol. 19, No. 3; pp. 99-105, 2006.
Roodvelt et al.; "Directed evolution of phosphotriesterase from *Pseudomonas diminuta* for heterologous expression in *Escherichia coli* results in stabilization of the metal-free state"; Protein Engineering, Design & Selection, vol. 18, No. 1; pp. 51-58, 2005.
Schofield et al.; Generation of a mutagenized organophosphorus hydrolase for the biodegradation of the organophosphate pesticides malathion and demeton-S; Journal of Applied Microbiology , vol. 109; pp. 548-557, 2010.
Dave et al.; "Characterization of Organophosphorus Hydrolases and the Genetic Manipulation of the Phosphotriesterase From *Psuedomonas diminuta*"; Chem.-Biol. Interactions, No. 87; pp. 55-68, 1993.
Zheng et al.; "Secondary Structure of Organophosphorus Hydrolase in Solution and in Langmuir-Blodgett Film Studied by Circular Dichroism Spectroscopy"; J. Phys. Chem. B, No. 108; pp. 17238-17242, 2004.
Charles David Armstrong; "Elucidating the Chemical and Thermal Unfolding Profiles of Organophosporus Hydrolase and Increasing Its Operations Stability"; Armstrong Dissertation, Texas A&M University; pp. 180, 2007.
European Office Action; Application No. 11 189 801.1-2401; pp. 4, Jan. 18, 2013.

Yeast codon-optimized opd sequence
ATGACTATGATAACTAACAGCGGCGACAGGATAAACACAGTACGAGGACCAATTACTATATCCGAAGCAGGATT
CACACTGACCCATGAACATATTTGTGGATCGTCAGCAGGGTTTTTAAGAGCTTGGCCCGAGTTCTTTGGCTCAA
GAAAGGCGTTAGCAGAGAAAGCCGTAAGGGGATTGCGAAGAGCTAGAGCCGCCGGTGTTAGAACCATTGTTGAC
GTTTCTACATTCGATATCGGAAGGGACGTTTCTCTACTAGCGGAAGTCTCCAGGGCTGCGGACGTGCATATTGT
TGCTGCCACTGGTCTATGGTTTGATCCTCCATTGTCAATGAGGTTGAGATCAGTGGAGGAACTTACGCAATTTT
TCTTGCGTGAGATTCAATACGGTATAGAAGACACAGGTATTAGAGCAGGTATCATCAAAGTAGCTACAACCGGG
AAGGCTACTCCTTTTCAAGAATTAGTTCTAAAAGCCGCAGCCAGGGCATCCCTTGCTACCGGTGTTCCTGTGAC
AACTCATACGGCTGCCTCTCAGCGTGATGGCGAACAACAAGCTGCTATCTTTGAAAGCGAAGGCTTGTCGCCAA
GTAGAGTGTGTATTGGACATTCTGATGATACTGATGACTTGTCTTACTTGACCGCATTAGCTGCCAGAGGTTAT
TTAATAGGTTTGGACCACATTCCCCACAGTGCAATTGGTTTGGAGGATAATGCATCGGCTAGTGCTCTGTTAGG
GATTCGCAGTTGGCAGACTAGGGCTCTGCTAATAAAGGCATTAATTGACCAAGGGTATATGAAACAGATCCTTG
TTTCAAATGATTGGCTTTTCGGTTTTTCATCTTATGTAACTAATATCATGGATGTAATGGATCGCGTCAATCCA
GACGGTATGGCTTTCATTCCGTTACGTGTCATACCGTTTCTGCGTGAAAAAGGCGTCCCCCAGGAAACGTTGGC
AGGTATTACTGTTACAAACCCAGCCAGATTTTTAAGCCCTACGCTCAGAGCCTCCTGA

FIG.4A

Yeast codon-optimized DsRed express sequence
ATGGCTAGCTCCGAGGACGTTATAAAAGAGTTCATGAGATTTAAAGTAAGAATGGAGGGCAGTGTTAACGGTCA
CGAATTTGAAATAGAAGGGGAAGGCGAGGGTAGACCATATGAAGGCACTCAAACAGCCAAACTGAAGGTTACTA
AGGGAGGTCCATTGCCTTTTGCATGGGATATTTTGTCCCCTCAATTTCAATACGGGAGTAAAGTGTATGTGAAA
CACCCCGCTGACATCCCTGATTATAAGAAACTCTCTTTTCCAGAAGGATTCAAGTGGGAAAGAGTCATGAACTT
CGAAGACGGAGGTGTAGTAACGGTAACCCAGGATTCTTCTCTTCAAGATGGTAGCTTTATCTATAAGGTTAAAT
TCATTGGAGTCAATTTTCCATCAGACGGTCCCGTTATGCAGAAGAAAACTATGGGATGGGAAGCCTCGACAGAG
AGGTTGTATCCGCGTGATGGGGTGTTGAAAGGCGAAATTCATAAGGCTTTAAAGTTAAAAGACGGTGGTCATTA
TTTAGTTGAATTCAAATCTATTTACATGGCGAAAAAGCCTGTCCAATTACCAGGTTACTACTACGTGGATTCAA
AACTAGATATTACCTCACATAATGAGGATTATACAATCGTCGAACAATACGAACGAGCAGAAGGCAGGCATCAT
CTTTTTCTATAG

FIG.4B

YGR035C-FI-YeGFP sequence gtcgaCAGAGTTTACTTGCACTACCACAATTTAGATCAAGTAATCGTGGGATTCAGCGTGGGGGCACTGACTGG
ATCACTTTATTTTTTTATAGTTGGCATCATAAGAGAGCTTGGTTTAATCAATTGGTTTTTAAAACTACGTATTG
TCAGATTATTTTACATGACAGATTCTTACAATCTGGCGCCTTTGACATTGAAAGAGAATTACGAGGCGTATTGG
AAAAGAATAAATCAGCGATCTTTCAATGATAAATCCAAAAGGGATTAGGTTGAACATTTCATTTTTCTTATTTT
TTCATCTATTTTAGCGAGGCGATCTTGAGCGTTTGTGTAACTGGATAAAACTTGGCAAGCTGGAGTAGTCCTTA
TTTCTCATAAAGAAAGCCGAAAGCCTGCTCTCCTACAGTTATTAATTAAGAACGCTCGTTTTAAACAGTTACTG
TGTAAAGCGACGGTAATCGAAAAAGTATGTGACATCGTGCAAAAGAAGATAATCAAAACCATGCAGAACGTAGA
ATAAATGTGAGTTCTATCACTTGCGGAGATAATACCCTCTGACGCCGCGGGGCCGATTGTTCCACGGAGGGAAA
GAATCGGCCCTCGGGTTTTACGAGAGCGCCGCGGGTGAACTCACTTTTTTCTCGAGAAGAAGTTTCCTACGGCA
GAATAAGACCCTTTTCCACGGATAATCAGCGGAGCTTCTGGACATAATAGATGGTTTGTGAAAAAGCTTAAGGA
AAGCCGCGGATTTAGCATGTCACCCACACTTAGATTACGAAAGCAAGGATTGCAGAAAAAAAGATGAGATACAG
TTTTGAGGGCAATATATAAAATATATAAATATAGCAACATTCCCTTCTCTCTGTTATGTCCACAATACTTCTAA
AAGTTGTAACATATATCTATACATAAAAACTTGTAACAAACATATAATTAAAACAACTAGTGACAAGACGGAAG
TTATAAGTTATCTTCTCTACAGAAACAATACGTAggatccattaaaATGTCTAAAGGTGAAGAATTATTCACTG
GTGTTGTCCCAATTTTGGTTGAATTAGATGGTGATGTTAATGGTCACAAATTTTCTGTCTCCGGTGAAGGTGAA
GGTGATGCTACTTACGGTAAATTGACCTTAAAATTTATTTGTACTACTGGTAAATTGCCAGTTCCATGGCCAAC
CTTAGTCACTACTTTCGGTTATGGTGTTCAATGTTTTGCGAGATACCCAGATCATATGAAACAACATGACTTTT
TCAAGTCTGCCATGCCAGAAGGTTATGTTCAAGAAAGAACTATTTTTTTCAAAGATGACGGTAACTACAAGACC
AGAGCTGAAGTCAAGTTTGAAGGTGATACCTTAGTTAATAGAATCGAATTAAAAGGTATTGATTTTAAAGAAGA
TGGTAACATTTTAGGTCACAAATTGGAATACAACTATAACTCTCACAATGTTTACATCATGGCTGACAAACAAA
AGAATGGTATCAAAGTTAACTTCAAAATTAGACACAACATTGAAGATGGTTCTGTTCAATTAGCTGACCATTAT
CAACAAAATACTCCAATTGGTGATGGTCCAGTCTTGTTACCAGACAACCATTACTTATCCACTCAATCTGCCTT
ATCCAAAGATCCAAACGAAAAGAGAGACCACATGGTCTTGTTAGAATTTGTTACTGCTGCTGGTATTACCCATG
GTATGGATGAATTGTACAAATAAactagt

FIG.15A pYLR346C-FI-YeGFP gtcgaCTTTCTTCCTTTTCTACTATCTTCTCTTTTATTATTATATTATATTATCAATAACCCTCATCTCTCTCT
CTCTCTCTCTCTCTCTCTCTCTCTCTCTCTCTCTCTCTCTCTCTCTCTCTCCTTTTTTTCTTCTTTTAGA
TTTTTTTGCTTTTGTTTAATTTCATTCCAGTTTCCCCCCCCCAATATTAATATTCGTTCCTAGAGCCTATCACA
CCTAATATTTCCCGTATACATTATAGTAAATACCTCAAGACACTTATGATAGATTTTTTTCCTTAACTCAAACC
TAATTAGCTCTATGCATAAAGAAAGTTTTGAATAAGGAAATCCGCATATTCAAATTATCAAACATGCACTTCAT
CTGCAAAACTTCCAAAAACTTTCTGCTCGTTAATAGTCAATGTATGGTAATGCGAATGAGCAGGTACCCCTTAT
TATAATGATTAATACTTACATCATAGTTAATAATCTTATCTCAGGGTACCCATAATTTCAACCATCCTTAGCTT
CCATTAAAAACACAATGAGTTGCGTTACTAGCGAAGCGGCTTATCTGTTAATTCTTGCTTGCAAACATCTTAGC
TGAAAGTGAAAAGGCACAGCCGCACCTGCTGAATGCTCAACGTTTGTAATAATCCGCCTATTTCCGCGGAATCA
ATAGGGCTCCTAGCAGGCCGCCATCAATTTTCAGCGTGCCGCATTAAAATTATATTACCAAGATTTCCATTTCC
GCGGCTGATTCCTATCAATATTAAGTAATCAATCTTTTCCTCGTGATTCTTTGTGATGCTCATTCACAGAGGAC
TAATTAAGACATGTAGCACAATATATTCATATAAAAGTTGGTGCAGTTAATGATTAATTGCATTGTTTTCCTTG
TTTCTTTCTGTTATACCTGTCGAATTAAACATAAAGTGTATATGAATTTTAAGGGGCACAAATAACAAAGGATT
ATTTATCACCTTTAATAggatccattaaaATGTCTAAAGGTGAAGAATTATTCACTGGTGTTGTCCCAATTTTG
GTTGAATTAGATGGTGATGTTAATGGTCACAAATTTTCTGTCTCCGGTGAAGGTGAAGGTGATGCTACTTACGG
TAAATTGACCTTAAAATTTATTTGTACTACTGGTAAATTGCCAGTTCCATGGCCAACCTTAGTCACTACTTTCG
GTTATGGTGTTCAATGTTTTGCgAGATACCCAGATCATATGAAACAACATGACTTTTTCAAGTCTGCCATGCCA
GAAGGTTATGTTCAAGAAAGAACTATTTTTTTTCAAAGATGACGGTAACTACAAGACCAGAGCTGAAGTCAAGTT
TGAAGGTGATACCTTAGTTAATAGAATCGAATTAAAAGGTATTGATTTTAAAGAAGATGGTAACATTTTAGGTC
ACAAATTGGAATACAACTATAACTCTCACAATGTTTACATCATGGCTGACAAACAAAAGAATGGTATCAAAGTT
AACTTCAAAATTAGACACAACATTGAAGATGGTTCTGTTCAATTAGCTGACCATTATCAACAAAATACTCCAAT
TGGTGATGGTCCAGTCTTGTTACCAGACAACCATTACTTATCCACTCAATCTGCCTTATCCAAAGATCCAAACG
AAAAGAGAGACCACATGGTCTTGTTAGAATTTGTTACTGCTGCTGGTATTACCCATGGTATGGATGAATTGTAC
AAATAAactagt

FIG.15B pYGR287C-FI-YDsRed gtcgacGGCTGTATGTTTATGATTGCTCGAATCACGTTTTTCTTGTTTTTTCGTCAAGAATTCCAGTCAAGTTT
TCCACCACCTTGACCCTTAAAGCATCGACTTTTGTGCTCTTGAATGTGTTTCTAAGAATACTTGTAAAGGACAC
CCTCTAATTTCGTGTGCACTTTTCACATATTATCAAGACAATCGTTCCTGTACTCAGATGCACTGTTACTGTAA
AGACTACTATACAACAAGCGAAAAATGATGTTCGAAAACCTTTATTTCTATTTTGAAAGGCATGTGTCTCGAGG
TCCTTGCTTTATTGTGGGTGGTCATGCCATTCTGTAAACCTTACGGTACTGCTCCGTCTATATCTTTGAGGTTG
TTATTTCCCCACAAATATGCGTTTCTAACCGAATATTCATTCAGTCGGACCGGACAATAGCTCTTAACTGCGTT
TACCGGAGTAAATATCGTAAGAATTTGCATGCGGTGAAATACAGGGAAAATAAGAAATTACACCCTAATACAAA
AAGAAAACTAAGTTTCACAATACGTAAGGATATTTTAGTGGGGAGAATATTTCGGAGAATAAAGTTTCCAACTC
CGCGGTGTGAACAACCGCTCAGCACGCAGCGTTATTCTCGAGAAAAGTGGCCCTGAAATAAGGAAATAAAGTTA
CTAATGTTTTTTCGCTGTACGATATCAAATGTGACGAAGTAGGCACCCCACGCTATAAATTGGCTACTAAAGTT
TATGTCAGTACTTGGGATCGTTGAAATACTCGGATAAATTATGTTCCTTATTTTTCATGGTTTTCGTCATACCA
CAGTTTACCCCAGAATGAGAAAGGATCTCCTTTTGAAATAAAAAGTACTTAAGGGCAATGATATTGAGTTGCTA
GACGTTTGGTTAGACGCCTGTTTTGAAATAAAAAAGCTGTCTCAAATTAATCGAGCAAGCACAGATCAAACAAG
ATACAAACAAAGCTTTTCAACGTAATATTTACTATCGgatccaaaagtATGGCTAGCTCCGAGGACGTTATAAA
AGAGTTCATGAGATTTAAAGTAAGAATGGAGGGCAGTGTTAACGGTCACGAATTTGAAATAGAAGGGGAAGGCG
AGGGTAGACCATATGAAGGCACTCAAACAGCCAAACTGAAGGTTACTAAGGGAGGTCCATTGCCTTTTGCATGG
GATATTTTGTCCCCTCAATTTCAATACGGGAGTAAAGTGTATGTGAAACACCCCGCTGACATCCCTGATTATAA
GAAACTCTCTTTTCCAGAAGGATTCAAGTGGGAAAGAGTCATGAACTTCGAAGACGGAGGTGTAGTAACGGTAA
CCCAGGATTCTTCTCTTAAGATGGTAGCTTTATCTATAAGGTTAAATTCATTGGAGTCAATTTTCCATCAGAC
GGTCCCGTTATGCAGAAGAAAACTATGGGATGGGAAGCCTCGACAGAGAGGTTGTATCCGCGTGATGGGGTGTT
GAAAGGCGAAATTCATAAGGCTTTAAAGTTAAAAGACGGTGGTCATTATTTAGTTGAATTCAAATCTATTTACA
TGGCGAAAAAGCCTGTCCAATTACCAGGTTACTACTACGTGGATTCAAAACTAGATATTACCTCACATAATGAG
GATTATACAATCGTCGAACAATACGAACGAGCAGAAGGCAGGCATCATCTTTTTCTATAGgcggccgc

FIG.18A pPOX1-FI-YDsRed gtcgacTTTCACTCAACCACCTCCAAAAAATAACAGGTTCATCTAAAGTAAAAGACTTTAACTTGCTCTTAGTT
TCCAAATTAAATATCTGCACGATAGTACCATTTGCTCTAACGGAAATAACCATCTGAGATGGATGCATGATAGC
AGAATCACCGCCCATATTCTTCCTTGTCACTTCATTGCCTTTGGCCAAATCCACGATTGCAACAGAGTTTGTAC
CGTCCTTTGTTTCTCTAACAGTGACGAAGTGGTCACTCTCGAAAGTAGTTGATCTGAAGTCAAGGAATTGAGGG
GAAATTCCTAAGGACATCAGATCGACCAATTCGGTAAATTCAATGGGTAGGTCACTCATTGGTTAGAACTTTCG
TGATAATTTATTTTTATAGTTGAATATCTTCTTTCTCTCTCAACTCTGATCCGGATTGTCGAGGTTTCAATAAG
TTACTCTGAACAACTAATCAAAATATCTCCTTATTTCTGTAGATTCCTTCAGTTCCACTTTTTACTTTTCTTAA
TTCTCTTTGTATTTATTCCTAGCGACGAAAAATGCGAGATCTCGACCAAAAAAAGGGGGTAGGGTAATAAAATT
AACCCTATTATTTTTTAACTTTAAAACCTATAATGTGCTAATATTTTATTATAAACCTCCTTTTTTTGCGTTCA
AACCCTGACACATTTTAAGCCCTATATTTACGGTATTAGTTGATTAAACTCCGAAGCGAAAGGAATTCGGTCAT
TAGCGGCTAATAGCCGTTGGGGTAAATCACCTACAAGCAAGTACACAAGAGAACGTTGGCGTTGTTAAGTCAAA
GCACTAATACATTGGGGCTTTAAGAGTGTTTATAAAGGTCTAACCTGTAAAAATTATTTAAACAACTTGAACAG
GCCTTAAAGTTTTCCTCATTCCGCTCATCATCACTAATATTGCTCTCCGTTTTTGAATACACACTTGACACTAA
TAAGTATCACAGAAAAAAAGAAAATATAATAAATTAGTATTGCGATggatccaaaagtATGGCTAGCTCCGAGG
ACGTTATAAAAGAGTTCATGAGATTTAAAGTAAGAATGGAGGGCAGTGTTAACGGTCACGAATTTGAAATAGAA
GGGGAAGGCGAGGGTAGACCATATGAAGGCACTCAAACAGCCAAACTGAAGGTTACTAAGGGAGGTCCATTGCC
TTTTGCATGGGATATTTTGTCCCCTCAATTTCAATACGGGAGTAAAGTGTATGTGAAACACCCCGCTGACATCC
CTGATTATAAGAAACTCTCTTTTCCAGAAGGATTCAAGTGGGAAAGAGTCATGAACTTCGAAGACGGAGGTGTA
GTAACGGTAACCCAGGATTCTTCTCTTCAAGATGGTAGCTTTATCTATAAGGTTAAATTCATTGGAGTCAATTT
TCCATCAGACGGTCCCGTTATGCAGAAGAAAACTATGGGATGGGAAGCCTCGACAGAGAGGTTGTATCCGCGTG
ATGGGGTGTTGAAAGGCGAAATTCATAAGGCTTTAAAGTTAAAAGACGGTGGTCATTATTTAGTTGAATTCAAA
TCTATTTACATGGCGAAAAAGCCTGTCCAATTACCAGGTTACTACTACGTGGATTCAAAACTAGATATTACCTC
ACATAATGAGGATTATACAATCGTCGAACAATACGAACGAGCAGAAGGCAGGCATCATCTTTTTCTATAGgcgg
ccgc

FIG.18B

Wild-type OPH (SEQ ID NO: 68)
MITNSGDRINTVRGPITISEAGFTLTHEHICGSSAGFLRAWPEFFGSRKALAEKAVR
GLRRARAAGVRTIVDVSTFDIGRDVSLLAEVSRAADVHIVAATGLWFDPPLSMRL
RSVEELTQFFLREIQYGIEDTGIRAGIIKVATTGKATPFQELVLKAAARASLATGVP
VTTHTAASQRDGEQQAAIFESEGLSPSRVCIGHSDDTDDLSYLTALAARGYLIGLD
HIPHSAIGLEDNASASALLGIRSWQTRALLIKALIDQGYMKQILVSNDWLFGFSSY
VTNIMDVMDRVNPDGMAFIPLRVIPFLREKGVPQETLAGITVTNPARFLSPTLRAS
Z I274N (A80V, K185R, D208G, I274N, R319S) (SEQ ID NO: 69)
MITNSGDRINTVRGPITISEAGFTLTHEHICGSSAGFLRAWPEFFGSRKALVEKAVR
GLRRARAAGVRTIVDVSTFDIGRDVSLLAEVSRAADVHIVAATGLWFDPPLSMRL
RSVEELTQFFLREIQYGIEDTGIRAGIIKVATTGKATPFQELVLRAAARASLATGVP
VTTHTAASQRGGEQQAAIFESEGLSPSRVCIGHSDDTDDLSYLTALAARGYLIGLD
HIPHSAIGLEDNASASALLGNRSWQTRALLIKALIDQGYMKQILVSNDWLFGFSSY
VTNIMDVMDSVNPDGMAFIPLRVIPFLREKGVPQETLAGITVTNPARFLSPTLRAS
Z H257W (A80V, K185R, D208G, H257W, I274N, R319S) (SEQ ID NO: 70)
MITNSGDRINTVRGPITISEAGFTLTHEHICGSSAGFLRAWPEFFGSRKALVEKAVR
GLRRARAAGVRTIVDVSTFDIGRDVSLLAEVSRAADVHIVAATGLWFDPPLSMRL
RSVEELTQFFLREIQYGIEDTGIRAGIIKVATTGKATPFQELVLRAAARASLATGVP
VTTHTAASQRGGEQQAAIFESEGLSPSRVCIGHSDDTDDLSYLTALAARGYLIGLD
HIPWSAIGLEDNASASALLGNRSWQTRALLIKALIDQGYMKQILVSNDWLFGFSS
YVTNIMDVMDSVNPDGMAFIPLRVIPFLREKGVPQETLAGITVTNPARFLSPTLRA
SZ F132D (A80V, F132D, K185R, D208G, H257W, I274N, R319S) (SEQ ID NO: 71)
MITNSGDRINTVRGPITISEAGFTLTHEHICGSSAGFLRAWPEFFGSRKALVEKAVR
GLRRARAAGVRTIVDVSTFDIGRDVSLLAEVSRAADVHIVAATGLWDDPPLSMRL
RSVEELTQFFLREIQYGIEDTGIRAGIIKVATTGKATPFQELVLRAAARASLATGVP
VTTHTAASQRGGEQQAAIFESEGLSPSRVCIGHSDDTDDLSYLTALAARGYLIGLD
HIPWSAIGLEDNASASALLGNRSWQTRALLIKALIDQGYMKQILVSNDWLFGFSS
YVTNIMDVMDSVNPDGMAFIPLRVIPFLREKGVPQETLAGITVTNPARFLSPTLRA
SZ F132C (A80V, F132C, K185R, D208G, H257W, I274N, R319S) (SEQ ID NO: 72)
MITNSGDRINTVRGPITISEAGFTLTHEHICGSSAGFLRAWPEFFGSRKALVEKAVR
GLRRARAAGVRTIVDVSTFDIGRDVSLLAEVSRAADVHIVAATGLWCDPPLSMRL
RSVEELTQFFLREIQYGIEDTGIRAGIIKVATTGKATPFQELVLRAAARASLATGVP
VTTHTAASQRGGEQQAAIFESEGLSPSRVCIGHSDDTDDLSYLTALAARGYLIGLD
HIPWSAIGLEDNASASALLGNRSWQTRALLIKALIDQGYMKQILVSNDWLFGFSS
YVTNIMDVMDSVNPDGMAFIPLRVIPFLREKGVPQETLAGITVTNPARFLSPTLRA
SZ

FIG.21A

I106V (A80V, I106V, F132D, K185R, D208G, H257W, I274N, R319S) (SEQ ID NO: 73)
MITNSGDRINTVRGPITISEAGFTLTHEHICGSSAGFLRAWPEFFGSRKALVEKAVR
GLRRARAAGVRTIVDVSTFDVGRDVSLLAEVSRAADVHIVAATGLWDDPPLSMR
LRSVEELTQFFLREIQYGIEDTGIRAGIIKVATTGKATPFQELVLRAAARASLATGV
PVTTHTAASQRGGEQQAAIFESEGLSPSRVCIGHSDDTDDLSYLTALAARGYLIGL
DHIPWSAIGLEDNASASALLGNRSWQTRALLIKALIDQGYMKQILVSNDWLFGFS
SYVTNIMDVMDSVNPDGMAFIPLRVIPFLREKGVPQETLAGITVTNPARFLSPTLR
ASZ

G60V (G60V, A80V, I106V, F132D, K185R, D208G, H257W, I274N, R319S) (SEQ ID NO: 74)
MITNSGDRINTVRGPITISEAGFTLTHEHICVSSAGFLRAWPEFFGSRKALVEKAVR
GLRRARAAGVRTIVDVSTFDVGRDVSLLAEVSRAADVHIVAATGLWDDPPLSMR
LRSVEELTQFFLREIQYGIEDTGIRAGIIKVATTGKATPFQELVLRAAARASLATGV
PVTTHTAASQRGGEQQAAIFESEGLSPSRVCIGHSDDTDDLSYLTALAARGYLIGL
DHIPWSAIGLEDNASASALLGNRSWQTRALLIKALIDQGYMKQILVSNDWLFGFS
SYVTNIMDVMDSVNPDGMAFIPLRVIPFLREKGVPQETLAGITVTNPARFLSPTLR
ASZ

F306V (G60V, A80V, I106V, F132D, K185R, D208G, H257W, I274N, F306V, R319S) (SEQ ID NO: 75)
MITNSGDRINTVRGPITISEAGFTLTHEHICVSSAGFLRAWPEFFGSRKALVEKAVR
GLRRARAAGVRTIVDVSTFDVGRDVSLLAEVSRAADVHIVAATGLWDDPPLSMR
LRSVEELTQFFLREIQYGIEDTGIRAGIIKVATTGKATPFQELVLRAAARASLATGV
PVTTHTAASQRGGEQQAAIFESEGLSPSRVCIGHSDDTDDLSYLTALAARGYLIGL
DHIPWSAIGLEDNASASALLGNRSWQTRALLIKALIDQGYMKQILVSNDWLFGV
SSYVTNIMDVMDSVNPDGMAFIPLRVIPFLREKGVPQETLAGITVTNPARFLSPTL
RASZ

S308L (A80V, I106V, F132D, K185R, D208G, H257W, I274N, S308L, R319S) (SEQ ID NO: 76)
MITNSGDRINTVRGPITISEAGFTLTHEHICGSSAGFLRAWPEFFGSRKALVEKAVR
GLRRARAAGVRTIVDVSTFDVGRDVSLLAEVSRAADVHIVAATGLWDDPPLSMR
LRSVEELTQFFLREIQYGIEDTGIRAGIIKVATTGKATPFQELVLRAAARASLATGV
PVTTHTAASQRGGEQQAAIFESEGLSPSRVCIGHSDDTDDLSYLTALAARGYLIGL
DHIPWSAIGLEDNASASALLGNRSWQTRALLIKALIDQGYMKQILVSNDWLFGFS
LYVTNIMDVMDSVNPDGMAFIPLRVIPFLREKGVPQETLAGITVTNPARFLSPTLR
ASZ

FIG. 21B

SEQUENCE LISTING

<160> NUMBER OF SEQ ID NOS: 95

<210> SEQ ID NO 1
<211> LENGTH: 1020
<212> TYPE: DNA
<213> ORGANISM: Artificial Sequence
<220> FEATURE:
<223> OTHER INFORMATION: Synthetic Yeast codon-optimized opd sequence

<400> SEQUENCE: 1

```
atgactatga taactaacag cggcgacagg ataaacacag tacgaggacc aattactata      60
tccgaagcag gattcacact gacccatgaa catatttgtg gatcgtcagc agggtttta     120
agagcttggc ccgagttctt tggctcaaga aaggcgttag cagagaaagc cgtaaggga     180
ttgcgaagag ctagagccgc cggtgttaga accattgttg acgtttctac attcgatatc    240
ggaagggacg tttctctact agcggaagtc tccagggctg cggacgtgca tattgttgct    300
gccactggtc tatggtttga tcctccattg tcaatgaggt tgagatcagt ggaggaactt    360
acgcaatttt tcttgcgtga gattcaatac ggtatagaag acacaggtat tagagcaggt    420
atcatcaaag tagctacaac cgggaaggct actcctttc aagaattagt tctaaaagcc     480
gcagccaggg catcccttgc taccggtgtt cctgtgacaa ctcatacggc tgcctctcag    540
cgtgatggcg acaacaagc tgctatcttt gaaagcgaag gcttgtcgcc aagtagagtg     600
tgtattggac attctgatga tactgatgac ttgtcttact tgaccgcatt agctgccaga    660
ggttatttaa taggtttgga ccacattccc cacagtgcaa ttggtttgga ggataatgca    720
tcggctagtg ctctgttagg gattcgcagt tggcagacta gggctctgct aataaaggca    780
ttaattgacc aagggtatat gaaacagatc cttgtttcaa atgattggct tttcggtttt    840
tcatcttatg taactaatat catggatgta atggatcgcg tcaatccaga cggtatggct    900
ttcattccgt tacgtgtcat accgtttctg cgtgaaaaag cgtccccca ggaaacgttg     960
gcaggtatta ctgttacaaa cccagccaga tttttaagcc ctacgctcag agcctcctga   1020
```

<210> SEQ ID NO 2
<211> LENGTH: 678
<212> TYPE: DNA
<213> ORGANISM: Artificial Sequence
<220> FEATURE:
<223> OTHER INFORMATION: Synthetic Yeast codon-optimized DsRed express
      sequence

<400> SEQUENCE: 2

```
atggctagct ccgaggacgt tataaaagag ttcatgagat ttaaagtaag aatggagggc      60
agtgttaacg gtcacgaatt tgaaatagaa ggggaaggcg agggtagacc atatgaaggc    120
actcaaacag ccaaactgaa ggttactaag ggaggtccat gccttttgc atgggatatt     180
ttgtcccctc aatttcaata cgggagtaaa gtgtatgtga acacccgc tgacatccct      240
gattataaga aactctcttt tccagaagga ttcaagtggg aaagagtcat gaacttcgaa    300
gacggaggtg tagtaacggt aacccaggat tcttctcttc aagatggtag ctttatctat    360
aaggttaaat tcattggagt caattttcca tcagacggtc ccgttatgca agagaaaact    420
atgggatggg aagcctcgac agagaggttg tatccgcgtg atggggtgtt gaaaggcgaa    480
attcataagg ctttaaagtt aaaagacggt ggtcattatt tagttgaatt caaatctatt    540
tacatggcga aaaagcctgt ccaattacca ggttactact acgtggattc aaaactagat    600
attacctcac ataatgagga ttatacaatc gtcgaacaat acgaacgagc agaaggcagg    660
```

```
catcatcttt ttctatag                                                      678
```

```
<210> SEQ ID NO 3
<211> LENGTH: 1731
<212> TYPE: DNA
<213> ORGANISM: Artificial Sequence
<220> FEATURE:
<223> OTHER INFORMATION: Synthetic nucleotide derived from E. coli and
      S. cerevisiae

<400> SEQUENCE: 3
gtcgacagag tttacttgca ctaccacaat ttagatcaag taatcgtggg attcagcgtg     60
ggggcactga ctggatcact ttattttttt atagttggca tcataagaga gcttggttta    120
atcaattggt ttttaaaact acgtattgtc agattatttt acatgacaga ttcttacaat    180
ctggcgcctt tgacattgaa agagaattac gaggcgtatt ggaaaagaat aaatcagcga    240
tctttcaatg ataaatccaa aagggattag gttgaacatt tcattttttct tatttttttca   300
tctattttag cgaggcgatc ttgagcgttt gtgtaactgg ataaaacttg gcaagctgga    360
gtagtcctta tttctcataa agaaagccga aagcctgctc tcctacagtt attaattaag    420
aacgctcgtt ttaaacagtt actgtgtaaa gcgacggtaa tcgaaaaagt atgtgacatc    480
gtgcaaaaga agataatcaa aaccatgcag aacgtagaat aaatgtgagt tctatcactt    540
gcggagataa taccctctga cgccgcgggg ccgattgttc cacggaggga agaatcggc     600
cctcgggttt tacgagagcg ccgcgggtga actcactttt ttctcgagaa gaagtttcct    660
acggcagaat aagacccttt tccacggata atcagcggag cttctggaca taatagatgg    720
tttgtgaaaa agcttaagga aagccgcgga tttagcatgt cacccacact tagattacga    780
aagcaaggat tgcagaaaaa aagatgagat acagttttga gggcaatata taaaatatat    840
aaatatagca acattccctt ctctctgtta tgtccacaat acttctaaaa gttgtaacat    900
atatctatac ataaaaactt gtaacaaaca tataattaaa acaactagtg acaagacgga    960
agttataagt tatcttctct acagaaacaa tacgtaggat ccattaaaat gtctaaaggt   1020
gaagaattat tcactggtgt tgtcccaatt ttggttgaat tagatggtga tgttaatggt   1080
cacaaatttt ctgtctccgg tgaaggtgaa ggtgatgcta cttacggtaa attgacctta   1140
aaatttattt gtactactgg taaattgcca gttccatggc caaccttagt cactactttc   1200
ggttatggtg ttcaatgttt tgcgagatac ccagatcata tgaaacaaca tgactttttc   1260
aagtctgcca tgccagaagg ttatgttcaa gaaagaacta ttttttttcaa agatgacggt   1320
aactacaaga ccagagctga agtcaagttt gaaggtgata ccttagttaa tagaatcgaa   1380
ttaaaaggta ttgatttttaa agaagatggt aacatttttag gtcacaaatt ggaatacaac   1440
tataactctc acaatgttta catcatggct gacaaacaaa agaatggtat caagttaac    1500
ttcaaaatta gacacaacat tgaagatggt tctgttcaat tagctgacca ttatcaacaa   1560
aatactccaa ttggtgatgg tccagtcttg ttaccagaca accattactt atccactcaa   1620
tctgccttat ccaaagatcc aaacgaaaag agagaccaca tggtcttgtt agaatttgtt   1680
actgctgctg gtattaccca tggtatggat gaattgtaca aataaactag t             1731
```

```
<210> SEQ ID NO 4
<211> LENGTH: 1714
<212> TYPE: DNA
<213> ORGANISM: Artificial Sequence
<220> FEATURE:
<223> OTHER INFORMATION: Synthetic nucleotide derived from E. coli and
      S. cerevisiae
```

<400> SEQUENCE: 4

```
gtcgactttc ttccttttct actatcttct cttttattat tatattatat tatcaataac        60
cctcatctct ctctctctct ctctctctct ctctctctct ctctctctct ctctctctct       120
ctctctctcc ttttttcttt cttttagatt tttttgcttt tgtttaattt cattccagtt       180
tccccccccc aatattaata ttcgttccta gagcctatca cacctaatat ttcccgtata       240
cattatagta aatacctcaa gacacttatg atagattttt ttccttaact caaacctaat       300
tagctctatg cataaagaaa gttttgaata aggaaatccg catattcaaa ttatcaaaca       360
tgcacttcat ctgcaaaact tccaaaaact ttctgctcgt taatagtcaa tgtatggtaa       420
tgcgaatgag caggtacccc ttattataat gattaatact tacatcatag ttaataatct       480
tatctcaggg tacccataat ttcaaccatc cttagcttcc attaaaaaca caatgagttg       540
cgttactagc gaagcggctt atctgttaat tcttgcttgc aaacatctta gctgaaagtg       600
aaaaggcaca gccgcacctg ctgaatgctc aacgtttgta ataatccgcc tatttccgcg       660
gaatcaatag ggctcctagc aggccgccat caattttcag cgtgccgcat taaaattata       720
ttaccaagat ttccatttcc gcggctgatt cctatcaata ttaagtaatc aatcttttcc       780
tcgtgattct ttgtgatgct cattcacaga ggactaatta agacatgtag cacaatatat       840
tcatataaaa gttggtgcag ttaatgatta attgcattgt tttccttgtt tctttctgtt       900
atacctgtcg aattaaacat aaagtgtata tgaattttaa ggggcacaaa taacaaagga       960
ttatttatca cctttaatag gatccattaa aatgtctaaa ggtgaagaat tattcactgg      1020
tgttgtccca atttggttg aattagatgg tgatgttaat ggtcacaaat tttctgtctc      1080
cggtgaaggt gaaggtgatg ctacttacgg taaattgacc ttaaaattta tttgtactac      1140
tggtaaattg ccagttccat ggccaacctt agtcactact ttcggttatg gtgttcaatg      1200
ttttgcgaga tacccagatc atatgaaaca acatgacttt tcaagtctg ccatgccaga      1260
aggttatgtt caagaaagaa ctatttttt caaagatgac ggtaactaca agaccagagc      1320
tgaagtcaag tttgaaggtg ataccttagt aatagaatc gaattaaaag gtattgattt      1380
taaagaagat ggtaacattt taggtcacaa attggaatac aactataact ctcacaatgt      1440
ttacatcatg gctgacaaac aaaagaatgg tatcaaagtt aacttcaaaa ttagacacaa      1500
cattgaagat ggttctgttc aattagctga ccattatcaa caaaatactc caattggtga      1560
tggtccagtc ttgttaccag acaaccatta cttatccact caatctgcct atccaaaga      1620
tccaaacgaa aagagagacc acatggtctt gttagaattt gttactgctg ctggtattac      1680
ccatggtatg gatgaattgt acaaataaac tagt                                 1714
```

<210> SEQ ID NO 5
<211> LENGTH: 1696
<212> TYPE: DNA
<213> ORGANISM: Artificial Sequence
<220> FEATURE:
<223> OTHER INFORMATION: Synthetic nucleotide derived from E. coli and
      S. cerevisiae

<400> SEQUENCE: 5

```
gtcgacggct gtatgtttat gattgctcga atcacgtttt tcttgttttt tcgtcaagaa        60
ttccagtcaa gttttccacc accttgaccc ttaaagcatc gacttttgtg ctcttgaatg       120
tgtttctaag aatacttgta aaggacaccc tctaatttcg tgtgcacttt tcacatatta       180
tcaagacaat cgttcctgta ctcagatgca ctgttactgt aaagactact atacaacaag       240
```

```
cgaaaaatga tgttcgaaaa cctttatttc tattttgaaa ggcatgtgtc tcgaggtcct        300
tgctttattg tgggtggtca tgccattctg taaaccttac ggtactgctc cgtctatatc        360
tttgaggttg ttatttcccc acaaatatgc gtttctaacc gaatattcat tcagtcggac        420
cggacaatag ctcttaactg cgtttaccgg agtaaatatc gtaagaattt gcatgcggtg        480
aaatacaggg aaaataagaa attcaccct aatacaaaaa gaaaactaag tttcacaata         540
cgtaaggata ttttagtggg gagaatattt cggagaataa agtttccaac tccgcggtgt       600
gaacaaccgc tcagcacgca gcgttattct cgagaaaagt ggccctgaaa taaggaaata       660
aagttactaa tgtttttcg ctgtacgata tcaaatgtga cgaagtaggc accccacgct         720
ataaattggc tactaaagtt tatgtcagta cttgggatcg ttgaaatact cggataaatt       780
atgttcctta tttttcatgg ttttcgtcat accacagttt accccagaat gagaaaggat       840
ctccttttga aataaaaagt acttaagggc aatgatattg agttgctaga cgtttggtta       900
gacgcctgtt ttgaaataaa aaagctgtct caaattaatc gagcaagcac agatcaaaca       960
agatacaaac aaagcttttc aacgtaatat ttactatcgg atccaaaagt atggctagct      1020
ccgaggacgt tataaaagag ttcatgagat ttaaagtaag aatggagggc agtgttaacg      1080
gtcacgaatt tgaaatagaa ggggaaggcg agggtagacc atatgaaggc actcaaacag      1140
ccaaactgaa ggttactaag ggaggtccat tgccttttgc atgggatatt ttgtcccctc      1200
aatttcaata cgggagtaaa gtgtatgtga acaccccgc tgacatccct gattataaga       1260
aactctcttt tccagaagga ttcaagtggg aaagagtcat gaacttcgaa gacggaggtg      1320
tagtaacggt aacccaggat tcttctcttc aagatggtag ctttatctat aaggttaaat      1380
tcattggagt caatttttcca tcagacggtc ccgttatgca gaagaaaact atgggatggg      1440
aagcctcgac agagaggttg tatccgcgtg atggggtgtt gaaaggcgaa attcataagg      1500
ctttaaagtt aaaagacggt ggtcattatt tagttgaatt caaatctatt tacatggcga      1560
aaaagcctgt ccaattacca ggttactact acgtggattc aaaactagat attacctcac      1620
ataatgagga ttatacaatc gtcgaacaat acgaacgagc agaaggcagg catcatcttt      1680
ttctataggc ggccgc                                                       1696
```

<210> SEQ ID NO 6
<211> LENGTH: 1706
<212> TYPE: DNA
<213> ORGANISM: Artificial Sequence
<220> FEATURE:
<223> OTHER INFORMATION: Synthetic nucleotide derived from E. coli and
      S. cerevisiae

<400> SEQUENCE: 6

```
gtcgactttc actcaaccac ctccaaaaaa taacaggttc atctaaagta aaagacttta         60
acttgctctt agtttccaaa ttaaatatct gcacgatagt accatttgct ctaacggaaa       120
taaccatctg agatggatgc atgatagcag aatcaccgcc catattcttc cttgtcactt       180
cattgccttt ggccaaatcc acgattgcaa cagagtttgt accgtccttt gtttctctaa       240
cagtgacgaa gtggtcactc tcgaaagtag ttgatctgaa gtcaaggaat tgaggggaaa       300
ttcctaagga catcagatcg accaattcgg taaattcaat gggtaggtca ctcattggtt       360
agaactttcg tgtaatttta ttttatagt tgaatatctt ctttctctct caactctgat         420
ccggattgtc gaggtttcaa taagttactc tgaacaacta atcaaatat ctccttattt         480 ctgtagattc cttcagttcc acttttact tttcttaatt ctctttgtat ttattcctag        540
```

```
cgacgaaaaa tgcgagatct cgaccaaaaa aagggggtag ggtaataaaa ttaaccctat      600 tatttttaa  ctttaaaacc tataatgtgc taatatttta ttataaacct ccttttttttg    660 cgttcaaacc ctgacacatt ttaagcccta tatttacggt attagttgat taaactccga     720
agcgaaagga attcggtcat tagcggctaa tagccgttgg ggtaaatcac ctacaagcaa     780
gtacacaaga gaacgttggc gttgttaagt caaagcacta atacattggg gctttaagag     840
tgtttataaa ggtctaacct gtaaaaatta tttaaacaac ttgaacaggc cttaaagttt     900
tcctcattcc gctcatcatc actaatattg ctctccgttt ttgaatacac acttgacact    960
aataagtatc acagaaaaaa agaaaatata ataaattagt attgcgatgg atccaaaagt    1020
atggctagct ccgaggacgt tataaaagag ttcatgagat ttaaagtaag aatggagggc    1080
agtgttaacg gtcacgaatt tgaaatagaa ggggaaggcg agggtagacc atatgaaggc    1140
actcaaacag ccaaactgaa ggttactaag ggaggtccat tgccttttgc atgggatatt    1200
ttgtcccctc aatttcaata cgggagtaaa gtgtatgtga acaccccgc tgacatccct     1260 gattataaga aactctcttt tccagaagga ttcaagtggg aaagagtcat gaacttcgaa    1320 gacgaggtg tagtaacggt aacccaggat tcttctcttc aagatggtag ctttatctat     1380
aaggttaaat tcattggagt caattttcca tcagacggtc ccgttatgca gaagaaaact    1440
atgggatggg aagcctcgac agagaggttg tatccgcgtg atggggtgtt gaaaggcgaa    1500
attcataagg ctttaaagtt aaaagacggt ggtcattatt tagttgaatt caaatctatt    1560
tacatggcga aaaagcctgt ccaattacca ggttactact acgtggattc aaaactagat    1620
attacctcac ataatgagga ttatacaatc gtcgaacaat acgaacgagc agaaggcagg    1680
catcatcttt ttctataggc ggccgc                                         1706
```

<210> SEQ ID NO 7
<211> LENGTH: 19
<212> TYPE: DNA
<213> ORGANISM: Artificial Sequence
<220> FEATURE:
<223> OTHER INFORMATION: Synthetic primer directed to gene YGR035C

<400> SEQUENCE: 7

```
gcgtgccata gtttcttcc                                                    19
```

<210> SEQ ID NO 8
<211> LENGTH: 19
<212> TYPE: DNA
<213> ORGANISM: Artificial Sequence
<220> FEATURE:
<223> OTHER INFORMATION: Synthetic primer directed to gene YGR035C

<400> SEQUENCE: 8

```
tcgtccctga gacttactc                                                    19
```

<210> SEQ ID NO 9
<211> LENGTH: 20
<212> TYPE: DNA
<213> ORGANISM: Artificial Sequence
<220> FEATURE:
<223> OTHER INFORMATION: Synthetic primer directed to gene SPS100

<400> SEQUENCE: 9

```
agtaccgtgg catcatggac                                                   20
```

<210> SEQ ID NO 10

```
<211> LENGTH: 20
<212> TYPE: DNA
<213> ORGANISM: Artificial Sequence
<220> FEATURE:
<223> OTHER INFORMATION: Synthetic primer directed to gene SPS100

<400> SEQUENCE: 10
gcagaaattg caccttgtgg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer directed to gene YOR186W

<400> SEQUENCE: 11
tttaagtccg ccatacgagc                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer directed to gene YOR186W

<400> SEQUENCE: 12
ctgcctacat cgccaatcac                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer directed to gene RTA1

<400> SEQUENCE: 13
aatggctact ctgctgttcg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer directed to gene RTA1

<400> SEQUENCE: 14
ctgcctacat cgccaatcac                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer directed to gene YLR346C

<400> SEQUENCE: 15
tgtcccatcg ggttagtttc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer directed to gene YLR346C

<400> SEQUENCE: 16
```
tgggcagcct tgagtaaatc                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer directed to gene MET28

<400> SEQUENCE: 17
aagcaggaag ggtatgaacg                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer directed to gene MET28

<400> SEQUENCE: 18
cagcagcaat gatagcaagc                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer directed to gene YLL056C

<400> SEQUENCE: 19
cagcagcaat gatagcaagc                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer directed to gene YLL056C

<400> SEQUENCE: 20
cggtcaattt cgcagcactg                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer directed to gene POX1

<400> SEQUENCE: 21
aagctgctct ggttaccgtg                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer directed to gene POX1

<400> SEQUENCE: 22
atacccatgt cctccgcaag                                          20

<210> SEQ ID NO 23
<211> LENGTH: 20
<212> TYPE: DNA

```
<213> ORGANISM: Artificial Sequence
<220> FEATURE:
<223> OTHER INFORMATION: Synthetic primer directed to gene HXT9

<400> SEQUENCE: 23
aagttgtggc ctcaaggaag                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer directed to gene HXT9

<400> SEQUENCE: 24
tgttgcgatt gccattcctc                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer directed to gene YGR287C

<400> SEQUENCE: 25
acttggcaat ccagtgatcc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer directed to gene YGR287C

<400> SEQUENCE: 26
tcggaggcat gttgcatttc                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer directed to gene YHL012W

<400> SEQUENCE: 27
ttgccttctt tccgaacagt                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer directed to gene YHL012W

<400> SEQUENCE: 28
gcccaagtcg attgaaggta                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer directed to gene ACT1

<400> SEQUENCE: 29
ttccagcctt ctacgtttcc                                               20
```

<210> SEQ ID NO 30
<211> LENGTH: 20
<212> TYPE: DNA
<213> ORGANISM: Artificial Sequence
<220> FEATURE:
<223> OTHER INFORMATION: Synthetic primer directed to gene ACT1

<400> SEQUENCE: 30
acgtgagtaa caccatcacc                                           20

<210> SEQ ID NO 31
<211> LENGTH: 29
<212> TYPE: DNA
<213> ORGANISM: Artificial Sequence
<220> FEATURE:
<223> OTHER INFORMATION: Synthetic primer directed to gene YGR035C

<400> SEQUENCE: 31
ttaagtcgac agagtttact tgcactacc                                 29

<210> SEQ ID NO 32
<211> LENGTH: 27
<212> TYPE: DNA
<213> ORGANISM: Artificial Sequence
<220> FEATURE:
<223> OTHER INFORMATION: Synthetic primer directed to gene YGR035C

<400> SEQUENCE: 32
ttaagtcgac ggagataata ccctctg                                   27

<210> SEQ ID NO 33
<211> LENGTH: 30
<212> TYPE: DNA
<213> ORGANISM: Artificial Sequence
<220> FEATURE:
<223> OTHER INFORMATION: Synthetic primer directed to gene YGR035C

<400> SEQUENCE: 33
aattggatcc tacgtattgt ttctgtagag                                30

<210> SEQ ID NO 34
<211> LENGTH: 30
<212> TYPE: DNA
<213> ORGANISM: Artificial Sequence
<220> FEATURE:
<223> OTHER INFORMATION: Synthetic primer directed to gene YLR346C

<400> SEQUENCE: 34
aattgtcgac tttcttcctt ttctactatc                                30

<210> SEQ ID NO 35
<211> LENGTH: 27
<212> TYPE: DNA
<213> ORGANISM: Artificial Sequence
<220> FEATURE:
<223> OTHER INFORMATION: Synthetic primer directed to gene YLR346C

<400> SEQUENCE: 35
ttaagtcgac aaccatcctt agcttcc                                   27

<210> SEQ ID NO 36
<211> LENGTH: 32
<212> TYPE: DNA
<213> ORGANISM: Artificial Sequence
<220> FEATURE:

<223> OTHER INFORMATION: Synthetic primer directed to gene YLR346C

<400> SEQUENCE: 36
ttatggatcc tattaaaggt gataaataat cc				32

<210> SEQ ID NO 37
<211> LENGTH: 28
<212> TYPE: DNA
<213> ORGANISM: Artificial Sequence
<220> FEATURE:
<223> OTHER INFORMATION: Synthetic primer directed to gene POX1

<400> SEQUENCE: 37
aattgtcgac tttcactcaa ccacctcc				28

<210> SEQ ID NO 38
<211> LENGTH: 29
<212> TYPE: DNA
<213> ORGANISM: Artificial Sequence
<220> FEATURE:
<223> OTHER INFORMATION: Synthetic primer directed to gene POX1

<400> SEQUENCE: 38
tatagtcgac tagattcctt cagttccac				29

<210> SEQ ID NO 39
<211> LENGTH: 33
<212> TYPE: DNA
<213> ORGANISM: Artificial Sequence
<220> FEATURE:
<223> OTHER INFORMATION: Synthetic primer directed to gene POX1

<400> SEQUENCE: 39
ttaaggatcc atcgcaatac taatttatta tat				33

<210> SEQ ID NO 40
<211> LENGTH: 29
<212> TYPE: DNA
<213> ORGANISM: Artificial Sequence
<220> FEATURE:
<223> OTHER INFORMATION: Synthetic primer directed to gene HXT9

<400> SEQUENCE: 40
ttaagtcgac acttgggttc tgtttctgg				29

<210> SEQ ID NO 41
<211> LENGTH: 29
<212> TYPE: DNA
<213> ORGANISM: Artificial Sequence
<220> FEATURE:
<223> OTHER INFORMATION: Synthetic primer directed to gene HXT9

<400> SEQUENCE: 41
attagtcgac atacggagcg taaacaacc				29

<210> SEQ ID NO 42
<211> LENGTH: 30
<212> TYPE: DNA
<213> ORGANISM: Artificial Sequence
<220> FEATURE:
<223> OTHER INFORMATION: Synthetic primer directed to gene HXT9

<400> SEQUENCE: 42
atatggatcc gatattgggt aagatacgaa				30

<210> SEQ ID NO 43
<211> LENGTH: 30
<212> TYPE: DNA
<213> ORGANISM: Artificial Sequence
<220> FEATURE:
<223> OTHER INFORMATION: Synthetic primer directed to gene YLR287C

<400> SEQUENCE: 43
ttaagtcgac ggctgtatgt ttatgattgc                              30

<210> SEQ ID NO 44
<211> LENGTH: 29
<212> TYPE: DNA
<213> ORGANISM: Artificial Sequence
<220> FEATURE:
<223> OTHER INFORMATION: Synthetic primer directed to gene YLR287C

<400> SEQUENCE: 44
ttaagtcgac gctcttaact gcgtttacc                               29

<210> SEQ ID NO 45
<211> LENGTH: 30
<212> TYPE: DNA
<213> ORGANISM: Artificial Sequence
<220> FEATURE:
<223> OTHER INFORMATION: Synthetic primer directed to gene YLR287C

<400> SEQUENCE: 45
ttaaggatcc gatagtaaat attacgttga                              30

<210> SEQ ID NO 46
<211> LENGTH: 30
<212> TYPE: DNA
<213> ORGANISM: Artificial Sequence
<220> FEATURE:
<223> OTHER INFORMATION: Synthetic primer directed to gene YHL012W

<400> SEQUENCE: 46
tattgtcgac gcctcttctt tcattttagc                              30

<210> SEQ ID NO 47
<211> LENGTH: 30
<212> TYPE: DNA
<213> ORGANISM: Artificial Sequence
<220> FEATURE:
<223> OTHER INFORMATION: Synthetic primer directed to gene YHL012W

<400> SEQUENCE: 47
attagtcgac attagatgct ttcgagatgc                              30

<210> SEQ ID NO 48
<211> LENGTH: 32
<212> TYPE: DNA
<213> ORGANISM: Artificial Sequence
<220> FEATURE:
<223> OTHER INFORMATION: Synthetic primer directed to gene YHL012W

<400> SEQUENCE: 48
taatggatcc tgatcttgta tatactatgt ag                           32

<210> SEQ ID NO 49
<211> LENGTH: 27
<212> TYPE: DNA
<213> ORGANISM: Artificial Sequence
<220> FEATURE:
<223> OTHER INFORMATION: Synthetic Opd mutagenesis oligonucleotide

<400> SEQUENCE: 49
gagttagtgt taagggcggc cgcccgg                                    27

<210> SEQ ID NO 50
<211> LENGTH: 27
<212> TYPE: DNA
<213> ORGANISM: Artificial Sequence
<220> FEATURE:
<223> OTHER INFORMATION: Synthetic Opd mutagenesis oligonucleotide

<400> SEQUENCE: 50
gcaagtcagc gcggtggtga gcagcag                                    27

<210> SEQ ID NO 51
<211> LENGTH: 27
<212> TYPE: DNA
<213> ORGANISM: Artificial Sequence
<220> FEATURE:
<223> OTHER INFORMATION: Synthetic Opd mutagenesis oligonucleotide

<400> SEQUENCE: 51
gacgtgatgg atagcgtgaa ccccgac                                    27

<210> SEQ ID NO 52
<211> LENGTH: 29
<212> TYPE: DNA
<213> ORGANISM: Artificial Sequence
<220> FEATURE:
<223> OTHER INFORMATION: Synthetic Opd mutagenesis oligonucleotide

<400> SEQUENCE: 52
gccctcctgg gcaaccgttc gtggcaaac                                  29

<210> SEQ ID NO 53
<211> LENGTH: 27
<212> TYPE: DNA
<213> ORGANISM: Artificial Sequence
<220> FEATURE:
<223> OTHER INFORMATION: Synthetic Opd mutagenesis oligonucleotide

<400> SEQUENCE: 53
cgcaaagctc tagtggaaaa ggctgtg                                    27

<210> SEQ ID NO 54
<211> LENGTH: 28
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (13)..(15)
<223> OTHER INFORMATION: n is a, c, g, or t

<400> SEQUENCE: 54
gaccacatcc cgnnnagtgc gattggtc                                   28

<210> SEQ ID NO 55
<211> LENGTH: 30
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (14)..(16)
<223> OTHER INFORMATION: n is a, c, g, or t

```
<400> SEQUENCE: 55
gaccggcttg tggnnngacc cgccactttc                                              30

<210> SEQ ID NO 56
<211> LENGTH: 29
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (15)..(17)
<223> OTHER INFORMATION: n is a, c, g, or t

<400> SEQUENCE: 56
tgtcgacttt cgatnnnggt cgcgacgtc                                               29

<210> SEQ ID NO 57
<211> LENGTH: 25
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (12)..(14)
<223> OTHER INFORMATION: n is a, c, g, or t

<400> SEQUENCE: 57
cgaccggctt gnnnttcgac ccgcc                                                   25

<210> SEQ ID NO 58
<211> LENGTH: 30
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (15)..(17)
<223> OTHER INFORMATION: n is a, c, g, or t

<400> SEQUENCE: 58
tcatcggtct agacnnnatc ccgtggagtg                                              30

<210> SEQ ID NO 59
<211> LENGTH: 31
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (16)..(18)
<223> OTHER INFORMATION: n is a, c, g, or t

<400> SEQUENCE: 59
actcacgagc acatcnnngg cagctcggca g                                            31

<210> SEQ ID NO 60
<211> LENGTH: 31
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (15)..(17)
```

```
<223> OTHER INFORMATION: n is a, c, g, or t

<400> SEQUENCE: 60
cgagtgcatc agccnnnctg ggcaaccgtt c                                    31

<210> SEQ ID NO 61
<211> LENGTH: 27
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (13)..(15)
<223> OTHER INFORMATION: n is a, c, g, or t

<400> SEQUENCE: 61
tcgaatgact ggnnnttcgg gttttcg                                         27

<210> SEQ ID NO 62
<211> LENGTH: 27
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (13)..(15)
<223> OTHER INFORMATION: n is a, c, g, or t

<400> SEQUENCE: 62
gggttttcga gcnnngtcac caacatc                                         27

<210> SEQ ID NO 63
<211> LENGTH: 29
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (14)..(16)
<223> OTHER INFORMATION: n is a, c, g, or t

<400> SEQUENCE: 63
catcatggac gtgnnngata gcgtgaacc                                       29

<210> SEQ ID NO 64
<211> LENGTH: 26
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (13)..(15)
<223> OTHER INFORMATION: n is a, c, g, or t

<400> SEQUENCE: 64
gagcacatct gcnnnagctc ggcagg                                          26

<210> SEQ ID NO 65
<211> LENGTH: 25
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
```

```
<222> LOCATION: (11)..(13)
<223> OTHER INFORMATION: n is a, c, g, or t

<400> SEQUENCE: 65
gctgttcggg nnntcgagct atgtc                                          25

<210> SEQ ID NO 66
<211> LENGTH: 32
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (15)..(17)
<223> OTHER INFORMATION: n is a, c, g, or t

<400> SEQUENCE: 66
tgttcgggtt ttcgnnntat gtcaccaaca tc                                  32

<210> SEQ ID NO 67
<211> LENGTH: 27
<212> TYPE: DNA
<213> ORGANISM: Artificial Sequence
<220> FEATURE:
<223> OTHER INFORMATION: Synthetic Opd mutagenesis oligonucleotide
<220> FEATURE:
<221> NAME/KEY: misc_feature
<222> LOCATION: (13)..(15)
<223> OTHER INFORMATION: n is a, c, g, or t

<400> SEQUENCE: 67
cacatctgcg tcnnntcggc aggattc                                        27

<210> SEQ ID NO 68
<211> LENGTH: 338
<212> TYPE: PRT
<213> ORGANISM: Artificial Sequence
<220> FEATURE:
<223> OTHER INFORMATION: Chemically synthesized wild-type OPH Enzyme

<400> SEQUENCE: 68
```

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Phe Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Lys Ala Ala Ala
145                 150                 155                 160

```
Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Thr Asp Asp
        195                 200                 205

Leu Ser Tyr Leu Thr Ala Leu Ala Ala Arg Gly Tyr Leu Ile Gly Leu
    210                 215                 220

Asp His Ile Pro His Ser Ala Ile Gly Leu Glu Asp Asn Ala Ser Ala
225                 230                 235                 240

Ser Ala Leu Leu Gly Ile Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

Met Asp Arg Val Asn Pro Asp Gly Met Ala Phe Ile Pro Leu Arg Val
    290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser Glx

<210> SEQ ID NO 69
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 69

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Val Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Phe Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Gln Ala Ala Ile Phe Glu Ser Glu Gly
            180
```

```
                180                 185                 190
Leu Ser Pro Ser Arg Val Cys Ile Gly His Ser Asp Asp Thr Asp Asp
            195                 200                 205

Leu Ser Tyr Leu Thr Ala Leu Ala Ala Arg Gly Tyr Leu Ile Gly Leu
        210                 215                 220

Asp His Ile Pro His Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

Met Asp Ser Val Asn Pro Asp Gly Met Ala Phe Ile Pro Leu Arg Val
        290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser Glx

<210> SEQ ID NO 70
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 70

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Val Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Phe Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205
```

```
Leu Ser Tyr Leu Thr Ala Leu Ala Ala Arg Gly Tyr Leu Ile Gly Leu
    210                 215                 220

Asp His Ile Pro Trp Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

Met Asp Ser Val Asn Pro Asp Gly Met Ala Phe Ile Pro Leu Arg Val
290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser Glx

<210> SEQ ID NO 71
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 71

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Val Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Asp Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220
```

```
Asp His Ile Pro Trp Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
            245                 250                 255

Lys Ala Leu Ile Asp Gln Gly Tyr Met Lys Gln Ile Leu Val Ser Asn
        260                 265                 270

Asp Trp Leu Phe Gly Phe Ser Ser Tyr Val Thr Asn Ile Met Asp Val
            275                 280                 285

Met Asp Ser Val Asn Pro Asp Gly Met Ala Phe Ile Pro Leu Arg Val
        290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser Glx
```

<210> SEQ ID NO 72
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 72

```
Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Val Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Cys Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Gln Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp His Ile Pro Trp Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
```

```
                    245                 250                 255
Lys Ala Leu Ile Asp Gln Gly Tyr Met Lys Gln Ile Leu Val Ser Asn
                260                 265                 270

Asp Trp Leu Phe Gly Phe Ser Ser Tyr Val Thr Asn Ile Met Asp Val
            275                 280                 285

Met Asp Ser Val Asn Pro Asp Gly Met Ala Phe Ile Pro Leu Arg Val
290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser Glx

<210> SEQ ID NO 73
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 73

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Gly
                20                  25                  30

Ser Ser Ala Gly Phe Leu Arg Ala Trp Pro Glu Phe Phe Gly Ser Arg
            35                  40                  45

Lys Ala Leu Val Glu Lys Ala Val Arg Gly Leu Arg Arg Ala Arg Ala
        50                  55                  60

Ala Gly Val Arg Thr Ile Val Asp Val Ser Thr Phe Asp Val Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Asp Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Ala Ala Ile Phe Glu Ser Glu Gly Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp His Ile Pro Trp Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270
```

Asp Trp Leu Phe Gly Phe Ser Ser Tyr Val Thr Asn Ile Met Asp Val
            275                 280                 285

Met Asp Ser Val Asn Pro Asp Gly Met Ala Phe Ile Pro Leu Arg Val
            290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser Glx

<210> SEQ ID NO 74
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 74

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Val
            20                  25                  30

Ser Ser Ala Gly Phe Leu Arg Ala Trp Pro Glu Phe Phe Gly Ser Arg
        35                  40                  45

Lys Ala Leu Val Glu Lys Ala Val Arg Gly Leu Arg Arg Ala Arg Ala
    50                  55                  60

Ala Gly Val Arg Thr Ile Val Asp Val Ser Thr Phe Asp Val Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Asp Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp His Ile Pro Trp Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

```
Met Asp Ser Val Asn Pro Asp Gly Met Ala Phe Ile Pro Leu Arg Val
290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser Glx

<210> SEQ ID NO 75
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 75

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Val
                20                  25                  30

Ser Ser Ala Gly Phe Leu Arg Ala Trp Pro Glu Phe Phe Gly Ser Arg
            35                  40                  45

Lys Ala Leu Val Glu Lys Ala Val Arg Gly Leu Arg Arg Ala Arg Ala
50                  55                  60

Ala Gly Val Arg Thr Ile Val Asp Val Ser Thr Phe Asp Val Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Asp Asp Pro Pro Leu Ser Met Arg Leu
            100                 105                 110

Arg Ser Val Glu Glu Leu Thr Gln Phe Phe Leu Arg Glu Ile Gln Tyr
            115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
            195                 200                 205

Leu Ser Tyr Leu Thr Ala Leu Ala Ala Arg Gly Tyr Leu Ile Gly Leu
210                 215                 220

Asp His Ile Pro Trp Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Val Ser Ser Tyr Val Thr Asn Ile Met Asp Val
            275                 280                 285

Met Asp Ser Val Asn Pro Asp Gly Met Ala Phe Ile Pro Leu Arg Val
290                 295                 300

Ile Pro Phe Leu Arg Glu Lys Gly Val Pro Gln Glu Thr Leu Ala Gly
```

```
            305                 310                 315                 320
Ile Thr Val Thr Asn Pro Ala Arg Phe Leu Ser Pro Thr Leu Arg Ala
                325                 330                 335

Ser Glx

<210> SEQ ID NO 76
<211> LENGTH: 338
<212> TYPE: PRT
<213> ORGANISM: Artificial Sequence
<220> FEATURE:
<223> OTHER INFORMATION: Chemically synthesized variant OPH enzyme

<400> SEQUENCE: 76

Met Ile Thr Asn Ser Gly Asp Arg Ile Asn Thr Val Arg Gly Pro Ile
1               5                   10                  15

Thr Ile Ser Glu Ala Gly Phe Thr Leu Thr His Glu His Ile Cys Gly
                20                  25                  30

Ser Ser Ala Gly Phe Leu Arg Ala Trp Pro Glu Phe Phe Gly Ser Arg
            35                  40                  45

Lys Ala Leu Val Glu Lys Ala Val Arg Gly Leu Arg Arg Ala Arg Ala
        50                  55                  60

Ala Gly Val Arg Thr Ile Val Asp Val Ser Thr Phe Asp Val Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Asp Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Gly Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
210                 215                 220

Asp His Ile Pro Trp Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Leu Tyr Val Thr Asn Ile Met Asp Val
        275                 280                 285

Met Asp Ser Val Asn Pro Asp Gly Met Ala Phe Ile Pro Leu Arg Val
290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335
```

Ser Glx

<210> SEQ ID NO 77
<211> LENGTH: 1014
<212> TYPE: DNA
<213> ORGANISM: Artificial Sequence
<220> FEATURE:
<223> OTHER INFORMATION: Chemically synthesized codon-optimized S308L
      gene for expression in S. cerevisiae

<400> SEQUENCE: 77

| | | | | | |
|---|---|---|---|---|---|
| atgataacaa | atagtgggga | cagaattaac | acagtacgtg | gccctataac catctcagaa | 60 |
| gctggtttca | ctttgacaca | tgaacatatt | tgtggctcta | gtgctggctt tctaagggct | 120 |
| tggccagagt | ttttcggaag | cagaaaagct | ctggttgaga | aggctgtgcg tggtctacgt | 180 |
| cgtgcaagag | cagctggtgt | aaggactatt | gttgacgtct | ctactttcga tgtgggtaga | 240 |
| gatgtttccc | tgttagccga | ggtgtcaagg | gctgctgatg | tccacattgt tgctgcaacc | 300 |
| ggtttgtggg | atgatccgcc | tctatctatg | agacttagat | ccgtagaaga acttactcaa | 360 |
| tttttcttaa | gggaaattca | atacggaata | gaggacacag | gtattagagc aggtattatc | 420 |
| aaagtcgcca | ccacggggaa | ggcaacacca | tttcaagaat | tagttctaag agctgcggcg | 480 |
| agggcatctt | tagctaccgg | cgtcccggtt | acaactcaca | ctgccgcaag ccaaagagga | 540 |
| ggtgaacaac | aggcagcaat | ttttgaatcg | gaggggttaa | gtccatcgag agtctgcatt | 600 |
| ggtcattcag | acgatacaga | tgatttatcc | tatttgactg | ccttggctgc tagaggatac | 660 |
| ttgatcggac | ttgatcatat | cccatggtca | gccattggat | tagaagataa tgcctccgct | 720 |
| tctgctcttc | taggtaacag | aagctggcaa | accagggcat | tgttgatcaa ggcccttatt | 780 |
| gaccaaggtt | atatgaaaca | gatattagta | tcgaatgact | ggttgtttgg ttttagttta | 840 |
| tatgtgacga | acataatgga | tgtaatggat | tctgttaatc | ccgacggtat ggcgttcatt | 900 |
| ccattgagag | tgatcccttt | tctgagggaa | aaaggcgttc | ctcaggaaac attggccggt | 960 |
| ataacggtta | ccaatcccgc | acgtttctta | tcaccaactc | tgagggcgtc ttaa | 1014 |

<210> SEQ ID NO 78
<211> LENGTH: 916
<212> TYPE: DNA
<213> ORGANISM: Artificial Sequence
<220> FEATURE:
<223> OTHER INFORMATION: Chemically synthesized NEOr gene and upstream
      promoter

<400> SEQUENCE: 78

| | | | | | |
|---|---|---|---|---|---|
| atttatgcag | aggccgaggc | cgcctcggcc | tctgagctat | tccagaagta gtgaggaggc | 60 |
| ttttttggag | gcctaggctt | ttgcaaagat | cgatcaagag | acaggatgag gatcgtttcg | 120 |
| catgattgaa | caagatggat | tgcacgcagg | ttctccggcc | gcttgggtgg agaggctatt | 180 |
| cggctatgac | tgggcacaac | agacaatcgg | ctgctctgat | gccgccgtgt tccggctgtc | 240 |
| agcgcagggg | cgcccggttc | tttttgtcaa | gaccgacctg | tccggtgccc tgaatgaact | 300 |
| gcaagacgag | gcagcgcggc | tatcgtggct | ggccacgacg | ggcgttcctt gcgcagctgt | 360 |
| gctcgacgtt | gtcactgaag | cgggaaggga | ctggctgcta | ttgggcgaag tgccggggca | 420 |
| ggatctcctg | tcatctcacc | ttgctcctgc | cgagaaagta | tccatcatgg ctgatgcaat | 480 |
| gcggcggctg | catacgcttg | atccggctac | ctgcccattc | gaccaccaag cgaaacatcg | 540 |
| catcgagcga | gcacgtactc | ggatggaagc | cggtcttgtc | gatcaggatg atctggacga | 600 |

```
agagcatcag gggctcgcgc cagccgaact gttcgccagg ctcaaggcga gcatgcccga    660
cggcgaggat ctcgtcgtga cccatggcga tgcctgcttg ccgaatatca tggtggaaaa    720
tggccgcttt tctggattca tcgactgtgg ccggctgggt gtggcggacc gctatcagga    780
catagcgttg gctacccgtg atattgctga agagcttggc ggcgaatggg ctgaccgctt    840
cctcgtgctt tacggtatcg ccgctcccga ttcgcagcgc atcgccttct atcgccttct    900
tgacgagttc ttctga                                                    916

<210> SEQ ID NO 79
<211> LENGTH: 653
<212> TYPE: DNA
<213> ORGANISM: Artificial Sequence
<220> FEATURE:
<223> OTHER INFORMATION: Chemically synthesized GAPDH promoter sequence

<400> SEQUENCE: 79
cgagtttatc attatcaata ctcgccattt caaagaatac gtaaataatt aatagtagtg     60
attttcctaa ctttatttag tcaaaaaatt agccttttaa ttctgctgta acccgtacat    120
gccaaaatag ggggcgggtt acacagaata tataacatcg taggtgtctg ggtgaacagt    180
ttattcctgg catccactaa atataatgga gcccgctttt taagctggca tccagaaaaa    240
aaaagaatcc cagcaccaaa atattgtttt cttcaccaac catcagttca taggtccatt    300
ctcttagcgc aactacagag aacagggca caaacaggca aaaacgggc acaacctcaa    360 tggagtgatg caacctgcct ggagtaaatg atgacacaag gcaattgacc cacgcatgta    420
tctatctcat tttcttacac cttctattac cttctgctct ctctgatttg gaaaaagctg    480
aaaaaaaagg ttgaaaccag ttccctgaaa ttattcccct acttgactaa taagtatata    540
aagacggtag gtattgattg taattctgta aatctatttc ttaaacttct taaattctac    600
ttttatagtt agtctttttt ttagttttaa aacaccaaga acttagtttc gaa           653

<210> SEQ ID NO 80
<211> LENGTH: 190
<212> TYPE: DNA
<213> ORGANISM: Artificial Sequence
<220> FEATURE:
<223> OTHER INFORMATION: Chemically synthesized TcycI transcriptional
      terminator

<400> SEQUENCE: 80
atccgctcta accgaaaagg aaggagttag acaacctgaa gtctaggtcc ctatttattt     60
ttttatagtt atgttagtat taagaacgtt atttatattt caaattttc ttttttttct    120 gtacagacgc gtgtacgcat gtaacattat actgaaaacc ttgcttgaga aggttttggg    180
acgctcgaag                                                           190

<210> SEQ ID NO 81
<211> LENGTH: 592
<212> TYPE: DNA
<213> ORGANISM: Artificial Sequence
<220> FEATURE:
<223> OTHER INFORMATION: Chemically synthesized 5' flanking ribosomal
      sequence

<400> SEQUENCE: 81
atgagagtag caaacgtaag tctaaaggtt gttttatagt agttaggatg tagaaaatgt     60
attccgatag gccattttac atttggaggg acgttgaaa gtggacagag gaaaggtgc     120 ggaaatggct gattttgatt gtttatgttt tgtgtgatga ttttacattt ttgcatagta    180
```

```
ttaggtagtc agatgaaaga tgaatagaca taggagtaag aaaacataga atagttaccg      240
ttattggtag gagtgtggtg gggtggtata gtccgcattg ggatgttact ttcctgttat      300
ggcatggatt tccctttagg gtctctgaag cgtatttccg tcaccgaaaa aggcagaaaa      360
agggaaactg aagggaggat agtagtaaag tttgaatggt ggtagtgtaa tgtatgatat      420
ccgttggttt tggtttcggt tgtgaaaagt ttttggtat gatattttgc aagtagcata       480
tatttcttgt gtgagaaagg tatattttgt atgttttgta tgttcccgcg cgtttccgta      540
ttttccgctt ccgcttccgc agtaaaaaat agtgaggaac tgggttaccc gg              592
```

<210> SEQ ID NO 82
<211> LENGTH: 663
<212> TYPE: DNA
<213> ORGANISM: Artificial Sequence
<220> FEATURE:
<223> OTHER INFORMATION: Chemically synthesized 3' flanking ribosomal
      sequence

<400> SEQUENCE: 82

```
ggcacctgtc actttggaaa aaaatatac gctaagattt ttggagaata gcttaaattg      60 aagttttttct cggcgagaaa tacgtagtta aggcagagcg acagagaggg caaagaaaa      120 taaaagtaag attttagttt gtaatgggag gggggggttta gtcatggagt acaagtgtga    180
ggaaaagtag ttgggaggta cttcatgcga aagcagttga agacaagttc gaaaagagtt     240
tggaaacgaa ttcgagtagg cttgtcgttc gttatgtttt tgtaaatggc ctcgtcaaac     300
ggtggagaga gtcgctaggt gatcgtcaga tctgcctagt ctctatacag cgtgttaat      360 tgacatgggt tgatgcgtat tgagagatac aatttgggaa gaaattccca gagtgtgttt    420
cttttgcgtt taacctgaac agtctcatcg tgggcatctt gcgattccat tggtgagcag    480
cgaaggattt ggtggattac tagctaatag caatctattt caaagaattc aaacttgggg    540
gaatgccttg ttgaatagcc ggtcgcaaga ctgtgattct tcaagtgtaa cctcctctca    600
aatcagcgat atcaaacgta ccattccgtg aaacaccggg gtatctgttt ggtggaacct    660
gat                                                                  663
```

<210> SEQ ID NO 83
<211> LENGTH: 365
<212> TYPE: PRT
<213> ORGANISM: Flavobacterium sp.
<220> FEATURE:
<221> NAME/KEY: misc_feature
<223> OTHER INFORMATION: Flavobacterium sp. parathion hydrolase gene

<400> SEQUENCE: 83

```
Met Gln Thr Arg Arg Val Val Leu Lys Ser Ala Ala Ala Gly Thr
1               5                   10                  15

Leu Leu Gly Gly Leu Ala Gly Cys Ala Ser Val Ala Gly Ser Ile Gly
                20                  25                  30

Thr Gly Asp Arg Ile Asn Thr Val Arg Gly Pro Ile Thr Ile Ser Glu
            35                  40                  45

Ala Gly Phe Thr Leu Thr His Glu His Ile Cys Gly Ser Ser Ala Gly
        50                  55                  60

Phe Leu Arg Ala Trp Pro Glu Phe Phe Gly Ser Arg Lys Ala Leu Ala
65                  70                  75                  80

Glu Lys Ala Val Arg Gly Leu Arg Arg Ala Arg Ala Ala Gly Val Arg
                85                  90                  95
```

| | | | | | | | | | | |
|---|---|---|---|---|---|---|---|---|---|---|
Thr Ile Val Asp Val Ser Thr Phe Asp Ile Gly Arg Asp Val Ser Leu
            100                 105                 110

Leu Ala Glu Val Ser Arg Ala Ala Asp Val His Ile Val Ala Ala Thr
        115                 120                 125

Gly Leu Trp Phe Asp Pro Pro Leu Ser Met Arg Leu Arg Ser Val Glu
    130                 135                 140

Glu Leu Thr Gln Phe Phe Leu Arg Glu Ile Gln Tyr Gly Ile Glu Asp
145                 150                 155                 160

Thr Gly Ile Arg Ala Gly Ile Ile Lys Val Ala Thr Thr Gly Lys Ala
                165                 170                 175

Thr Pro Phe Gln Glu Leu Val Leu Lys Ala Ala Arg Ala Ser Leu
            180                 185                 190

Ala Thr Gly Val Pro Val Thr Thr His Thr Ala Ala Ser Gln Arg Asp
        195                 200                 205

Gly Glu Gln Gln Ala Ala Ile Phe Glu Ser Glu Gly Leu Ser Pro Ser
    210                 215                 220

Arg Val Cys Ile Gly His Ser Asp Asp Thr Asp Asp Leu Ser Tyr Leu
225                 230                 235                 240

Thr Ala Leu Ala Ala Arg Gly Tyr Leu Ile Gly Leu Asp His Ile Pro
                245                 250                 255

His Ser Ala Ile Gly Leu Glu Asp Asn Ala Ser Ala Ser Ala Leu Leu
            260                 265                 270

Gly Ile Arg Ser Trp Gln Thr Arg Ala Leu Leu Ile Lys Ala Leu Ile
        275                 280                 285

Asp Gln Gly Tyr Met Lys Gln Ile Leu Val Ser Asn Asp Trp Leu Phe
290                 295                 300

Gly Phe Ser Ser Tyr Val Thr Asn Ile Met Asp Val Met Asp Arg Val
305                 310                 315                 320

Asn Pro Asp Gly Met Ala Phe Ile Pro Leu Arg Val Ile Pro Phe Leu
                325                 330                 335

Arg Glu Lys Gly Val Pro Gln Glu Thr Leu Ala Gly Ile Thr Val Thr
            340                 345                 350

Asn Pro Ala Arg Phe Leu Ser Pro Thr Leu Arg Ala Ser
        355                 360                 365

<210> SEQ ID NO 84
<211> LENGTH: 1693
<212> TYPE: DNA
<213> ORGANISM: Flavobacterium sp.
<220> FEATURE:
<221> NAME/KEY: misc_feature
<223> OTHER INFORMATION: Flavobacterium sp. parathion hydrolase gene

<400> SEQUENCE: 84
ggatccgagc ggcttaccgg cgccctgctc gaccggttga cccaccatgt ccatatcctc    60
gagatgaacg ggggcagcta tcggcttgcc agcagccgga aacggcaaaa gcacagccac   120
cacgcacagc aagaggaggt gcccccccca tgacctgatc agaaaacccc tcatctgctg   180
tgctgaacgg ccttcgctac gctccagacc gttcagcaca gcagatgaaa gcaccgcctc   240
gacaagaggc tttttgttca atccaactgg tacactctta caccggaatc ttgcacaatt   300
ttaccccggc attgacatct gacgcgtcaa cagtaaaaga acaaccggt tcagatctgc    360 agcctgactc ggcaccagtc gctgcaagca gagtcgtaag caatcgcaag ggggcagcat   420
gcaaacgaga agggttgtgc tcaagtctgc ggccgccgca ggaactctgc tcggcggcct   480
ggctgggtgc gcgagcgtgg ctggatcgat cggcacaggc gatcggatca ataccgtgcg   540

-continued

| | |
|---|---|
| cggtcctatc acaatctctg aagcgggttt cacactgact cacgagcaca tctgcggcag | 600 |
| ctcggcagga ttcttgcgtg cttggccaga gttcttcggt agccgcaaag ctctagcgga | 660 |
| aaaggctgtg agaggattgc gccgcgccag agcggctggc gtgcgaacga ttgtcgatgt | 720 |
| gtcgactttc gatatcggtc gcgacgtcag tttattggcc gaggtttcgc gggctgccga | 780 |
| cgttcatatc gtggcggcga ccggcttgtg gttcgacccg ccactttcga tgcgattgag | 840 |
| gagtgtagag gaactcacac agttcttcct gcgtgagatt caatatggca tcgaagacac | 900 |
| cggaattagg gcgggcatta tcaaggtcgc gaccacaggc aaggcgaccc cctttcagga | 960 |
| gttagtgtta aaggcggccg cccgggccag cttggccacc ggtgttccgg taaccactca | 1020 |
| cacggcagca agtcagcgcg atggtgagca gcaggccgcc atttttgagt ccgaaggctt | 1080 |
| gagcccctca cgggtttgta ttggtcacag cgatgatact gacgatttga gctatctcac | 1140 |
| cgccctcgct gcgcgcggat acctcatcgg tctagaccac atcccgcaca gtgcgattgg | 1200 |
| tctagaagat aatgcgagtg catcagccct cctgggcatc cgttcgtggc aaacacgggc | 1260 |
| tctcttgatc aaggcgctca tcgaccaagg ctacatgaaa caaatcctcg tttcgaatga | 1320 |
| ctggctgttc gggttttcga gctatgtcac caacatcatg gacgtgatgg atcgcgtgaa | 1380 |
| ccccgacggg atggccttca ttccactgag agtgatccca ttcctacgag agaagggcgt | 1440 |
| cccacaggaa acgctggcag gcatcactgt gactaacccg gcgcggttct tgtcaccgac | 1500 |
| cttgcgggcg tcatgacgcc atctggatcc ttccagccag cggccactat tccccgtcaa | 1560 |
| gataccgaac gatgaagtcg cgcatcgatc gataggcatc ttcaatttga tcagggctgc | 1620 |
| cacctccaaa gccgtggcca cccctgtcga tagtcttgag gacgtagggc acaccgtgct | 1680 |
| tttcgaactg cag | 1693 |

```
<210> SEQ ID NO 85
<211> LENGTH: 351
<212> TYPE: DNA
<213> ORGANISM: Saccharomyces cerevisiae
<220> FEATURE:
<221> NAME/KEY: misc_feature
<223> OTHER INFORMATION: Accession No. YGR035C Chr 7

<400> SEQUENCE: 85
```

| | |
|---|---|
| atgttactca caccagccaa gactacaaga acggaagact cagcaaactc aacagatgac | 60 |
| agcagtaaaa gcagtaattc attcatgcgt gccatagttt cttcccttat ggttaagccc | 120 |
| ataacatctc tgactaatac agtcacatgc agacaaagtt cccatcacaa tagctctcca | 180 |
| agtaaaatca caagatatga tttaatcaaa gctgctgctg aaaatgactt gaaaaggagt | 240 |
| aagtctcagg gacgagaaaa atccagaaga aactctaatc gtagaaataa tgaagaaatt | 300 |
| tttgtggcca atactgcttc agaaatccaa cggactaaaa gtagcatata g | 351 |

```
<210> SEQ ID NO 86
<211> LENGTH: 981
<212> TYPE: DNA
<213> ORGANISM: Saccharomyces cerevisiae
<220> FEATURE:
<221> NAME/KEY: misc_feature
<223> OTHER INFORMATION: Accession No. YHR139C Chr 8

<400> SEQUENCE: 86
```

| | |
|---|---|
| atgaaattca catcagtgct agcatttttt cttgcaactt taacagcttc tgcaacacca | 60 |
| ctttacaaga ggcagaacgt tacttctggc ggcggtacgg tccccgtgat catcacgggt | 120 |

```
ggacctgctg tatctggtag ccagtcaaac gttactacca caacgctatt caactctact    180
tccaccttaa acatcactca actttaccaa attgctactc aagttaatca gactttacaa    240
agcgaatcgt cttccggcat tataatcgtc acaaactggc gttccattga aactttgagt    300
ttcttctgct caatcgtttt taatacatca aagaccattg tcattactga aatttcttta    360
tggggtgtac caatattgag tagttcggac gcggaaggta gaggcacttt ggttgccggt    420
agagataaag ttgtgtattc tggtgttttc cctccttaca ctgttcctgt gggcgttttg    480
tctggtcaga agaatgttca atggttcttt gatgcctgtg agccaactct gattgccagc    540
aactccacaa tcagaactca atactcgaat tttacgagcg cacaaatatc ttctaatgcc    600
tcctccggga ccaatacatc ctcatcatcc tccagtccat ggttccaat tatatacgaa     660 gaaggatatt ctcaaagctt aattcaatca ctaagttcta gtatccaagg tttggttgtt    720
gtcagctctg gtacaagtca caacagtacc gtggcatcat ggacatcggt cgacttccct    780
gtcgtttatg caagtgatgg atccagtggt catgatggtt caggaattgg gttcataagt    840
aacacaagta ttccacaagg tgcaatttct gctgggtact tgtcaccaat ccaagcgcaa    900
actttgttgt ctattgctat ccataatcaa gtcacaagta gtagcgagtt acaacaaatc    960
ttccctgtta gtcaacaata a                                              981

<210> SEQ ID NO 87
<211> LENGTH: 435
<212> TYPE: DNA
<213> ORGANISM: Saccharomyces cerevisiae
<220> FEATURE:
<221> NAME/KEY: misc_feature
<223> OTHER INFORMATION: Accession No. YOR186W Chr 15

<400> SEQUENCE: 87
atgactttgg cttttacgac cttcgctatt tccaagataa acaattcgtc cacgaatgaa     60
gattctaaag tcatgatact gtgcgatgag catcaccctt tcgagaaggg ttactttaag    120
tccgccatac gagccttcgg caacagcatt aagctaggat taatgggtaa ctcgcgacca    180
gaagacgcag cgtccatatt ccaagataaa aatattcctc acgatctgac gacggaagaa    240
ttcaggttgc agctggtctg tatggctttt tcctggttca tatttggtct cttcatcgcc    300
tgcttactac tttgtatcac gcttgtgcta acatcgcgat atcctggaga aaatgaaaac    360
aaagccacgg aagttgtgcc atccagtaat attgacgacg aagaaaagca attatcgctt    420
tccgacatga tttag                                                     435

<210> SEQ ID NO 88
<211> LENGTH: 954
<212> TYPE: DNA
<213> ORGANISM: Saccharomyces cerevisiae
<220> FEATURE:
<221> NAME/KEY: misc_feature
<223> OTHER INFORMATION: Accession No. YGR213C Chr 7

<400> SEQUENCE: 88
atggcaaaag acggcttcga gttatataga tacactccgg aattaggtgc gagtatactt     60
tttacggtac tttttgcagt atcagggta gcatttgtaa ttttactatt ccattattct    120
gtgaaaagta aaggagagt tggctctctt atgaagtccc aacccgtatt gcggtattac    180
ggtacggtaa acttagcagg agcgtacatt ccctttatat ttgggtgttt tgttgagtgt    240
gtgggctttg cgtttagatg taaatcaagc aaagacacca cactactaaa cccctatatt    300
attcaaacgg ttttcttgct ggtgtctcca acattatatg ctgccagtat ttacatgatt    360
```

| | |
|---|---|
| tttggtagaa tggctactct gctgttcgca gaaaacttaa tgatcatgcc cgctagattc | 420 |
| aatactacaa tatttgtgat tggcgatgta ggcagtcttc tattacaagc aattggtggt | 480 |
| gctatgatgt ctaaagtgac aagtgcatct tctggttctc atctcgttac agctggtttg | 540 |
| ttcattcaaa ttgctttttt tggtctcttc attataaatg aggttttgtt cattttcaag | 600 |
| atgagcaaaa aaccaaccaa tgtatcggta aggtatggta gttggaaata cctaaacatt | 660 |
| gctttattgg tgaacagttt cctgatttta attaggtcga tcgtcagagc tgttgaattt | 720 |
| attcagggtt atgacggaga aattgcctcg cacgagtggt atctttatat ttttgatggt | 780 |
| ttaccaatgt tttactcgt attaattttt attgtggcgt tcccactaat taacattttt | 840 |
| agaatacatg aagagtctat tcaagcgcaa caatcagcaa gatttgacgg caccgactat | 900 |
| cctgacgttg aggtgacgtc tatcgaagaa gatctcgctt caaagagcga ataa | 954 |

<210> SEQ ID NO 89
<211> LENGTH: 306
<212> TYPE: DNA
<213> ORGANISM: Saccharomyces cerevisiae
<220> FEATURE:
<221> NAME/KEY: misc_feature
<223> OTHER INFORMATION: Accession No. YLR346C Chr 12

<400> SEQUENCE: 89

| | |
|---|---|
| atgcaatcga tcagtaattg tcccatcggg ttagtttcaa aaaacacaat caattcagct | 60 |
| tccactattg cagagtgggt agcatgtcca tggaaatata tcaacgttgt tggttcaggc | 120 |
| agatatgtga gcaataaacc tgataaaatt accagatatg attactcaa ggctgcccag | 180 |
| gaagcggaaa tgcaggagtt gcttacaaga aatgatatga aggtagaca taaacgtaat | 240 |
| aagaaaagta agatagcatt ggagactata gcggaagaaa actcttcaac tgaaagcctt | 300 |
| ttttaa | 306 |

<210> SEQ ID NO 90
<211> LENGTH: 564
<212> TYPE: DNA
<213> ORGANISM: Saccharomyces cerevisiae
<220> FEATURE:
<221> NAME/KEY: misc_feature
<223> OTHER INFORMATION: Accession No. YIR017C Chr 9

<400> SEQUENCE: 90

| | |
|---|---|
| atgagtgcga acaagggtg ggaaaagaaa tcaacaaaca ttgacattgc aagcaggaag | 60 |
| ggtatgaacg tgaacaatct ttcggaacat ctacagaacc tgtatcaag cgattcagag | 120 |
| ctgggctcgc gcttgctatc attgctgctg gttagcagtg caacgcgga ggagctcatt | 180 |
| agcatgataa ataatggcca ggatgtctcg cagtttaaga agctccgcga gccgagaaag | 240 |
| gggaaggttg ccgcaacaac agcagttgtt gtaaaagaag aggaagctcc cgtgagcact | 300 |
| tctaacgaac tggataagat taagcaagag cggagaagaa agaacacaga ggcgtcgcag | 360 |
| cggttccgca ttcgcaagaa acaaaagaat tttgagaaca tgaataagct gcagaactta | 420 |
| aacacgcaaa tcaacaaact tcgcgatcgt atagagcaat tgaacaagga aaatgagttt | 480 |
| tggaaagcaa agctcaatga cattaacgag attaagtctt tgaaattgtt gaatgacatt | 540 |
| aagagacgga acatgggcag gtag | 564 |

<210> SEQ ID NO 91
<211> LENGTH: 897
<212> TYPE: DNA

<213> ORGANISM: Saccharomyces cerevisiae
<220> FEATURE:
<221> NAME/KEY: misc_feature
<223> OTHER INFORMATION: Accession No. YLL056C  Chr 12

<400> SEQUENCE: 91

| | | | | | | |
|---|---|---|---|---|---|---|
| atgaaagtat | ttataactgg | tgcttctggc | ttcattggtt | ctgccgtatt | atctgaacta | 60 |
| atatcctcgg | gtcatgaagt | tgttggcttg | gcaaggtcag | acgaggctgc | tgcaaagatt | 120 |
| aagtcgattg | atcctgctgc | aaaaatcctt | cgcggtgatc | tcaaggatct | ggaaattttg | 180 |
| aaaaaaggtg | ccactgaatc | tgatggcgtt | attcatttag | gatttgtgca | tgattttaaa | 240 |
| aattttgaac | agtgctgcga | aattgaccgt | caggccactg | tagctatgct | agagtcactt | 300 |
| aaaggttcta | acaagccttt | cttatatacg | aatggtacac | tttctttgcg | accaaacaaa | 360 |
| gttgctaacg | aacaggatgg | tattgatgaa | gattccaaaa | ttttgcgtgc | tgtcactgaa | 420 |
| caggttgcct | tgagttacaa | agacaaaggt | gtttcagcaa | gaattgtcag | actcccattc | 480 |
| tcggttcatg | gcaaggggga | caaggctttt | gtaccaatat | aatgaatat | tgccaaagct | 540 |
| gccgaaaaat | ctggctatgt | cggacaaggc | acaaacgctt | gggcggctgt | acatcgtttg | 600 |
| gatacggctc | ctctgttcag | acttgtttta | gagaaaggaa | aaacaggaca | agtgtatcat | 660 |
| tgcgttggtg | aacaaggtat | accattcaaa | gatattgcgc | gtgtgattgg | agaaattttg | 720 |
| aatgttcccg | tggcctctat | ccctgttgat | gacgcggaaa | gtcattttgg | cttcctcact | 780 |
| tgttttgtca | ctagagatgg | cccagtttca | agcgaaggta | ccagaaaaga | gctgggatgg | 840 |
| cagccacaac | aaatcggtct | tcttgaagat | atccgtgcga | actatagctt | aaactga | 897 |

<210> SEQ ID NO 92
<211> LENGTH: 2247
<212> TYPE: DNA
<213> ORGANISM: Saccharomyces cerevisiae
<220> FEATURE:
<221> NAME/KEY: misc_feature
<223> OTHER INFORMATION: Accession No. YGL205W  Chr 7

<400> SEQUENCE: 92

| | | | | | | |
|---|---|---|---|---|---|---|
| atgacgagac | gtactactat | taatcccgat | tcggtggttc | tgaatcctca | aaaatttatc | 60 |
| cagaaagaaa | gggcggattc | gaaaatcaaa | gttgaccaag | ttaacacatt | tttagagtca | 120 |
| tccccggaga | ggagaactct | gacgcacgcc | ttaatagacc | aaatagtgaa | tgatcctata | 180 |
| ttgaaaactg | atacggacta | ttacgatgct | aaaaaaatgc | aagagagaga | aattactgcc | 240 |
| aaaaaaatag | ctaggcttgc | tagttatatg | gagcacgata | tcaaaacagt | gcgcaaacac | 300 |
| tttcgcgaca | ctgacctgat | gaaagagttg | caagcaaatg | atccagacaa | agcttcgcct | 360 |
| ttaacaaaca | aagaccttt | tatattcgat | aagagattgt | cacttgtagc | aaatattgat | 420 |
| cctcaattgg | gtacgcgcgt | gggtgtacac | ttggggctat | ttggtaattg | tatcaagggc | 480 |
| aatggtactg | atgagcaaat | ccggtattgg | ttgcaggaga | gaggtgccac | tttgatgaaa | 540 |
| ggtatatatg | gctgttttgc | aatgactgag | ttaggacatg | gttccaatgt | tgcccagctg | 600 |
| cagactaggg | ctgtgtacga | taagcaaaat | gatacttttg | taattgatac | acctgatcta | 660 |
| actgccacca | atggtggat | tggtgggct | gcccattctg | ccacgcacgc | tgccgtgtac | 720 |
| gccagattga | tcgttgaagg | taaagactac | ggtgtaaaaa | cattcgttgt | tcctctgaga | 780 |
| gaccccttcga | ctttccaact | gttagctggt | gtttccatag | gggatattgg | agcgaagatg | 840 |
| ggtcgtgacg | gtattgataa | tggctggatc | cagttcagaa | acgtagttat | ccctagagaa | 900 |
| tttatgctaa | gtagatttac | caaagttgtc | cgttctccag | atggttcagt | caccgtcaaa | 960 |

```
actgagccac aattggatca aatttctggt tatagtgcat tgttaagtgg tagagttaac    1020
atggtcatgg attcatttag gtttggctcc aaatttgcta ctattgctgt acgttacgcg    1080
gttggtcgtc agcaattcgc acctagaaag ggattgtctg aaacacaatt aatcgactat    1140
ccccttcacc aatatcgtgt tttaccacaa ttgtgtgttc catatttggt gtcacctgta    1200
gcttttaagt taatggacaa ctattattcc actttggacg agttatacaa cgcttcctca    1260
tctgcataca aagctgctct ggttaccgtg agtaaaaagt tgaagaattt atttattgat    1320
agcgccagct tgaaagccac caatacttgg ttaattgcta cactgattga tgagttgaga    1380
cagacttgcg gaggacatgg gtattcacag tataacggat ttggtaaagg ctatgacgac    1440
tgggtggttc agtgcacatg ggagggtgat aataatgttt tatctttaac ttcagcaaaa    1500
tcaatattga aaaatttat cgattcagcc acaaagggta gatttgacaa cactggat    1560 gtggactcat tctcttactt aaaacctcag tacataggat ctgtggtttc tggagaaata    1620
aagagtggtt taaggagtt gggtgattat actgaaattt ggtctatcac cttaatcaaa    1680
ttactggcac atattggtac tttagttgaa aaatcaagaa gtattgatag cgtttctaag    1740
cttttagtct tagtatccaa atttcatgcc ttgcgctgca tgttgaaaac ctattacgac    1800
aagttaaact ctcgtgattc acatatttcc gatgaaatta caaaggaatc tatgtggaat    1860
gtttataagt tattttcctt gtattttatt gacaagcatt ccggagaatt ccaacaattc    1920
aagatcttca ctcctgatca gatctctaaa gttgtgcagc cacaactatt ggctcttttg    1980
ccaattgtga ggaaagactg tataggtctg acagactcct ttgaattacc tgacgcgatg    2040
ttaaattctc ctataggtta ctttgatggc gatatctatc acaattactt caatgaagtt    2100
tgccgcaata atccagtgga ggcagatggg gcagggaagc cttcttatca tgcgctgttg    2160
agcagcatgc tcggtagagg tttcgaattt gaccaaaagt taggtggtgc agctaatgcg    2220
gaaattttat cgaaaataaa caagtga                                       2247

<210> SEQ ID NO 93
<211> LENGTH: 1704
<212> TYPE: DNA
<213> ORGANISM: Saccharomyces cerevisiae
<220> FEATURE:
<221> NAME/KEY: misc_feature
<223> OTHER INFORMATION: Accession No. YJL219W  Chr 10

<400> SEQUENCE: 93
atgtccggtg ttaataatac atccgcaaat gatttatcca ctaccgagtc taactctaac     60
tcagtagcaa atgcaccatc tgtaaaaact gagcataatg actctaaaaa ctccctcaac    120
ctggatgcca ctgaaccacc tattgactta cctcaaaaac ccctctctgc atataccacc    180
gtcgcaatcc tgtgtttgat gattgcattt ggcggcttca tctttggttg ggataccggt    240
accatttctg gttttgttaa cctttctgat ttcatcagaa ggttcggtca aaaaatgac     300 aagggaacct actacttatc gaaagtaaga atgggtttga tcgtctcaat attcaacatt    360
ggctgcgcca taggcggaat tgtcttgtca aaagtcggtg atatatatgg tcgtcgtatt    420
ggattgatta cagttactgc catttacgtt gtaggcatcc taatccaaat aacttccata    480
aacaagtggt accaatactt cattggaaga attatttctg gcctaggagt gggaggcatt    540
gctgtccttt ccccaatgtt gatatctgaa gttgctccca acaaatcag aggaaccctg    600 gtccaattgt accagctgat gtgtacgatg ggtatttttc taggatactg taccaattac    660
ggtaccaaga actatcacaa cgccactcaa tggagagtcg gccttggtct ttgctttgcc    720
```

```
tggactacat tcatggttag tggaatgatg tttgtaccag aatcaccacg ttacctgatt    780
gaggttggta aagatgagga agcgaaacgt tcactttcga aatccaacaa agtctcagtc    840
gacgatccag ccttgttagc agaatatgac actataaagg cgggaatcga acttgaaaag    900
ctggcaggta acgcatcatg gtctgaacta ctctccacta aaacaaaggt ctttcagcgt    960
gttctcatgg gagtgatgat ccaatcgctg cagcaattaa ccggtgataa ctacttcttt   1020
tactacggca ccaccatctt caaatctgtc ggtctaaagg actcctttca gacttcgatc   1080
attatcggtg tggttaattt tttctcttca ttcatagcgg tatacaccat tgagaggttt   1140
ggacgccgta cgtgtctatt gtggggtgct gcttctatgc tatgctgctt tgctgtgttt   1200
gcctccgtcg gtgtgacaaa gttgtggcct caaggaagca gtcaccaaga cattacttct   1260
cagggcgccg gtaactgtat gattgtgttt actatgttct tcattttttc gttcgccacc   1320
acttgggcag gcggctgtta cgttattgtc tcagagacgt ttcctcttag ggtcaaatca   1380
agaggaatgg caatcgcaac agctgcaaac tggatgtggg gtttcctgat tagtttcttt   1440
accccattca ttaccggggc aatcaacttt tactacggtt atgtattctt aggctgtctg   1500
gtttttgcat acttttatgt cttttttcttt gtcccagaaa caaaaggcct gacgctggag   1560
gaggtgaata ctatgtggct ggaaggtgtg ccagcatgga aatcagcctc atgggtgcca   1620
ccagaaagaa gaaccgcaga ttacgatgct gacgccatag accatgacga tagaccaatc   1680
tacaagaggt tcttttccag ctaa                                          1704

<210> SEQ ID NO 94
<211> LENGTH: 1770
<212> TYPE: DNA
<213> ORGANISM: Saccharomyces cerevisiae
<220> FEATURE:
<221> NAME/KEY: misc_feature
<223> OTHER INFORMATION: Accession No. YGR287C  Chr 7

<400> SEQUENCE: 94
atgactattt cttctgcaca tccagagaca gaaccaaagt ggtggaaaga ggccacgttc     60
tatcaaattt acccagcaag tttcaaagac tctaatgacg atggctgggg tgacatgaaa    120
gggattgcct ccaagctgga gtacatcaaa gagcttggtg ccgatgccat ttggatctca    180
ccattctacg actcgccaca agatgatatg gttacgata ttgccaacta cgaaaaggtc    240
tggccaacat atggtacgaa tgaagactgc tttgccttga tcgaaaagac acataagctt    300
ggtatgaaat ttatcaccga cttggtcatc aatcactgtt ccagcgaaca tgaatggttc    360
aaagagagca gatcctcgaa gactaatcca aagcgtgact ggttcttctg gagacctcct    420
aaaggttatg acgccgaagg caagccaatt cctccaaaca attggaaatc ctattttggt    480
ggttccgcat ggaccttcga tgaaaagaca caagaattct acttgcgttt gttttgctcc    540
actcaacctg atttgaattg ggagaatgaa actgtagaa aggcaatcta cgaaagtgcc    600
gttggatact ggttagacca tggtgtagac ggctttagaa ttgatgtcgg aagtttgtac    660
tccaaagttg taggtttacc agatgctcct gttgttgaca aaaactcgac ttggcaatcc    720
agtgatccat acacattgaa tggaccacgt attcacgagt ccatcaaga atgaatcaa    780 ttcatcagaa acagagtgaa ggatggcagg agattatga cagttggtga aatgcaacat    840
gcctccgacg aaactaagag actttatacg agtgcttcaa gacacgaact tagtgagtta    900
tttaactttt cccacactga tgtggggact tcacctttgt tccgttacaa cttggtccca    960
tttgaactga aggattggaa gattgccctt gctgagctgt tcaggtacat taatggtaca   1020
```

```
gattgttggt caacaatcta tctggaaaat cacgaccaac ctcgttcaat tacgagattt   1080
ggtgacgatt ctcccaagaa ccgtgttatt tctggtaagt tactctctgt gttgctaagt   1140
gccttgaccg gtactctata tgtgtatcag ggacaagagc ttggccaaat caatttcaag   1200
aactggcctg ttgaaaagta cgaggatgtc gaaatcagaa acaactacaa tgccattaaa   1260
gaagagcatg gggaaaactc agaggagatg aaaaagtttt tagaagccat tgcccttatc   1320
tccagggacc atgctagaac acctatgcaa tggtctcgtg aggagccaaa tgctggtttt   1380
tctggtccta gtgctaaacc atggttttac ttgaacgact ctttcagaga aggcattaac   1440
gtcgaagatg aaatcaagga tcccaactcg gttttgaact tctggaagga ggccttgaag   1500
tttagaaagg cgcataaaga cattactgtg tacggatacg atttcgagtt tattgattta   1560
gacaataaga agttgtttag cttcacaaag aagtacaaca ataaaacatt gtttgcggct   1620
ttgaacttta gctctgatgc gacagatttc aagattccaa atgatgattc atcgttcaag   1680
ttagagtttg gaaactatcc aaagaaggag gtagatgcct cttccagaac attgaagcca   1740
tgggaaggaa gaatatatat cagcgaatga                                    1770

<210> SEQ ID NO 95
<211> LENGTH: 1482
<212> TYPE: DNA
<213> ORGANISM: Saccharomyces cerevisiae
<220> FEATURE:
<221> NAME/KEY: misc_feature
<223> OTHER INFORMATION: Accession No. YHL012W  Chr 8

<400> SEQUENCE: 95
atgacggttt tctctggagt aaataaaata gagtttgaag gtactttcga aggtattgga     60
aaggatgttg ttatgtcaca aatgataagg gccttgcaga acattttcc ttcgatacgt    120 gacaagaatt atgagtttag cctatttttg cacattttc aaagatatgt cttagaaaat    180
acttcaatca cccatgatct agtttgtgac aaaattagat taccgataat tgatgaagtg    240
gttgaactcg atgatattaa aaattacggt ttgttagagg gtaaactatt atcaaagtta    300 gctatttaa aattaaccgg aaaggctaat ccaatcattg gtaaagaaag ccctttattc    360
gaagtaaaaa atgggatgtc ttcattggat gtaatagttc gacaaacgca aaatttgaat    420
gtacgatata attcagacgt tcctcttata tttatgacct cgcttgaaac tgaatctcaa    480
gtatcaaact tccttgaaga gcattattct tctagcaaag tgagatggaa aaccgtagtt    540
cagtcaagct ttccacaaat tgataaagat agattattac ctatcgattt acaaataaat    600
tctcatgaaa atgatttttg gtatccttgc gggactggta acctaactga cactttgtat    660
ttttcaggag aattggacaa attaattgct caaggaaaag agattttatt tgtttcaaat    720
gttgacaatt tgggcgctac aggagatttg aacattttaa atttcatcat aaatgaaaaa    780
atcgagtatc ttgttgaagt agttgaaagg actgcaaatg tttcaaacac tggagtgttg    840
gcaacatata aaggtaaact acgatcggtt tattacaact gcttatccaa tgaaagtgca    900
agcacgtgtc gaattgtcaa cactaataac atttggattg atttgaaaaa gctaaaggtg    960
ctaatagagt ctaatagttt aaatttgcca attcattcta gtgaaagtaa aataacacac   1020
aaaaatgaag agatagagtg tcttcaattt aagacacagt tggtcgattg tattgccttc   1080
tttccgaaca gtcgagtatt gaaagtatca agagacagat ttttacccct aagaacatgt   1140
aaggacttgt ttttgttgaa atcaacatta tatgatctcg attcaaatgg aacatttaac   1200 ctctacccte tgaaatttgg attattacct tcaatcgact tgggcgatga gtttgcaact   1260
```

```
tatgagactt ttaagatagg agtaccagat attcctaata ttctggaatt agagcattta    1320
actgtgatgg gaaatgtgtt ttttggtcgt aatataactc tgaaagggac ggtcattata    1380
atatgtgatg aaaatgatgt aattactgtt cccgatggct ctattttgga aaatgtaacg    1440
atttggcata aatctcagct ggaggatatg aatggatatt aa                      1482
```

ORGANOPHOSPHORUS HYDROLASE

CROSS-REFERENCE TO RELATED APPLICATION

This application claims the benefit of U.S. Provisional Patent Application Ser. No. 60/976,602, filed Oct. 1, 2007, the contents of which is hereby incorporated in its entirety by reference.

RIGHTS IN THE INVENTION

This invention was made, in part, with United States Government support under Defense Advance Research Project Agency (DARPA contract W31P4Q-06-C-0474). The United States Government has certain rights in the invention.

TECHNICAL FIELD

The present disclosure relates to systems, organisms, and methods of sensing an analyte and/or product(s) of analyte transformation.

BACKGROUND

Chemical weapons such as organophosphate (OP) nerve agents, although developed nearly 100 years ago, continue to be a serious threat to both army and civilian personnel. Nerve agents were used during the 1980's Iraq/Iran war, by the Japanese Aum Shinrikyo terrorist cult in the Matsumoto attack of 1994, and in the 1995 Tokyo subway attack. In this latter incident, the terrorists left a plastic bag with the volatile nerve agent sarin on an underground train and pierced the bags with the tips of their umbrellas before escaping. The resulting vapor injured 3,796 people, caused 12 deaths and mass panic. OP nerve agents are particularly suited as weapons of mass destruction since they are generally cheap and are relatively easy to produce by developing nations or terrorists. Nerve agents may be particularly hazardous since they may be easily dispersed, they may be easily concealed, and they may be lethal in small quantities. For example, by some calculations, circulating air within a 250 m$^3$ airplane passenger compartment may be rendered lethal in about 2.5 minutes by the vapor from a teaspoon of liquid sarin. The resulting vapor may be readily absorbed through the skin or inhaled and may result in rapid incapacitation and death. Other OP nerve agents such as VX (O-ethyl S-[2-diisopropylaminoethyl]methylphosphonothiolate), although less volatile than sarin, may be even more deadly since only miniscule amounts of liquid are needed to be lethal. Aerosolized VX droplets could be dispersed by simple spraying (e.g., using a crop duster) or by a more conventional missile attack. Nerve agents may act by inhibiting the enzyme acetylcholinesterase (AChE). AChE is a very efficient enzyme that hydrolyzes approximately 10,000 acetylcholine (ACh) molecules per second. Consequently, AChE inhibition by nerve gases causes near instantaneous ACh flooding. This may result in respiratory symptoms, chest tightness, dimming of vision and eye pain and in severe cases of exposure vomiting, abdominal pain, bladder/bowel hyperactivity, incontinence, convulsions, respiratory failure, paralysis and death.

The threat of OP nerve agents is compounded by the fact that some countries have massive stockpiles. World stockpiles are reported to exceed 200 kilotons, with U.S. reserves alone amounting to 30 kilotons. In addition, OP compounds are widely used in agricultural and domestic pest controls such as pesticides. For example, in the U.S. over 40 million kg of OP pesticides are used annually, with another 20 million kg produced annually for export. With this overuse, there are legitimate public health concerns about OP contamination of soil and water systems. Unintentional exposure (water, food, soil) to OP pesticides may cause 1 to 3 million cases of pesticide poisonings annually worldwide.

SUMMARY

Accordingly, there is a need for safe and effective methods to dispose of these man-made toxic compounds and for self-sustainable detection systems. The present disclosure relates to biosensors for detecting (1) one or more analytes (e.g., chemical agents) and/or (2) the transformation (e.g., degradation) of one or more analytes (e.g., chemical agents). Biosensors of the disclosure may be useful in any application where it is desirable to detect and/or transform (e.g., remove) a species of interest. For example, according to some embodiments, a biosensor may be used to detect and/or remove a chemical contaminant in a production process and/or a hazardous environment.

In some embodiments, a biosensor may include a microbe. For example, a biosensor of the disclosure may include a genetically engineered strain of yeast (e.g., *Saccharomyces cerevisiae*). A yeast may (i) fluoresce more in the presence of an analyte (e.g., contact with a nerve gas warfare agent and/or pesticide) than in the absence of the analyte, (ii) transform (e.g., hydrolyze) the analyte, and/or (iii) differentially fluoresce upon transformation of the analyte.

A yeast, in some embodiments, may include promoters, coding sequences, proteins, and/or other components for transforming (e.g., degrading) one or more analytes. A yeast may also include promoters, coding sequences, proteins, and/ or other components for detecting one or more analytes. For example, a yeast may be genetically engineered to (i) express enzymes not normally found in yeast in order to confer the ability to biodegrade a chemical agent and; (ii) possess a dual fluorescent reporter system transcriptionally fused to yeast promoters which are differentially activated to fluoresce at one wavelength in the presence of the chemical agent contamination or another wavelength in the presence of the biodegraded products.

The yeast *S. cerevisiae*, which is a robust non-pathogenic microorganism that is resistant to environmental extremes, may be used as a self-contained biosensor according to some embodiments of the disclosure. Exogenous substrates and/or consumables may not be required. In addition, a simple hand-held illumination device may allow distinct visual detection of the chemical agent contamination and biodegraded products in embodiments using a dual fluorescent reporter system.

The present disclosure further relates to detecting transformation of an analyte. In some embodiments of the disclosure, transformation of an analyte may include partial and/or complete degradation (e.g., hydrolysis) of the analyte. Transformation may include converting (e.g., anabolically or catabolically) an analyte to another form. For example, an analyte may be conjugated to another molecule and/or integrated into a larger molecule. An analyte transformation product may be more innocuous (e.g., less toxic) than its parent analyte.

In some embodiments an analyte may be an organophosphate.

In some embodiments, the present disclosure relates to a yeast biosensor comprising (a) a first expression control sequence operably linked to a first nucleic acid encoding a first reporter, wherein said first expression control sequence drives expression of the first reporter if an organophosphate is present, (b) a second expression control sequence operably linked to a second nucleic acid encoding a second reporter, wherein said second expression control sequence drives expression of the second reporter if an organophosphate hydrolytic product is present, and (c) at least one enzyme that hydrolyzes the organophosphate to produce the organophosphate hydrolytic product. The first and/or second reporter may comprise a nucleic acid encoding a fluorescent protein, a light protein, an enzyme, and/or an ice nucleation protein (inaZ). A fluorescent protein may comprise a green fluorescent protein (GFP) or its variants (e.g., enhanced GFP (EGFP), yeast enhanced GFP (YeGFP), *Aequorea coerelescens* GFP (AcGFP)), DsRed or its variants (e.g., DsRed monomer, DsRed2, DsRed express), RedStar2, ASRed2, HcRed1, AmCyan1, ZsYellow1, ZsGreen1, and/or AmCyan1. A light protein may comprise insect luciferase (luc), bacterial luciferase (luxAB), bacterial bioluminescence (luxCDABE), and/or *Renilla* luciferase (mc). An enzyme may comprise uroporphyrinogen III methyltransferase (cobA), secreted alkaline phosphatase (SEAP), β-galactosidase, and/or β-glucuronidase (GUS).

The first and second reporters, according to some embodiments, may be different from each other. A first expression control sequence may comprise nucleotides −500 to −1 (e.g., nucleotides −1000 to −1) of a gene selected from the group consisting of Accession No. YGR035C (SEQ ID NO:85), Accession No. YHR139C (SEQ ID NO:86), Accession No. YOR186W (SEQ ID NO:87), Accession No. YGR213C (SEQ ID NO:88), Accession No. YLR346C (SEQ ID NO:89), Accession No. YIR017C (SEQ ID NO:90), and Accession No. YLL056C (SEQ ID NO:91). A second expression control sequence may comprise nucleotides −500 to −1 (e.g., nucleotides −1000 to −1) of a gene selected from the group consisting of Accession No. YGL205W (SEQ ID NO:92), Accession No. YJL219W (SEQ ID NO:93), Accession No. YGR287C (SEQ ID NO:94), and Accession No. YHL012W (SEQ ID NO:95).

In some embodiments, a first and/or second expression control sequence may include promoter fragments larger or smaller than the foregoing examples. Smaller fragments may be desirable where activity of an expression control sequence is attributed to specific domains (e.g., an upstream activating sequence, an upstream repressing sequence, and/or a TATA sequence) of the complete sequence.

According to some embodiments, an organophosphate degrading enzyme may be selected from the group consisting of organophosphorus hydrolase (OPH), phosphotriesterase, OpdA, organophosphorus acid anhydrolase (OPAA), DFPase, and paraoxonase (PON) (Table 15). These enzymes may hydrolyze one or more organophosphate bonds (Tables 16 and 17). An enzyme, in some embodiments, may be intracellular, may be presented at a cell surface, and/or may be secreted. A yeast biosensor may be permeabilized by application of an external agent (e.g., an alcohol). In some embodiments, a yeast biosensor may include a mutation in an ergosterol biosynthetic gene. In some embodiments, a yeast biosensor may include a defect (e.g., mutation) in (a) cell wall synthesis, maintenance, or degradation, (b) cell membrane synthesis, maintenance, or degradation, (c) cell repair, and/or (d) cell transport (e.g., drug export pump or import pump). For example, a yeast biosensor may include one or more proteins and/or nucleic acid(s) encoding one or more proteins capable of actively importing a chemical agent into the sensor.

The disclosure relates, in part, to a method of identifying a yeast gene that is upregulated by an organophosphate including (a) contacting a yeast with the organophosphate, (b) collecting RNA from the yeast, (c) contacting the RNA with a yeast mircoarray having feature loci that correspond to yeast genes under conditions that permit hybridization of complimentary sequences, (d) comparing a metric of the hybridization at each feature locus with the same metric of hybridization at a corresponding feature locus for RNA from yeast not contacted with the organophosphate, (e) identifying a feature locus where the hybridization metric is higher for the yeast contacted with the organophosphate than the yeast not contacted with the organophosphate, and (f) correlating the identified feature locus with its respective yeast gene.

In some embodiments, a yeast biosensor that is sensitive to an organophosphate may be prepared by (a) identifying a yeast gene that is upregulated by an organophosphate, (b) identifying at least one expression control sequence of the identified gene, (c) operably linking a nucleic acid comprising the expression control sequence to a nucleic acid encoding a reporter, and (d) contacting the operably linked nucleic acids with a cell under conditions that permit uptake of the nucleic acids. The operably linked nucleic acids may be comprised in a yeast plasmid or integrated into a locus of a yeast chromosome. A reported may be selected from the group consisting of enhanced green fluorescent protein, yeast enhanced green fluorescent protein, *Aequorea coerelescens* green fluorescent protein, DsRed monomer, DsRed2, DsRed express, RedStar2, ASRed2, HcRed1, AmCyan1, ZsYellow1, ZsGreen1, and/or AmCyan1, insect luciferase, bacterial luciferase, bacterial bioluminescence, *Renilla* luciferase, uroporphyrinogen III methyltransferase, secreted alkaline phosphatase, β-galactosidase, β-glucuronidase, an ice nucleation protein or combinations thereof.

The present disclosure also relates to a method of identifying a yeast gene that is upregulated by an organophosphate hydrolytic product and/or a process of organophosphate hydrolysis. In some embodiments, this method may include (a) contacting a yeast with an organophosphate hydrolytic product, and (b) comparing the transcription profile of a recombinant OPH+ yeast with wild-type yeast in the presence of the organophosphate. In some embodiments, this method may include (a) contacting a yeast with the organophosphate hydrolytic product, collecting RNA from the yeast, (b) contacting the RNA with a yeast mircoarray having feature loci that correspond to yeast genes under conditions that permit hybridization of complimentary sequences, (c) comparing a metric of the hybridization at each feature locus with the same metric of hybridization at a corresponding feature locus for RNA from yeast not contacted with the organophosphate hydrolytic product, (d) identifying a feature locus where the hybridization metric is higher for the yeast contacted with the organophosphate hydrolytic product than the yeast not contacted with the organophosphate hydrolytic product, and (e) correlating the identified feature locus with its respective yeast gene. This method may further include confirming differential expression by quantitative reverse transcription PCR.

The present disclosure also relates to a method of identifying a yeast gene that is upregulated by or during organosphosphate hydrolysis. In some embodiments, this method may include (a) contacting a recombinant OPH+ yeast with an organophosphate under conditions that permit organophosphate hydrolysis, (b) collecting RNA from the recombinant OPH+ yeast, (c) contacting the subtracted RNA with a yeast mircoarray having feature loci that correspond to yeast genes under conditions that permit hybridization of complimentary sequences, (d) comparing a metric of the hybridization at each feature locus with the same metric of hybridization at a corresponding feature locus for RNA from yeast lacking OPH contacted with the organophosphate, (e) identifying a feature locus where the hybridization metric is higher for the recombinant OPH+ yeast contacted with the organophosphate than the yeast lacking OPH contacted with the organophosphate, and (f) correlating the identified feature locus with its respective yeast gene. This method may further include confirming differential expression by quantitative reverse transcription PCR.

A yeast biosensor that is sensitive to an organophosphate hydrolytic product and/or organophosphate hydrolysis, according to some embodiments, may be prepared by (a) identifying a yeast gene that is upregulated by an organophosphate hydrolytic product, (b) identifying at least one expression control sequence of the identified gene. (c) operably linking a nucleic acid comprising the expression control sequence to a nucleic acid encoding a reporter, and (d) contacting the operably linked nucleic acids with a cell under conditions that permit uptake of the nucleic acids. The operably linked nucleic acids may be comprised in a yeast plasmid or integrated into a locus of a yeast chromosome. A reported may be selected from the group consisting of enhanced green fluorescent protein, yeast enhanced green fluorescent protein, Aequorea coerelescens green fluorescent protein, DsRed monomer, DsRed2, DsRed express, RedStar2, ASRed2, HcRed1, AmCyan1, ZsYellow1, ZsGreen1, and/or AmCyan1, insect luciferase, bacterial luciferase, bacterial bioluminescence, Renilla luciferase, uroporphyrinogen III methyltransferase, secreted alkaline phosphatase, β-galactosidase, β-glucuronidase, an ice nucleation protein or combinations thereof.

A yeast biosensor that is sensitive to both an organophosphate and an organophosphate hydrolytic product may be prepared by (a) identifying a yeast gene that is upregulated by an organophosphate, (b) identifying at least one expression control sequence of the identified organophosphate-sensitive gene, (c) operably linking a nucleic acid comprising the organophosphate expression control sequence to a nucleic acid encoding a reporter, (d) contacting the operably linked organophosphate nucleic acids with a cell under conditions that permit uptake of the nucleic acids, (e) identifying a yeast gene that is upregulated by an organophosphate hydrolytic product and/or by a process of organophosphate hydrolysis, (f) identifying at least one expression control sequence of the identified organophosphate hydrolysis-sensitive gene, (g) operably linking a nucleic acid comprising the organophosphate hydrolytic product expression control sequence to a nucleic acid encoding a reporter, and (h) contacting the operably linked organophosphate hydrolytic product nucleic acids with a cell under conditions that permit uptake of the nucleic acids. The operably linked organophosphate nucleic acids and/or the operably linked organophosphate hydrolytic product nucleic acids may be comprised in one or more plasmids or integrated into a yeast chromosome. An expression control sequence may include a promoter. In some embodiments, and expression control sequence may include nucleotides −500 to −1 of the identified gene. A reported may be selected from the group consisting of enhanced green fluorescent protein, yeast enhanced green fluorescent protein, Aequorea coerelescens green fluorescent protein, DsRed monomer, DsRed2, DsRed express, RedStar2, ASRed2, HcRed1, AmCyan1, ZsYellow1, ZsGreen1, and/or AmCyan1, insect luciferase, bacterial luciferase, bacterial bioluminescence, Renilla luciferase, uroporphyrinogen III methyltransferase, secreted alkaline phosphatase, β-galactosidase, β-glucuronidase, an ice nucleation protein or combinations thereof.

BRIEF DESCRIPTION OF THE DRAWINGS

Some specific example embodiments of the disclosure may be understood by referring, in part, to the following description and the accompanying drawings, wherein:

FIG. 4A illustrates a DNA sequence of a yeast codon-optimized opd gene (SEQ ID NO:1);

FIG. 4B illustrates a DNA sequence of a yeast codon-optimized DsRed express gene (SEQ ID NO:2);

FIG. 15A illustrates a DNA sequence of YGR035C-F1-YeGFP (SEQ ID NO:3);

FIG. 15B illustrates a DNA sequence of pYLR346C-F1-YeGFP (SEQ ID NO:4);

FIG. 18A illustrates a DNA sequence of pYGR287C-F1-YDsRed (SEQ ID NO:5);

FIG. 18B illustrates a DNA sequence of pPDX1-F1-YDsRed (SEQ ID NO:6);

FIG. 21A is a depiction of wild-type OPH and variant OPH amino acid sequences according to some embodiments of the disclosure (Bold/LARGE type in the variant OPH sequences represent amino acid changes to the 'wild-type' lacZ-OPD fusion described in Mulbry and Karns, 1989);

FIG. 21B is a depiction of wild-type OPH and variant OPH amino acid sequences according to some embodiments of the disclosure (Bold/LARGE type in the variant OPH sequences represent amino acid changes to the 'wild-type' lacZ-OPD fusion described in Mulbry and Karns, 1989);

DETAILED DESCRIPTION

Figure 1:
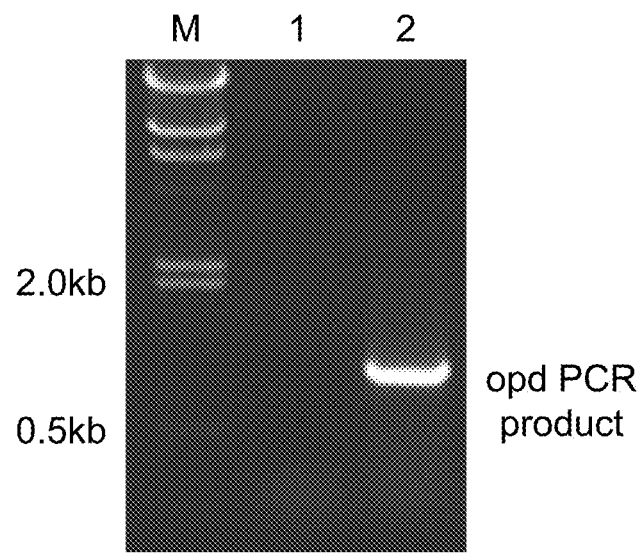
FIG. 1 is an image of a gel illustrating PCR amplification of the opd gene (M, λHindIII DNA marker; lane 1, negative PCR control; lane 2, opd PCR product)
Figure 2:
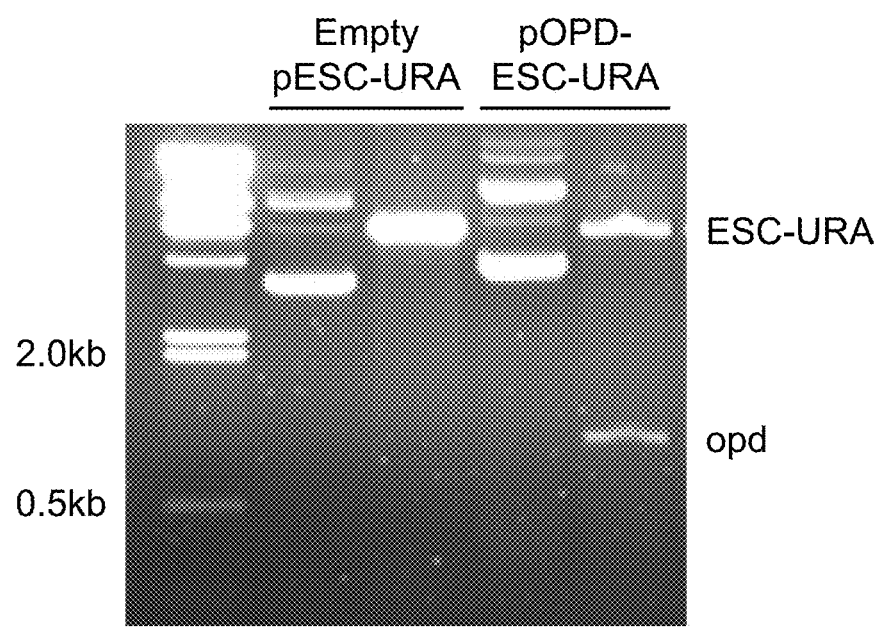
FIG. 2 is an image of a gel illustrating a diagnostic restriction digest (HindIII/BamHI) of pOPD-ESC-URA, which produced the fragments 1031 and 6554 bp (far right lane), to confirm cloning the opd gene into the yeast pESC-URA plasmid.
Figure 3:
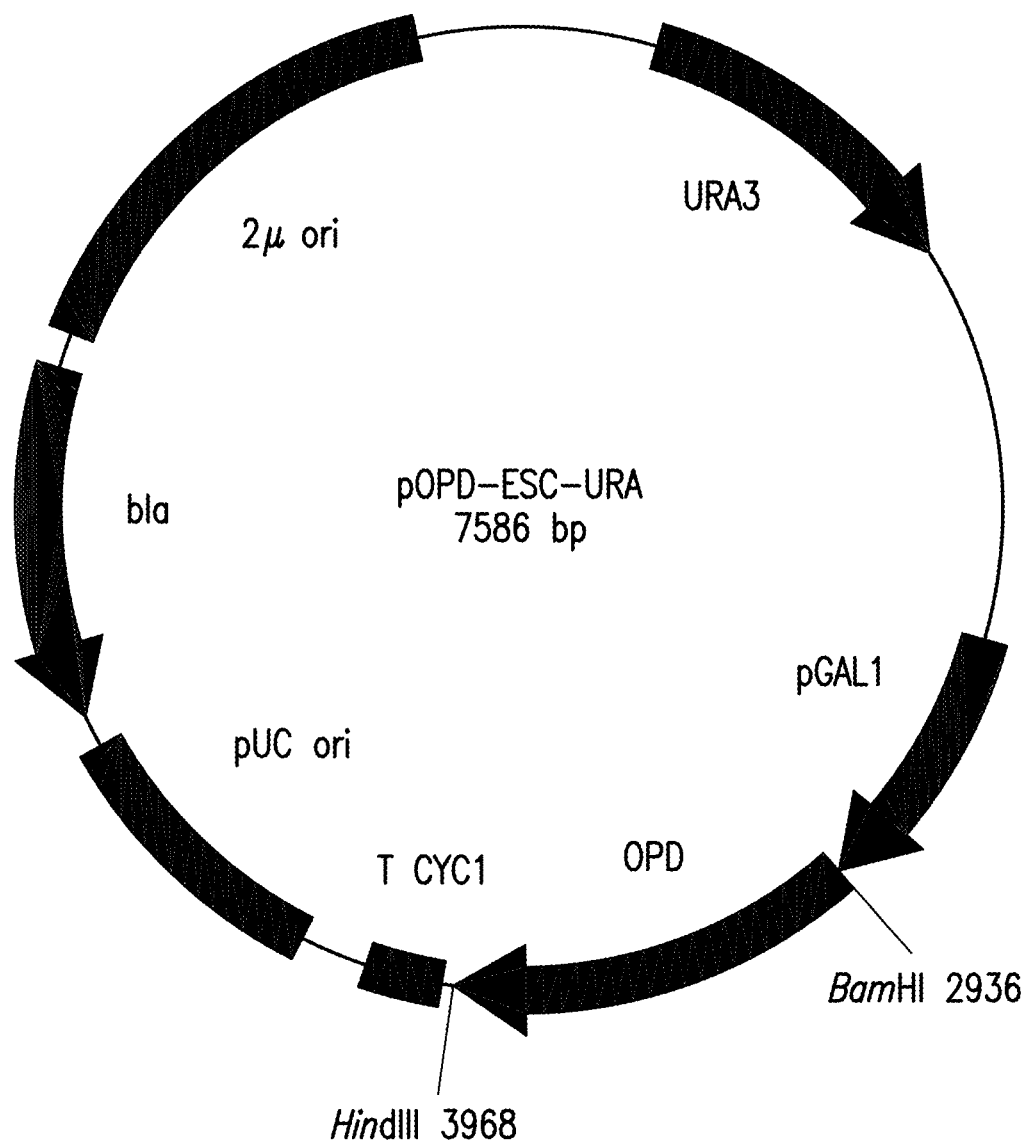
FIG. 3 is a sketch of a yeast opd expression plasmid having the yeast 2μ origin for plasmid replication, the URA3 auxotrophic marker for yeast transformant selection, the yeast pGAL1 promoter for regulated expression, the bacterial opd gene, and the yeast TCYC1 terminator for transcriptional termination.
Figure 5:
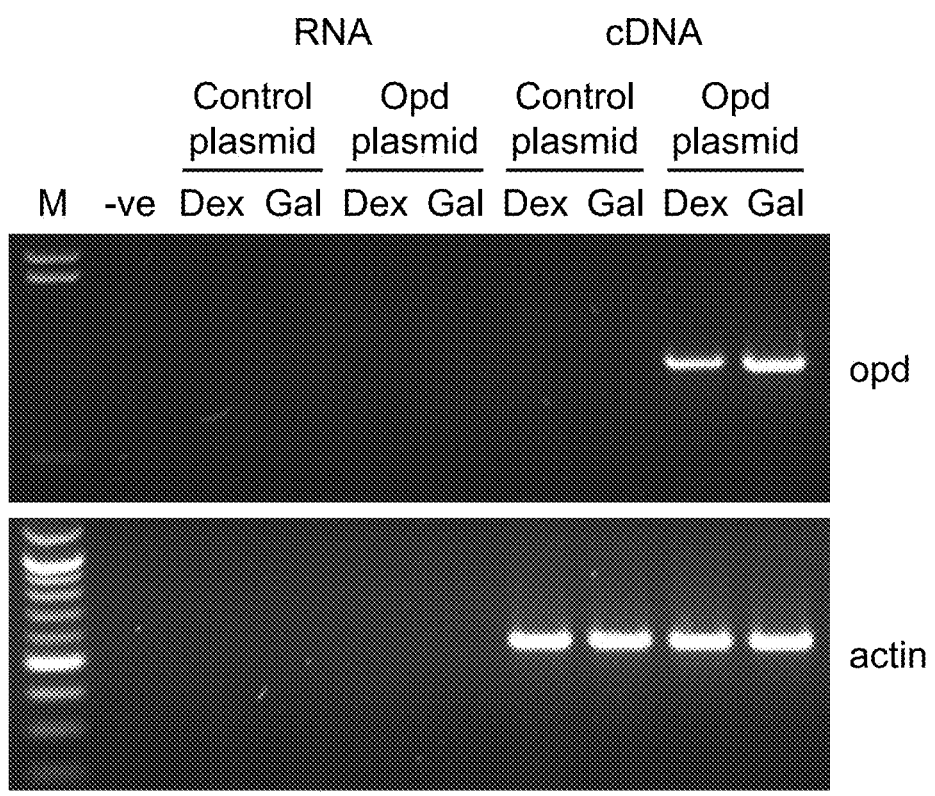
FIG. 5 is an image of gels illustrating yeast transformants expressing opd, wherein (i) pESC-URA (control plasmid) and pOPD-ESC-URA were transformed into S. cerevisiae W3031A, (ii) RNA was prepared, (iii) RT-PCR was used to examine opd mRNA expression, and (iv) actin was used as an internal loading control (Dex, dextrose; Gal, galactose)

Current methodologies for the detection of nerve gas agents include ion mobility spectrometry, electrochemical sensors, gas/liquid chromatography, mass spectrometry, infrared spectroscopy, photo ionization detectors, surface acoustic wave sensors, and color-change chemistry. These methods may be generally laborious, and may require expensive laboratory equipment and complicated methodology. Methods used for the hydrolysis of nerve gases and OP pesticides include chemical and enzymatic hydrolysis using naturally occurring enzymes derived from bacteria, mammals, squid, clams, and protozoa. Drawbacks of using a purified enzyme may include a need for tedious and/or expensive isolation/preparation methods and instability of the purified enzyme.

In some embodiments, a biosensor may include a microbe (e.g., a bacteria or a yeast). For example, a whole cell bacterial biocatalyst heterologously expressing the opd (organophosphate degrading) gene may be prepared that hydrolyzes organophopshate compounds. In some cases, attention may be given to the cellular location of the enzyme since this may influence reaction rates. For example, OPH expressed on the cell surface may more effectively hydrolyze OP compounds than whole cell biocatalysts where OPH resides within the cytoplasm. Without limiting any embodiment of the disclosure to any particular mechanism of action, this may relate to the permeability barrier function of the bacterial cell envelope. Permeabolizing the outer membrane using solvents, freeze/thaw methods, and/or using outer membrane permeable mutants may, in some embodiments, reduce these issues and increase the rate of passive diffusion and hydrolysis rates.

In some embodiments, a yeast biosensor may include a dual reporter system capable of detecting (a) an organophosphate compound and (b) hydrolysis of the organophosphate, for example, by detecting a degradation product of the organophosphate. A yeast biosensor may further include a biochemical system for degrading an organophosphate compound. Yeast may be genetically engineered to be able to biodegrade chemical agent contamination by expressing heterologous enzymes that biodegrade these agents, and also be engineered to detect the chemical agents and its biodegraded products using differentially inducible promoter/fluorescent protein fusions. According to some embodiments, the ability to modify, degrade, and/or detoxify a chemical agent may provide the sensor with a self-clearing or auto-reset feature. In other embodiments, this ability may allow a biosensor to be used not only to detect a chemical agent, but also to clear that agent from a space.

The yeast, *S. cerevisiae*, may be used in some embodiments of the disclosure because (i) it is resistant to environmental extremes; (ii) it is genetically well defined with a plethora of mutants available through the *Saccharomyces* Genome Deletion Project (Stanford); (iii) it may be been used for the expression of heterologous proteins including the organophosphoric acid anhydrolase encoding gene; (iv) it is non-pathogenic; (v) it is readily lyophilized and has good survival rates after 10 years of storage, and/or (vi) yeast genotoxic-inducible genes respond to a broader spectrum of damaging agents than some bacteria. This may be important for the identification of genes, which may be induced by different OP agents.

In some embodiments, a biosensor may benefit from the relatively rapid doubling time of bacteria (e.g., 20 minutes compared to 70 minutes for yeast). In other embodiments, slower growth is tolerated in view of, for example, the ability of large substrates to enter the yeast cell such as OP pesticides (e.g. azinphos-methyl, diazinone, dimethoate, pirimiphos-methyl) and the availability of specific mutants to increase substrate permeability. In addition, yeast biosensor production may occur in a laboratory where time is not a major constraint.

In a specific embodiment, the *Flavobacterium* sp./*Pseudomonas diminuta* OPH encoding gene may be heterologously expressed in *S. cerevisiae* to create a yeast biocatalyst capable of hydrolyzing one or more OP compounds, such as VX or the VX model simulant, paraoxon. To maximize substrate entry into the cell, a *S. cerevisiae* cell wall mutant strain, which exhibits increased porosity and allows the passive diffusion of large molecules, may be used. For example, the mutant strain (MATa his3D1 leu2DO met15DO ura3DO DSMI1) (ATCC4005882) has been deleted for SMI1 (also known as KNR4), a gene involved in (1,3)-β-glucan synthesis and chitin synthase expression, which are major components of the yeast cell wall. The SMI1 deletion results in a reduction in overall (1,3)-β-glucan content, a reduction in (1,3)-β-glucan synthase activity, and an increase in cell wall chitin content. The mutant is more sensitive to SDS, suggesting that the cell wall has become weakened. Cell permeability assays have shown that the mutant is more permeable to substrates than the wild-type strain. The ability of a yeast biocatalyst to hydrolyze OP compounds may be tested using VX or a VX simulant such as paraoxon.

A rate-limiting step in the hydrolysis of substrates using whole cell bacterial biocatalysts may be entry of the compound into the cell. Accordingly, the efficiency of bacterial catalysts may be significantly improved by the use of permeable mutants which allow the substrate to more efficiently enter the cell via passive diffusion. Although OP substrates can enter yeast by non-specific mechanisms, a yeast mutant that displays increased permeability may be used. The *Saccharomyces* genome deletion project, which has successfully deleted 95% of the 6,200 open reading frames (ORFs), has provided a wealth of information to the researcher. If required, other yeast mutant strains may be readily available and may be analyzed for the ability of OP substrates to gain entry into the cell.

Preliminary results indicated that intact yeast cells are able to act as intact biocatalysts and hydrolyze the model substrate paraoxon. Nevertheless, some specific experiments indicated that the yeast cell membrane limited paraoxon entry and therefore acted as a permeability barrier. Treatment of yeast cells with a permeabolization agent such as digitonin increased yeast paraoxon hydrolysis 3 to 4-fold. This suggested that disrupting the yeast cell membrane increased the rate of paraoxon into the cell and thereby increased yeast biocatalytic activity. In addition, an erg6 mutant, which has a specific defect in ergosterol (membrane) biosynthesis, was hypersensitive to paraoxon. This suggests that membrane defects increase substrate permeability and alters the rate of paraoxon entry. Therefore, in some embodiments, yeast mutants such as those that harbor mutations in ergosterol biosynthesis such as the erg6 mutation may be used to increase membrane permeability to different substrates (Gaber R F et al., (1989) Mol Cell Biol 9, 3447-56; Hemenway C S & Heitman J (1996) J Biol Chem 271, 18527-34). In another embodiment, the yeast (or host species of choice) may be specifically engineered to express an active OP/chemical agent membrane transporter to actively uptake the chemical agent in order to increase the concentration of the chemical agent inside the cell.

The interaction of OPH with the OP substrate may also be influenced by the rate of active export of the agent, which is mediated by specific efflux pumps. For example, 22 yeast genes encoding putative ABC transporter proteins, which are involved in the active efflux of a wide range of drugs and compounds, have been identified (Rogers B et al., (2001) J Mol Microbiol Biotechnol 3, 201-214). The three major transporters are PDR5 (pleiotropic drug resistance), YOR1 (yeast oligomycin resistance) and SNQ2 (sensitivity to 4-nitroquinolin-N-oxide). In some embodiments, a yeast biosensor may include a drug efflux mutation alone or in combination with a yeast permeability mutation(s) and/or a mutation(s) that increases sensitivity of the cell to the chemical agent, for example, to increase the interaction of the substrate with intracellular enzyme.

An OPH enzyme may be secreted or presented at the cell surface to bypass a substrate entry and/or efflux limitation according to some embodiments. A similar strategy has been employed for bacterial whole cell catalysts. Fusion of the OPH enzyme to the ice-nucleation protein was shown to target the OPH enzyme to the cell surface where it was displayed and efficiently hydrolyzed OP agents (Mulchandani A et al., (1999) Biotechnol Bioeng 63, 216-23; Shimazu M et al., (2003) Biotechnol Prog 19, 1612-4; Mulchandani P et al., (2001) Biosens Bioelectron 16, 433-7). Protein secretion in yeast may be mediated by fusion of a synthetic leader peptide, which contains the necessary signals to direct the protein through the secretory pathway (Parekh R et al., (1995) Protein Expr Purif 6, 537-45). Fusion of the leader peptide to the bovine pancreatic trypsin inhibitor (BPTI) enabled secretion of 140 μg/ml of active BPTI (Parekh R N et al., (1996) Biotechnol Prog 12, 16-21). Likewise, in some embodiments, the OPH enzyme may include a leader peptide with secretory pathway signals. Export of the OPH enzyme may be desired where a yeast is less permeable to a parent compound than one or more hydrolytic products of the parent compound.

While rates of hydrolysis by OPH may vary, in some embodiments, enzymes that exhibit higher catalytic activity towards different chemical agents may be used. In addition, different formulations of yeast biocatalysts may be combined each expressing different forms of the OPH enzyme to provide optimal substrate specificity for the particular OP target.

In some embodiments, *S. cerevisiae* genes transcriptionally induced by VX (or paraoxon) and genes, which are induced by the hydrolysis products may be identified. For example, global transcription profiling (microarray analysis) may be performed on *S. cerevisiae* SMI1 in the presence or absence of a chemical agent such as VX and on recombinant *S. cerevisiae* SMI1 expressing OPH in the presence or absence of VX. The comparison between wild-type cells incubated with VX, and recombinant cells expressing OPH incubated with VX, may facilitate identification of one or more yeast genes induced by the hydrolysis of VX. Hydrolysis of VX using a yeast strain expressing OPH may result in a transcriptional profile that is distinct from cells lacking the ability to hydrolyze VX. Real-time RT-PCR may then be used on prioritized targets using different concentrations of VX to identify yeast genes that are induced at low concentrations and in a dose-dependent manner.

Promoter regions of prioritized genes may be mapped using the *Saccharomyces* promoter database (SCPD) (maintained by Cold Spring Harbor Laboratories, Cold Spring Harbor, N.Y.), literature analysis, and/or 5' promoter analysis. Such mapping may aid identification of one or more promoter regions that confer sensitivity to VX, VX hydrolytic products, and/or a process of VX hydrolysis. Promoters may be cloned, fused to enhanced green fluorescent protein (EGFP) or DsRed express (Clontech), which exhibit distinct spectral properties, to create a dual reporter yeast biosensor that differentially fluoresces during VX contamination detection and biodegradation. In some embodiments, single promoter-reporter fusions may successfully detect genotoxic agents. In other embodiments, a signature of promoter-reporter fusions may be required to differentiate OP agents.

In some embodiments, a detection system may include a bioluminescence component (e.g., luxAB). Bioluminescence may be a transient signal. For example, LuxAB proteins may be sensitive to elevated temperature (30° C.) and may also require additional substrates for activity. In some embodiments, a detection system may include a fluorescence component (e.g., a fluorescent protein). Fluorescent proteins for use in a detection system may be stable and may have one or more of a variety of spectral properties. A biosensor, according to some embodiment, may be configured with a detection system (e.g., fluorescence) suitable for use outside of the laboratory under harsh conditions.

In some embodiments, a biosensor may be self-contained, may require no exogenous substrates and/or consumables, may be inexpensive to produce in bulk quantities, and/or may be visually identified using a simple hand-held illumination device.

In some embodiments, a biosensor may be used for the detection and biodegradation of organophosphate nerve agents and pesticides such as VX, soman, sarin, demeton S, paraoxon, tabun, DFP, acephate, chlorpyrifos, coumaphos, coroxon, parathion, diazinon, and dMUP.

However, by changing an enzyme's substrate specificity by using mutant enzymes (by error prone PCR or by directed evolution such as DNA shuffling) or natural enzymes which are capable of biodegrading different chemical agents, embodiments of the disclosure may be used to achieve broader specificity to detect and biodegrade other targets such as H-class agents (e.g., mustard gas).

OPH hydrolyzes, and thereby reduces the toxicity of a wide variety of OP pesticides and chemical warfare agents by cleaving the P—O, P—F, and P—S containing bonds; however, OPH cleaves these bonds with different efficiencies. For example, OPH catalyses: the P—O bond of paraoxon, parathion, and coumaphos with $k_{cats}$ of 67-5,000 s$^{-1}$; the P—F bond of diisopropyl fluorophosphate (DFP), sarin, and soman with $k_{cats}$ of 0.01-500 s$^{-1}$; and the P—S bond of VX, demeton-S, malathion, and acephate with $k_{cats}$ of 0.0067-167 s$^{-1}$. Therefore, the hydrolytic efficiency of OPH towards P—S bonds is lower; VX, for example, is cleaved at an efficiency which is 1000-fold less than paraoxon. In order to improve the catalytic efficiency and specificity of OPH, OPH variants have been generated by designed and random approaches (Watkins L M et al., (1997) J Biol Chem 272, 25596-601; Yang H et al., (2003) Protein Eng 16, 135-45; Cho C M et al., (2002) Appl Environ Microbiol 68, 2026-30; Chen-Goodspeed M et al., (2001) Biochemistry 40, 1325-31). Both approaches rely on mutagenesis of the opd gene followed by screening against the target of choice in order to optimize the mutant enzyme for the specific target. These studies have shown that the efficiency of the reaction can be increased by 3 orders of magnitude using 'difficult to cleave' substrates (Hill C M et al., (2003) J Am Chem Soc 125, 8990-1; Cho C M et al., (2004) Appl Environ Microbiol 70, 4681-5). Moreover, the hydrolytic activities of the variants were comparable to those obtained with the most efficiently hydrolyzed substrate paraoxon. This indicates that by rational and random changes in the OPH sequence, efficient enzymes can be generated that target poorly hydrolyzed substrates.

Intact recombinant OPH$^+$ yeast cells may hydrolyze paraoxon. In some embodiments, in order to improve the efficiency of the OPH enzyme, designed and randomized mutagenesis of OPH may be performed. For example, by screening a combination of designed and random amino acid changes in the enzyme active site, followed by random directed evolution (DNA shuffling) against specific organophosphates, OPH variants may be isolated with significantly improved catalytic efficiency towards the OP agent. Three dimensional structure analysis of OPH using a broad substrate analog has identified three distinct binding pockets within the active site of the enzyme; these binding sites have been termed the small subsite (defined by the side chains of Gly-60, Ile-106, Leu-303, Ser-308, Cys-59, and Ser-61), the large subsite (His-254, His-257, Leu-271, and Met-317) and the leaving group subsite (Trp-131, Phe-132, Phe-306, and Tyr-309) (Vanhooke J L et al., (1996) Biochemistry 35, 6020-5). Amino acid changes in these subsites dramatically alter the stereoselectivity and reactivity of OPH (Chen-Goodspeed M et al., (2001) Biochemistry 40, 1325-31). For example, randomization of amino acid residues in the active site (Ile-106, Try-131, Phe-132, Ser-308 and Tyr-309) increased OPH activity against the already efficiently hydrolyzed substrate paraoxon by 63-fold (Griffiths A D & Tawfik D S (2003) Embo J 22, 24-35). Similarly, Hill et al. (Hill C M et al., (2003) J Am Chem Soc 125, 8990-1) increased OPH catalytic activity against a soman analog by three orders of magnitude simply by changing 3 amino acids (His-254, His-257 and Leu-303 to glycine, tryptophan, and threonine, respectively). The latter studies relied on random changes in the amino acids followed by global screening against the OP substrate of choice.

Directed evolution or DNA shuffling may also be used to screen the entire protein sequence to find an enzyme with increased fitness (Stemmer WP (1994) Proc Natl Acad Sci 91, 10747-51; Stemmer WP (1994) Nature 370, 389-91). This process of recombination and mutation, performed by random fragmentation of a pool of single or related genes, followed by reassembly of the fragments by primerless PCR, has improved the activities of green fluorescence protein, β-galactosidase, and β-lactamase by 45-, 1,000- and 32.000-fold, respectively (Zhang J H et al., (1997) Proc Natl Acad Sci 94, 4504-9; Crameri A et al., (1996) Nat Biotechnol 14, 315-9). DNA shuffling has also proven to be successful in increasing the catalytic activity of OPH (Yang H et al., (2003) Protein Eng 16, 135-45; Cho C M et al., (2002) Appl Environ Microbiol 68, 2026-30). In particular, DNA shuffling against the pesticide chloropyrifos, which is hydrolyzed by the wild-type enzyme almost 1000-fold slower than the preferred substrate paraoxon, resulted in a 725-fold increase in the $k_{cat}/K_m$ value (Cho C M et al., (2004) Appl Environ Microbiol 70, 4681-5).

In some embodiments, the *Flavobacterium* spp. opd gene may be shuffled with a related gene encoding an organophosphorus hydrolase or similar hydrolyzing enzyme from a different species. For example, the *Flavobacterium* spp. opd gene may be shuffled with a closely related *Agrobacterium radiobacter* opdA gene (Horne I et al., (2002) Appl Environ Microbiol 68, 3371-6) to 'accelerate' directed evolution. Shuffling of closely related genes can increase the potential of improved variants compared to shuffling of a single gene (Crameri A et al., (1998) Nature 391, 288-91). The opdA gene is approximately 88% identical to opd at the nucleotide level and the encoded enzyme has been shown to have a broader substrate range and superior kinetics for some substrates (notably demeton-S) than opd.

According to some embodiments, an efficient yeast biocatalyst/biosensor may function outside a laboratory. In some of these embodiments, a biosensor may: (i) use optimal expression signals in order to achieve high level expression; (ii) integrate multiple copies of the opd gene/reporter genes into the yeast genome which, in turn, lead to greater expression, and/or (iii) stably maintains the opd gene/reporter genes even in the absence of selective pressure. The Examples of the disclosure relate to episomal expression of the OPH protein and the fluorescent reporter plasmids from a yeast 2μ plasmid. This strategy may provide a simplistic and common approach for the heterologous expression of foreign genes. The 2μ plasmid may have low segregational stability, i.e., the plasmid may not be stably maintained in a yeast population (Murray A W & Szostak J W (1983) Cell 34, 961-70). This may result in a heterogeneous yeast population even under selective pressure. For example, preliminary results indicated that only approximately 25% of yeast cells stably maintained the OPH expression vector under selective pressure. This means that most of the yeast cells did not contain the OPH plasmid and therefore, may have been operating under suboptimal conditions.

Episomal plasmid instability may be overcome, in some embodiments, by integrating the plasmid/gene of interest into the yeast genome. This results in a stable, clonal yeast population that maintains the inserted DNA sequence for many generations even in the absence of selective pressure (Lopes T S et al., (1989) Gene 79, 199-206; Parekh R N et al., (1996) Biotechnol Prog 12, 16-21). Integrated sequences may be maintained at a lower copy number (1-5) compared to episomal plasmids (30-50) (Orr-Weaver T L & Szostak J W (1983) Mol Cell Biol 3, 747-9); however, since the number of integrated copies is proportional to the number of target sites in the yeast genome (Wilson J H et al., (1994) Proc Natl Acad Sci 91, 177-81), yeast cells carrying multiple copies of the integrated DNA may be generated when the insertion sequence is present in multiple copies. For example, ribosomal DNA (rDNA) encompasses about 140 copies of a 9.1 kb unit repeated in tandem on chromosome XII (Petes T D (1979) Proc Natl Acad Sci 76, 410-4). By targeting the rDNA locus, phosphoglycerate kinase (PGK) was integrated at 100-200 copies per cell, and when expressed from the glyceraldehydes-3-phosphate dehydrogenase (GAPDH) promoter, represented approximately 50% of the total soluble protein. Similarly, by targeting the Ty 6 sequences for homologous recombination, which are present at about 150-200 copies per cell, up to 30 copies of the integrated sequence may be obtained. In comparison to using 2μ plasmids, 2 to 10-fold increases in protein expression may be achieved. Therefore, in some embodiments, the opd gene/reporter genes may be integrated into the yeast genome to create a stable yeast biocatalyst/biosensor.

The opd gene, which was originally derived from the bacterium *Flavobacterium* spp., may contain codons that are rarely used in yeast (or the specific host strain) or contain expression-limiting regulatory elements within the coding sequence. In some embodiments, the OPH encoding opd gene, may be codon optimized to ensure efficient expression in yeast/the particular host species. The reporter genes may also be modified to ensure optimal codon recognition and to remove expression limiting regulatory elements to ensure efficient expression in the host species of choice. (For example, the sequences of the codon optimized opd and YDsRed genes are provided in FIGS. 4A and 4B).

A pGAL regulatable promoter was used in Examples of the disclosure to drive expression of the foreign opd gene since expression could be repressed or induced by the presence of dextrose or galactose, respectively. However, a promoter that is constitutively and strongly expressed may be used to express of opd gene. For example, the glyceraldehyde phosphate dehydrogenase (GAPDH) promoter is routinely used to achieve high level, foreign gene expression in *S. cerevisiae* since it is both strongly and constitutively expressed (Edens L et al., (1984) Cell 37, 629-33; Imamura T et al., (1987) J Virol 61, 3543-9). Therefore, in some embodiments, the GAPDH promoter or a similarly highly expressed constitutive promoter may be used to drive foreign gene expression in yeast. For example, the GAPDH promoter may be operably linked (e.g., positioned adjacent to) the opd gene such that the opd gene is constitutively expressed.

Microarray analysis may be used in some embodiments to identify genes that are sensitive to paraoxon and the paraoxon hydrolysis products. As illustrated by the Examples of the disclosure, microarray analysis identified approximately 1900 paraoxon-inducible genes and genes which were associated with paraoxon hydrolysis. Therefore, microarray analysis may be used to identify genes and the corresponding promoters that are sensitive to other organophosphates or other chemical agents. Microarray analysis may also be used to identify genes and the corresponding promoters that are sensitive to the degradation products of the other organophosphates or chemical agents.

Global transcription profiling (microarray analysis) may be performed on wild-type *S. cerevisiae* (or the species of choice) in the presence or absence of the chemical agent, and on recombinant *S. cerevisiae* expressing an enzyme/metabolizing agent that may hydrolyze the chemical agent in the presence or absence of the chemical agent. In another embodiment, an alternative approach for identifying genes which are induced by the hydrolysis of the chemical agent is to incubate the cells directly with the hydrolysis products rather than relying on cells to hydrolyze the agent. For example, enzymatic hydrolysis of the OP nerve agent VX produces 2-(diisopropyl)aminoethanethiol (Bonierbale E et al., (1997) J Chromatogr B Biomed Sci Appl 688, 255-64; Joshi K A et al., (2006) Anal Chem 78, 331-6). Microarray analysis may be performed using RNA prepared from cells incubated in the presence of 2-(diisopropyl)aminoethanethiol hydrochloride.

A similar approach may be used, in some embodiments, to identify genes which are transiently-induced by the hydrolyzed products. Transiently-induced genes may be desirable to allow the progress of a decontamination process to be monitored. Cells may be exposed to the hydrolyzed products for 60 min, divided equally, and either used for RNA preparations, or washed, and resuspended in medium lacking the hydrolyzed products. Genes, which are initially induced by the metabolites, but subsequently return to the basal uninduced level, are transiently-induced genes.

In another embodiment, 'light' (bioluminescent) genes which emit light at distinct, different wavelengths may be used as the reporter signal. For example, the *Vibrio harveyi* luxAB genes may be used in yeast (Szittner R et al., (2003) Biochem Biophys Res Commun 309, 66-70). LuxAB-yeast cells are viable in the presence of 0.5% Z-9 tetradecenal and produce a bioluminescent signal similar to that obtained with n-decanal. Moreover, the bioluminescent signal remains strong for 24 h without further addition of the aldehyde substrate. Coexpression of the oxidoreductase *Vibrio harveyi* gene (frp) which encodes for the limiting substrate $FMNH_2$, further enhanced the bioluminescent signal to levels comparable to prokaryotic systems. These experiments resulted in a bioluminescent signal approaching $9\times10^5$-fold above background levels (Gupta R K et al., (2003) Fems Yeast Res 4, 305-13). A 'transient' luminescent signal may permit temporal monitoring of the decontamination process.

A potential disadvantage of luminescence is the thermal instability at elevated temperatures (Escher A et al., (1989) Proc Natl Acad Sci 86, 6528-32). However, the thermally stable LuxAB from *Xenorhadbus luminescens* may be used if required or desired. Luciferase activity from *X. luminescens* displays a high thermal stability (half life of 3 h at 45° C.) and may be the bioluminescent system of choice for biosensors used at higher temperatures. In addition, a 'signature' of promoters fused to different luciferases with different emission colors (Lin L Y et al., (2004) Biochemistry 43, 3183-94) may be used to monitor the decontamination process over an extended period of time.

In another embodiment, rather than biodegrading the chemical agent and directly reducing the toxicity of the chemical agent, the biocatalyst may modify the chemical agent to render it more susceptible to chemical hydrolysis.

In another embodiment, the biocatalyst may harbor multiple biodegrading enzymes and multiple promoter reporter gene fusions in order to detect and biodegrade different chemical agents.

In another embodiment, clonal cells, each harboring a specific biodegrading enzyme and specific reporter detection system for a specific chemical, may be mixed into a heterogeneous population that as a group, can detect and biodegrade different chemical agents.

In another embodiment, the chemical agent may be hydrolyzed or biodegraded using a molecule with hydrolyzing capability (other than an enzyme) such as a deoxyribonucleic acid (e.g., DNAzyme) or ribonucleic acid, or similar which can be produced in a living cell.

As will be understood by those skilled in the art, other equivalent or alternative systems, devices, and methods for detecting and/or modifying chemical agents, according to embodiments of the present disclosure can be envisioned without departing from the essential characteristics thereof. For example, devices of the disclosure may be manufactured in either a handheld or a tabletop configuration, and may be operated sporadically, intermittently, and/or continuously. In addition, a biosensor may be configured for use under one or more temperatures and/or pressures. Moreover, individuals of ordinary skill in the art would recognize that there a number of autologous and heterologous nucleic acids may be used to detect and/or modify a target chemical. Also, the disclosure is not limited to any particular light sources and/or light emission optics, but broadly contemplates the use of any type of emitter that may be appropriately tuned to the desired wavelength(s). Similarly, the disclosure contemplates the use of any type of light detector and/or light detection optics. All or part of a system of the disclosure may be configured to be disposable and/or reusable. From time to time, it may be desirable to clean, repair, and/or refurbish a reusable component. Moreover, one of ordinary skill in the art will appreciate that no embodiment, use, and/or advantage is intended to universally control or exclude other embodiments, uses, and/or advantages. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

In some embodiments, an OP may be biodegraded using an OPH variant. A variant OPH may comprise an amino acid sequence that is the same as (e.g. 100% identity) a wild-type OPH sequence (e.g., GenBank Accession No. M29593 from *Flavobacterium* spp. or SEQ ID NO:68, a lacZ-OPD fusion from plasmid pJK33) except for one or more substitutions at C59, G60, S61, A80, I106, W131, F132, K185, D208, H254, H257, L271, L303, F306, S308, Y309, and/or M317 (numbering according to GenBank Accession No. M29593; SEQ ID NO:84) (nucleic acid sequence, SEQ ID NO:83). For example, a variant may comprise a substitution selected from G60V, A80V, I106V, F132D, K185R, D208G, H257W, I274N, F306V, S308L, and/or R319S. In some embodiments, an OPH variant may include a wild-type OPH sequence with combination of two or more of these substitutions. For example, a variant may comprise:

(1) A80V.K185R.D208G.I274N.R319S (SEQ ID NO:69), (2) A80V.K185R.D208G.H257W.I274N.R319S (SEQ ID NO:70), (3) A80V.F132D.K185R.D208G.H257W.I274N.R319S (SEQ ID NO:71), (4) A80V.F132C.K185R.D208G.H257W.I274N.R319S (SEQ ID NO:72), (5) A80V.I106V.F132D.K185R.D208G.H257W.I274N.R319S (SEQ ID NO:73), (6) G60V.A80V.I106V.F132D.K185R.D208G.H257W.I274N.R319S (SEQ ID NO:74), (7) G60V.A80V.I106V.F132D.K185R.D208G.H257W.I274N.F306V.R319S (SEQ ID NO:75), and/or (8) A80V.I106V.F132D.K185R.D208G.H257W.I274N.S308L.R319S (SEQ ID NO:76).

According to some embodiments, an OPH variant may comprise an amino acid sequence that is from about 95% to about 100% identical to a wild-type sequence. Sites of non-identity to a wild-type sequence may include, for example, C59, G60, S61, A80, I106, W131, F132, K185, D208, H254, H257, L271, L303, F306, S308, and/or Y309. An OPH variant may comprise an amino acid sequence selected from SEQ ID NO:69, SEQ ID NO:70, SEQ ID NO:71, SEQ ID NO:72, SEQ ID NO:73, SEQ ID NO:74, SEQ ID NO:75, SEQ ID NO:76, and/or derivatives thereof. A derivative sequence may have catalytic activity and/or a sequence that is about 95% identical (e.g., ≥95% identity, ≥96% identity, ≥97% identity, ≥98% identity, and/or ≥99% identity) to one or more of SEQ ID NOS:69-76 and/or 78. An OPH variant may be encoded by a nucleic acid sequence comprising SEQ ID NO:77 in some embodiments.

An OPH variant may be used, according to some embodiments, in an OP bioremediation strategy either directly or in the form of a microorganism based biocatalyst. Generation of OPH variants with improved activity and variants with increased solubility, as suggested by the large increases in the specific activities, may facilitate this process. Although OPH may hydrolyze and thereby reduce the toxicity of VX, malathion, and/or demeton-S methyl, the resulting hydrolytic products may still be toxic in some cases. Therefore, according to some embodiments, incorporation of additional enzymes such as the *Enterobacter aerogenes* glycerophosphodiesterase to further hydrolyze the degradation products of VX, may be required and/or desired to facilitate the bioremediation process. For microorganism based biocatalysts, OPH variant enzymes may be restricted to the intracellular environment of the cell or they may be extracellular (e.g., presented at the cell surface and/or secreted).

A variant enzyme (e.g., OPH), according to some embodiments, may be encapsulated or immobilized to improve functionality and/or stability. For example, an enzyme may be encapsulated by coating the enzyme with biocrystals, silica, liposomes, oxide matrices, trehalose, and/or other coatings. In other embodiments, the variant enzymes or microorganism-based biocatalyst may be immobilized onto solid supports such as, but not limited to nylon, polyurethanes, polyethyleneglycol (PEG)-based hydrogels, porous glass, silicone polymers, or silica beads.

In some embodiments, a variant enzyme (e.g., OPH) may be incorporated into a biosensor for detection of an OP pesticide and/or chemical warfare agent. This may be achieved, for example, by developing a strategy to detect an OPH-variant mediated hydrolyzed reaction product (e.g., Examples 1-14).

In other embodiments, a variant enzyme (e.g., OPH) may be fused at the 5' or 3' ends to a peptide, leader sequence, or a secondary protein to increase stability and/or activity of the enzyme.

EXAMPLES

Some embodiments of the disclosure may be illustrated by one or more of the following examples.

Examples 1-9 elaborate construction of a yeast expression vector containing the bacterial opd gene and transformation into *S. cerevisiae*. Reverse transcription-PCR was used to confirm that the opd gene was expressed in yeast. Paraoxonase assays using enzyme lysates prepared from the recombinant OPH+ yeast indicated the opd gene produced functional OPH protein that hydrolyzed paraoxon. Intact whole cell paraoxonase assays indicated that yeast cells could hydrolyze paraoxon and function as a biocatalyst. Yeast colony counting onto selective and non-selective media indicated that the yeast episomal plasmid expressing OPH was not stably maintained by the yeast population. This indicates that for optimal yeast biocatalyst function, the opd gene may be integrated into the yeast genome to create a stable, clonal yeast population. Testing and optimization studies were performed which demonstrated that: (i) disruption of the yeast membrane increased whole cell paraoxon hydrolysis; (ii) pretreatment with low concentrations of ethanol increased whole cell activity, and (iii) the erg6 yeast membrane mutant was hypersensitive to paraoxon, suggesting that an erg6 mutation, increased the rate of paraoxon entry.

Examples 10-12 elaborate identification of *S. cerevisiae* genes transcriptionally induced by paraoxon, a process of paraoxon hydrolysis, and/or products of paraoxon hydrolysis. Microarray analysis was used to identify yeast genes induced by paraoxon and genes which were induced by paraoxon hydrolysis. A large number of paraoxon-inducible genes were identified which were significantly and substantially induced. The paraoxon-inducible genes YLR346C and YGR035C were prioritized for further analysis and quantitative real-time PCR demonstrated that both of these genes were quickly (7.5 min) and sensitively induced by paraoxon. Therefore, YLR346C and YGR035C displayed the desired characteristics for incorporation into the biosensor and were prioritized for Examples 13-14. Microarray analysis also identified 33 genes which were induced at least 2-fold following paraoxon hydrolysis. Real-time PCR verified that 2 of these genes (POX1 and YGR287C) were only induced in OPH+ strains in the presence of paraoxon. Therefore, POX1 and YGR287C were also prioritized for Examples 13-14. The experiments supporting each of these findings are described in the text below.

Examples 13-14 elaborate construction of an example embodiment of a fluorescent yeast biosensor. Yeast codon optimized YeGFP and YDsRed reporter vectors were constructed. Two paraoxon-inducible promoters (YLR346C and pYGR035C) were fused to YeGFP and 2 promoters associated with paraoxon hydrolysis (POX1 and YGR287C) were fused to YDsRed. The yeast biosensor harboring the YLR346C-YeGFP demonstrated up to 5-fold YeGFP induction in the presence of paraoxon. Moreover, the biosensor was quickly induced (2-fold after 15 min exposure) and induced in a dose-dependent manner by paraoxon. Recombinant OPH+ yeast harboring a paraoxon hydrolysis promoter (POX1) fused to YDsRed also displayed induced fluorescence in the presence of paraoxon. YDsRed induction occurred only in yeast strains expressing OPH, indicating induction required both OPH and paraoxon. This suggests that YDsRed induction was strictly associated with paraoxon hydrolysis. YDsRed was induced in a dose-dependent manner by paraoxon suggesting the biosensor responded to the amount of paraoxon hydrolyzed. The experiments supporting each of these findings are described in detail below.

Examples 15-23 elaborate construction of an example embodiment of an an OPH variant with improved hydrolytic efficiency against VX. Site directed mutagenesis, and saturation mutagenesis of active site residues followed by screening against demeton-S methyl and malathion was sequentially performed to identify variants with improved hydrolytic efficiency. The improved variants were then analyzed for their ability to hydrolyze VX.

Examples 24-29 elaborate generation of recombinant yeast biocatalyst that may hydrolyze (decontaminate) organophosphates.

Example 1

Yeast opd Expression Plasmid and opd mRNA Expression in *S. cerevisiae*

A yeast expression plasmid containing the opd gene under the transcriptional control of the yeast GAL1 promoter, and a yeast ribosome binding site was constructed. A yeast codon optimized opd expression plasmid was simultaneously constructed. The opd expression plasmid was transformed into *S. cerevisiae* and transformed yeast cells were tested for their ability to express opd using relative RT-PCR.

A *Flavobacterium* opd gene in plasmid pJK33, a pUC18 construct, was used. The *Flavobacterium* opd gene is identical to the *Pseudomonas putida* opd gene (Mulbry W W & Karns J S., (1989) J Bacteriol 171, 6740-6). A 1 kb opd fragment was PCR-amplified using a proofreading thermostable polymerase (FIG. 1). The 5' primer was designed to incorporate a yeast ribosome binding site to ensure optimal translation initiation (Looman A C & Kuivenhoven J A., (1983) Nuc Acids Res 21, 4268-71). The 5' and 3' primers were also designed to incorporate the restriction endonuclease sites BamHI and HindIII, respectively. The opd gene was directionally cloned into the corresponding sites of the *S. cerevisiae* expression vector pESC-URA (Table 1) using standard molecular biology techniques to create pOPD-ESC-URA. Diagnostic restriction endonuclease digestion (BamHI and HindIII) and agarose gel electrophoresis confirmed a correct clone had been selected (FIG. 2). The sequence of the PCR-amplified opd gene was verified by deoxy dye terminator sequencing. The pOPD-ESC-URA plasmid contained the yeast 2μ origin and the URA3 auxotrophic marker gene for growth and selection in *S. cerevisiae*, the ColE1 origin and β-lactamase gene for growth and selection in *E. coli*, the GAL1 regulatable promoter for repressed (dextrose) or induced (galactose) expression in *S. cerevisiae*, and a transcription terminator (TCYC1) downstream of the opd gene (FIG. 3). A yeast expression plasmid containing a yeast codon optimized opd gene was also constructed. Codon optimization was performed by Bio S&T (Quebec, Canada). The sequence of the codon optimized opd gene is listed in the (FIG. 4A). The codon optimized opd gene was cloned into pESC-URA to create pYOPD-ESC-URA using the same cloning strategy as the wild-type opd gene.

*S. cerevisiae* was transformed (episomal expression) with the control (pESC-URA) and test plasmids (pOPD-ESC-URA) using the LiAc transformation procedure (Ito H et al., (1983) J Bacteriol 153, 163-8); yeast transformants were readily obtained. To verify that opd mRNA was expressed adequately, relative RT-PCR analysis was performed (FIG. 5). Transformants harboring control (pESC-URA) and test (pOPD-ESC-URA) plasmids were grown in synthetic dropout media (SD) under conditions that either repressed (dextrose medium) or induced (galactose medium) expression from the GAL1 promoter. Total RNA was prepared using Tri reagent (Ambion) according to the manufacturers' instructions and treated with DNase1. Equal amounts of RNA (approximately 1 μg) were reverse transcribed into cDNA using the retroscript kit (Ambion). PCR was performed initially with primers designed against the *S. cerevisiae* housekeeping gene actin (ACT1, 547 bp product) to ensure equal amounts of cDNA were used for each sample; if required, the amount of cDNA template was then adjusted accordingly before opd analysis. PCR products were resolved and analyzed using agarose gel electrophoresis. PCR analysis was also performed with samples that lacked reverse transcriptase (RNA samples); no RT-PCR products were detected from these samples as expected. Opd RT-PCR analysis indicated that: (i) RT-PCR products were not detected from transformed yeast cells harboring the control plasmid (as expected); (ii) RT-PCR products were detected from yeast cells harboring pOPD-ESC-URA indicating the yeast cells were transformed successfully and were expressing the opd gene, and (iii) opd expression was higher in conditions that induced expression from the Gal promoter (presence of galactose).

The yeast opd expression plasmid, containing yeast transcriptional and translation signals, was constructed successfully. Transformed yeast cells harboring the yeast opd expression plasmid expressed opd mRNA.

Example 2

Effect of opd Expression on *S. cerevisiae* Growth

Recombinant *S. cerevisiae* W3031A harboring control (pESC-URA) or test (pOPD-ESC-URA) plasmids were grown in SD media lacking uracil under repressed (2% dextrose) or induced (2% galactose) conditions at 37° C. and monitored for growth spectrophotometrically.

Figure 6:
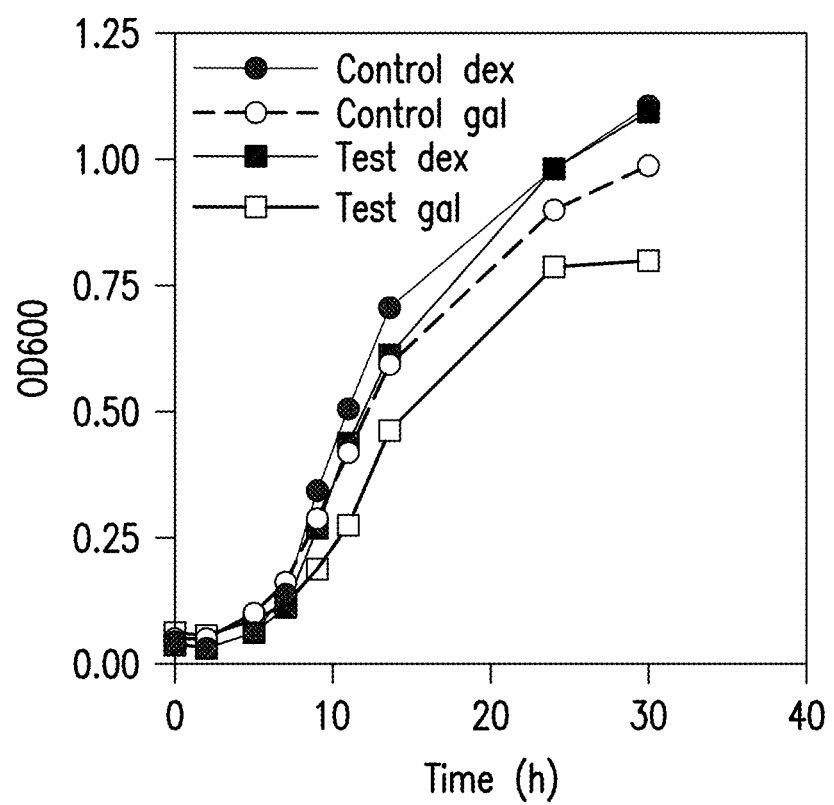
FIG. 6 is a chart illustrating growth (monitored at $A_{600}$) of S. cerevisiae harboring control (pESC-URA) or test (pOPD-ESC-URA) plasmids under repressed (dex, dextrose) or inducing (gal, galactose) conditions.

Both control and test cultures grew slower in minimal media containing galactose compared to dextrose. *S. cerevisiae* harboring the opd plasmid exhibited a slight reduction in growth compared to the 'empty' control plasmid (FIG. 6). This may simply be due to protein over-expression which 'drained' the metabolic activity of the cell, and therefore, reduced the growth rate.

Opd expression is not toxic to *S. cerevisiae*; however, there was a slight inhibition in the growth rate of yeast cells harboring the opd plasmid under inducing conditions.

Example 3

Effect of Paraoxon on *S. cerevisiae* Growth

*S. cerevisiae* was grown overnight in complex YPD broth (yeast extract, peptone, dextrose) or in SD media supplemented with uracil and 2% galactose (SDgal) at 37° C. to stationary phase. At time zero, the culture was divided equally and incubated in the absence or presence of 0.5, 1.0, 2.0, and 4.0 mM paraoxon. Growth was monitored spectrophotometrically at $OD_{600}$.

Figure 7A:
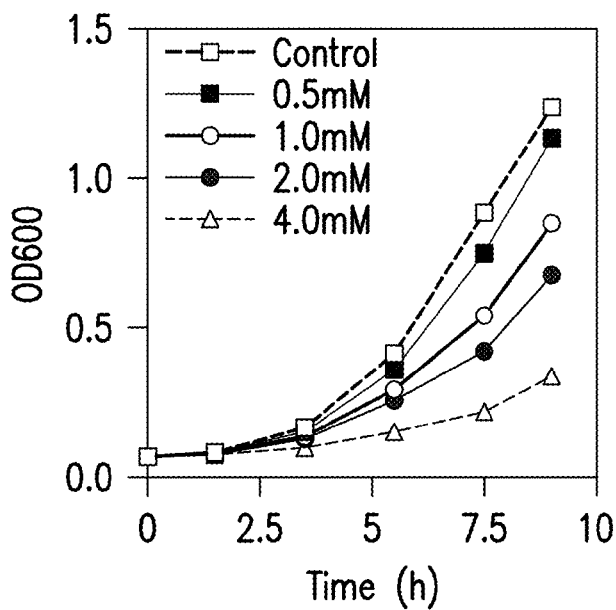
FIG. 7A is a chart illustrating dose-dependent inhibition of S. cerevisiae BY4741 growth (monitored at $A_{600}$) in the presence of paraoxon.

0.5 mM paraoxon did not significantly inhibit the growth of *S. cerevisiae* (FIG. 7A); however, paraoxon caused growth retardation at higher concentrations. Therefore, as expected, paraoxon inhibited yeast growth in a dose-dependent manner presumably due to the genotoxic action of OP.

Figure 7B:
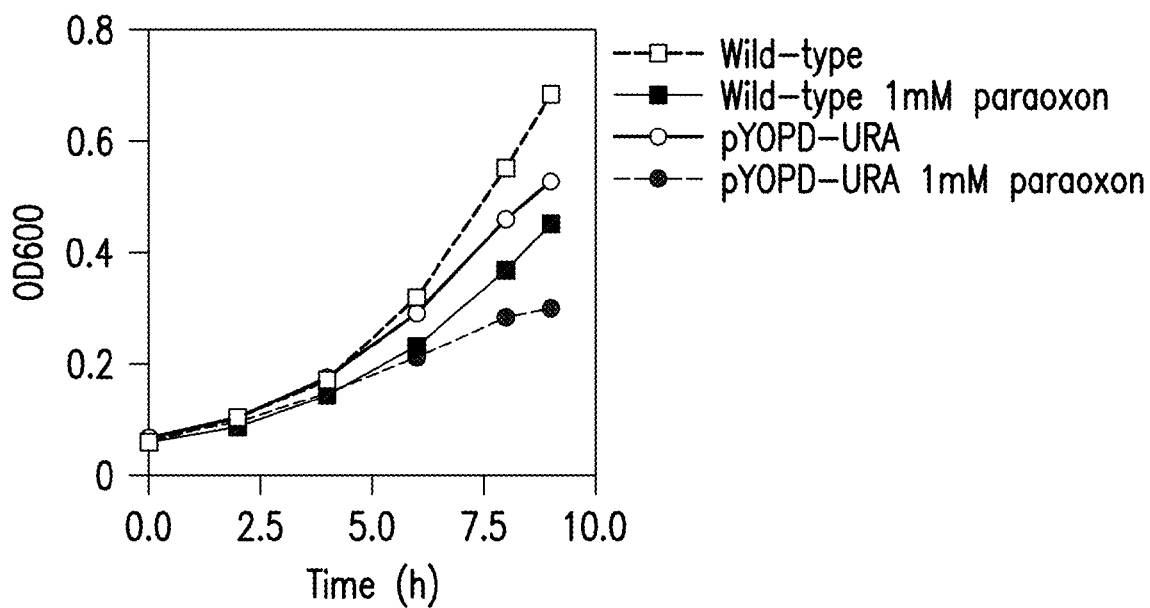
FIG. 7B is a chart illustrating growth of S. cerevisiae W3031A wild-type (pESC-URA) and recombinant OPH+ cells (monitored at $A_{600}$) in the presence of 1 mM paraoxon.

To examine whether recombinant $OPH^+$ cells were 'resistant' to the toxic actions of paraoxon, the growth of wild-type and recombinant $OPH^+$ cells was monitored in the presence or absence of 1 mM paraoxon. The growth of wild-type and $OPH^+$ cells were both inhibited to a similar extent by 1 mM paraoxon (FIG. 7B). This suggested that $OPH^+$ cells were not more resistant to the toxic actions of paraoxon. Without being limited to any particular mechanism of action, this may be due to: (i) the paraoxon hydrolysis products being toxic to yeast, and/or (ii) inability of (some) yeast cells to hydrolyze paraoxon due to a heterogeneous $OPH^+$ population, i.e. the $OPH^+$ plasmid was unstable and not stably maintained in yeast (Section 1.4, Table 2).

Paraoxon inhibited *S. cerevisiae* growth in a dose-dependent manner. High concentrations of paraoxon (4.0 mM) resulted in a prolonged lag phase.

Example 4

Ability of Yeast Enzyme Lysates to Hydrolyze Paraoxon

*S. cerevisiae* W3031A, harboring pESC-URA (empty plasmid control) and pOPD-ESC-URA plasmids, was grown in SD media containing 2% galactose (pGAL1 inducing conditions). During the exponential phase of growth, yeast cells were harvested by centrifugation, and cell pellets were frozen. Enzyme lysates were prepared by incubating the cells with 0.5 ml Y-MER dialyzable lysis buffer (Pierce Biotechnology) for 20 min at room temperature (RT), followed by centrifugation at 24,000×g for 15 min at 4° C. To measure cytosolic paraoxonase activity, 25 μl of the supernatant was mixed with 975 μl of reaction buffer (50 mM HEPES pH 7.5, 0.5 mM paraoxon, 2% methanol). For the triton extractable enzyme assay (detergent extractable), the membrane pellet from the centrifugation step was resuspended in 100 μl of 1% triton X 100 in 50 mM HEPES pH 7.5, incubated for 20 min at RT, and then centrifuged for 2 min at 15,000 rpm. The resulting supernatant was applied as for the cytosolic fraction. P-nitrophenol release was measured at 405 nm using a spectrophotometer for 5 min after the baseline stabilized. At least 3 replicates were measured per sample. Paraoxonase activity was calculated using the extraction coefficient of $1.7 \times 10^4$ $M^{-1}$ $cm^{-1}$ and presented as μmoles paraoxon hydrolyzed/min/mg protein. The activities of yeast lysates were compared to lysates prepared from *E. coli* harboring an optimized bacterial opd expression plasmid.

Control enzyme lysates, prepared from yeast cells harboring the empty plasmid, were not able to hydrolyze paraoxon. In contrast, yeast cells harboring the opd expression plasmid, produced functional OPH protein that hydrolyzed paraoxon (Table 1). Most (75%) of the enzyme activity in *S. cerevisiae* was membrane associated (triton extractable) with the remainder in the cytosolic fraction. This distribution is comparable to the wild-type *Flavobacterium* species (Mulbry W W & Karns J S., (1989) J Bacteriol 171, 6740-6). No difference in paraoxonase activity was detected in lysates prepared from yeast cells harboring the wild-type opd gene or a yeast codon-optimized opd gene; this suggests that codon bias may not be a limiting determinant for efficient opd expression in yeast.

TABLE 1

Paraoxonase activity of enzyme lysates prepared from *S. cerevisiae* harboring pOPD-ESC-URA and *E. coli* harboring an optimized opd expression plasmid

| Protein fraction | Specific activity[1] | |
|---|---|---|
| | *S. cerevisiae*[2] | *E. coli*[3] |
| Cytosolic | 0.208 | 7.6 |
| Triton extractable | 0.644 | 1.1 |
| % of triton extractable/total | 75 | 13 |

[1]Specific activity represents μmoles paraoxon hydrolyzed/min/mg total protein
[2]Average of 3 cultures after subtraction for background activity from control cultures
[3]Data from a single culture after subtraction for background activity from control cultures Higher paraoxonase activity was evident in E. coli lysates harboring an optimized opd bacterial expression plasmid compared to yeast lysates. The higher activity may be attributed to a gene dosage effect. For example, the copy number of the E. coli plasmid (ColE1 origin of replication) is typically 300-500 plasmids per cell while the corresponding copy number of the yeast 2μ plasmid is approximately 30-50 plasmids per cell (Orr-Weaver T L & Szostak J W (1983) Mol Cell Biol 3, 747-9) or about 10-fold lower. In addition, the yeast plasmid was found to be unstable and not maintained consistently in the yeast population. Plating yeast cells harboring the yeast plasmids onto selective and non-selective media indicated that only 20-25% of the yeast cells maintained the plasmid (Table 2). Therefore, the specific activity of the yeast lysates may be underestimated compared to E. coli. The instability or low segregational stability of the yeast 2μ plasmid has been reported previously (Murray A W & Szostak J W (1983) Cell 34, 961-70). This issue can be rectified by stably integrating the opd gene into the S. cerevisiae genome. Stable yeast cells with up to 100 copies of the integrated sequence can be generated by targeted homologous recombination (Parekh R et al., (1995) Protein Expr Purif 6, 537-45; Parekh R N et al., (1996) Biotechnol Prog 12, 16-21).

TABLE 2

Stability[1] of S. cerevisiae W3031A harboring pESC-URA and pOPD-ESC-URA

| Plasmid | CFU/ml (non-selective)[2] | CFU/ml (selective)[3] | Cells maintaining the plasmid (%) |
|---|---|---|---|
| pESC-URA | $6.57 \times 10^8$ | $1.65 \times 10^8$ | 25 |
| pOPD-ESC-URA | $3.37 \times 10^8$ | $6.77 \times 10^7$ | 20 |

[1]Results are averages from 3 independent cultures
[2]Non-selective media, YPD
[3]Selective media, SD-URA Recombinant yeast cells harboring the opd expression plasmid produced functional OPH protein capable of hydrolyzing paraoxon. Most of the enzyme activity was membrane-associated which is analogous to the wild-type Flavobacterium enzyme. Expression of opd from the yeast 2μ plasmid most likely results in a heterogeneous OPH$^+$ population due to plasmid instability.

Example 5

Ability of Intact Recombinant Yeast to Hydrolyze Paraoxon

Exponentially growing S. cerevisiae W3031A, harboring the pESC-URA (control) or pOPD-ESC-URA plasmids, was grown in SD media containing 2% galactose (pGAL1 inducing conditions). The yeast cells were harvested by centrifugation, and paraoxonase assays were performed using intact cells. As a comparison, whole cell paraoxonase activity was also measured from E. coli cultures harboring a bacterial opd optimized expression plasmid.

Intact yeast cells harboring the opd expression plasmid were able to hydrolyze paraoxon (Table 3). Yeast cells exhibited 3- to 4-fold higher paraoxonase activity than intact E. coli cells. Yeast enzyme lysates and intact cells displayed different amounts of paraoxonase activity; intact cells exhibited only 2-3% of the total activity of the cell. Without being limited to any particular mechanism of action, a limitation of the ability of intact yeast cells to hydrolyze paraoxon may be the rate of entry of paraoxon into the cell (Mulchandani A et al., (1999) Biotechnol Bioeng 63, 216-23; Shimazu M et al., (2003) Biotechnol Prog 19, 1612-4). The barrier that limits the rate of entry into the cell may be either the cell wall or cell membrane.

TABLE 3

Whole cell paraoxonase activity of S. cerevisiae harboring pOPD-ESC-URA and E. coli harboring an optimized opd expression plasmid Whole cell activity[1]

| S. cerevisiae[2] | E. coli[3] |
|---|---|
| 0.231 | 0.062 |

[1]Whole cell activity represents μmoles paraoxon hydrolyzed/min/$10^9$ CFU
[2]Average of 3 cultures after subtraction for background activity from control cultures
[3]Data from a single culture after subtraction for background activity from control culture Intact recombinant yeast cells were capable of hydrolyzing paraoxon and functioning as a yeast biocatalyst. Intact yeast cells displayed lower paraoxon hydrolysis compared to enzyme lysates presumably because a rate limiting step is the rate of paraoxon diffusion into the cell.

Example 6

Ability of Spheroplasts to Hydrolyze Paraoxon

Exponentially growing S. cerevisiae W3031A harboring pOPD-ESC-URA was grown in SD media containing 2% galactose (pGAL1 inducing conditions). The yeast cells were harvested by centrifugation, divided equally, and were incubated in spheroplast buffer (1.2 M sorbitol, 50 mM EDTA, 50 mM potassium phosphate pH 7.5) in the presence or absence of 1 μl/ml β-mercaptoethanol and 15 μl/ml zymolyase (5 units/μl, cell wall removal enzyme) at 37° C. After 20 min, spheroplast formation was confirmed by microscopic examination of lysed cells by the addition of 0.2% SDS (1:1 mixing) and by the inability of spheroplasts to form a colony after 48 h growth on selective medium. The control cells and spheroplasts were washed (1,800×g, 5 min) four times with 1M sorbitol, 50 mM HEPES pH 7.5 prior to assaying for paraoxon hydrolysis.

Paraoxon hydrolysis of spheroplasts, which lack a cell wall, was compared to intact yeast cells. There was no substantial difference in paraoxon hydrolysis between intact control cells and spheroplasts (Table 4). Thus, in some embodiments, removal of the cell wall does not increase the rate of paraoxon entry into the cell, and hence increase the paraoxon hydrolysis of the yeast biocatalyst. Therefore, a likely barrier to paraoxon entry in one or more of these embodiments is the yeast cell membrane.

TABLE 4

Whole cell paraoxon hydrolysis of S. cerevisiae control and spheroplast cells harboring pOPD-ESC-URA Whole cell S. cerevisiae activity[1,2]

| Intact control cells | Spheroplasts |
|---|---|
| 0.041 | 0.038 |

[1]Whole cell activity represents μmoles paraoxon hydrolyzed/min/$10^9$ cells
[2]Number of cells determined microscopically using a haemocytometer Removal of the cell wall did not improve whole cell paraoxon hydrolysis in some embodiments. This suggests that paraoxon cell entry may not be impeded by the cell wall.

Example 7

Ability of Permeabilized Yeast to Hydrolyze Paraoxon

*S. cerevisiae* W3031A harboring pOPD-ESC-URA plasmids, was grown in SD media containing 2% galactose (pGAL1 inducing conditions). At $OD_{600}$ 0.5, the yeast cells were harvested by centrifugation, divided equally, and incubated in TE buffer (1 mM EDTA, 10 mM Tris-HCl pH 7.5) in the presence or absence of dimethylsulphoxide containing 0.1% digitonin at 30° C. (Becker J M et al., (1988) Biochim Biophys Acta 968, 408-17). After 15 min shaking, the presence of permeabolized cells was assessed by the addition of 0.4% trypan blue (1:1 mixing). Microscopic examination indicated that 99% of the digitonin-treated cells appeared blue (per field of vision) while control cells remained opaque. The appearance of 'blue' yeast cells is indicative of a damaged, or permeabolized membrane. Digitonin-treated cells also exhibited a $10^3$-fold lower viable cell count after 48 h incubation onto selective medium as expected. The control and permeabolized cells were washed (2,000×g, 10 min) four times with TE buffer prior to assaying for paraoxonase activity.

Treatment of the cells with the permeabilization agent digitonin increased paraoxon hydrolysis 3 to 4-fold compared to control cells (Table 5). This suggests that disrupting the yeast membrane increases the rate of paraoxon entry into the cell and hence the yeast biocatalytic activity. This is in agreement with research using bacterial biocatalysts which have shown that the bacterial cell envelope acts as a permeability barrier to the substrate. For example, OPH expressed on the bacterial cell surface hydrolyzes OP compounds more effectively than whole cell biocatalysts where OPH resides within the cytoplasm. Permeabilizing the outer membrane using solvents can overcome these issues and increase the rate of passive diffusion and hydrolysis, although practicing these methods may require care to be taken to avoid cell death.

TABLE 5

Whole cell paraoxon hydrolysis of *S. cerevisiae* control and permeabolized cells harboring pOPD-ESC-URA
Whole cell *S. cerevisiae* activity[1,2]

| Control cells | Permeabolized cells |
|---|---|
| 0.0064 | 0.023 |

[1]Whole cell activity represents µmoles paraoxon hydrolyzed/min/$10^9$ cells
[2]Number of cells determined microscopically using a haemocytometer Permeabilization of the yeast membrane increased the efficiency of the yeast biocatalyst presumably by disrupting the membrane and thereby increasing the rate of paraoxon entry into the cell. The results suggest the yeast membrane is the primary barrier to paraoxon entry.

Example 8

Effect of Membrane Permeating Agents Such as Ethanol on Paraoxon Hydrolysis Yeast cells harboring the pOPD-ESC-URA plasmid were grown in SD media containing 2% galactose (pGAL1 inducing conditions) and either 2%, 4%, 6% or 8% ethanol (final concentration). Growth was monitored spectrophotometrically at $OD_{600}$ and cell viability was examined by trypan blue staining. The ability of yeast cells pretreated with sub-lethal concentrations of ethanol were examined for whole cell paraoxon hydrolysis.

Figure 8:
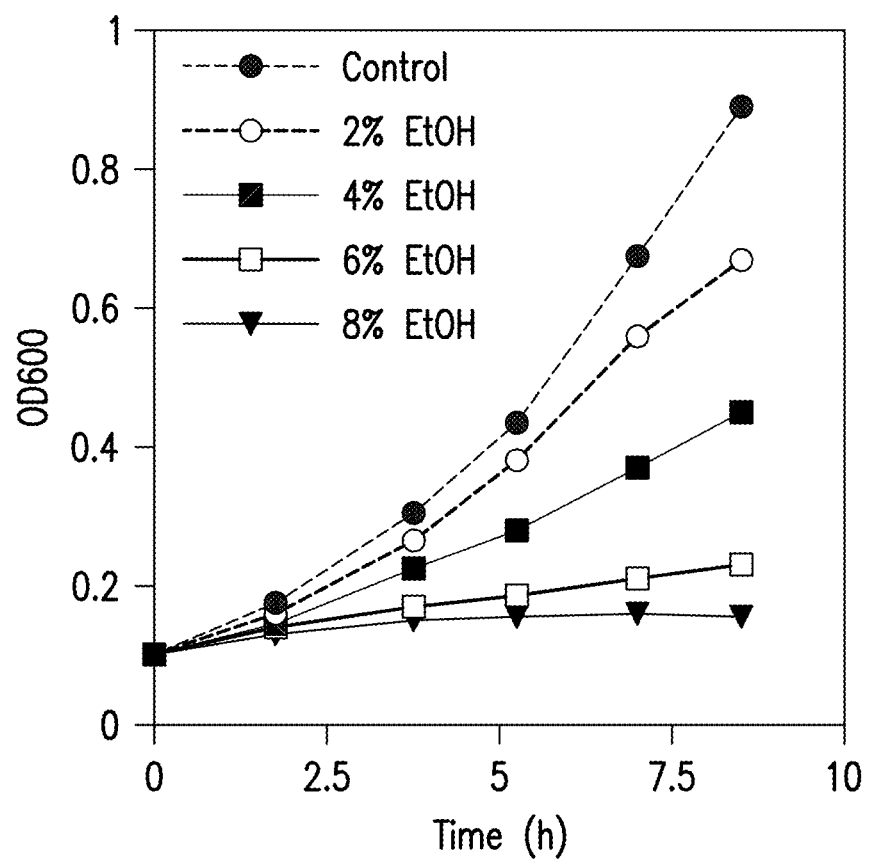
FIG. 8 is a chart illustrating growth (monitored at $A_{600}$) of S. cerevisiae harboring pOPD-ESC-URA in the presence of varying ethanol concentrations (2-8%)

Incubation with 2 or 4% ethanol resulted in a decrease in *S. cerevisiae* growth rate; incubation with higher ethanol concentrations (6-8%) severely inhibited growth (FIG. 8); however, there was no difference in the viability between control and 4% ethanol-treated cells after 3.75 h treatment. Therefore, yeast cells harboring pOPD-ESC-URA were pretreated with 2 or 4% ethanol for 4.5 h prior to performing paraoxonase assays. Pretreatment with sub-lethal concentrations of ethanol increased whole cell paraoxon hydrolysis (Table 6). Pretreatment with 2% ethanol prior to the assay increased whole cell activity 1.29-fold while pretreatment with 4% ethanol increased activity 1.46-fold compared to control cells.

TABLE 6

Whole cell paraoxon hydrolysis of *S. cerevisiae* harboring pOPD-ESC-URA pretreated with sub lethal concentrations of ethanol

| Treatment | Whole cell activity[1] | Fold-increase[2] |
|---|---|---|
| Control[3] | 0.28 | — |
| 2% Ethanol[3] | 0.36 | 1.29 |
| 4% Ethanol[3] | 0.41 | 1.46 |

[1]Whole cell activity represents µmoles paraoxon hydrolyzed/min/$10^9$ cells
[2]Fold-increase compared to control cultures
[3]No difference in viability (trypan blue staining) was observed for the different treatments Pretreatment with sub-lethal concentrations of ethanol increased whole cell paraoxon hydrolysis most likely by increasing the membrane permeability to paraoxon. Ethanol pretreatment can increase yeast biocatalytic activity.

Example 9

Sensitivity of Yeast Membrane Mutants to Paraoxon

Yeast mutants, with specific mutations in ergosterol biosynthesis, may be hypersensitive to paraoxon due to increased paraoxon diffusion through the altered yeast membranes. Therefore, growth curves in the presence or absence of a low concentration of paraoxon were performed to examine yeast membrane mutant strains for increased sensitivity to paraoxon. *S. cerevisiae* wild-type BY4741, and the membrane mutant strains erg3, erg4 and erg6 were grown overnight in complex YPD broth (plus 200 µg/ml G418 for the mutant strains) at 37° C. to stationary phase. At time zero, the cultures were divided equally and incubated in the absence or presence of 0.5 mM paraoxon. Cultures were monitored for growth spectrophotometrically at $OD_{600}$.

Figure 9C:
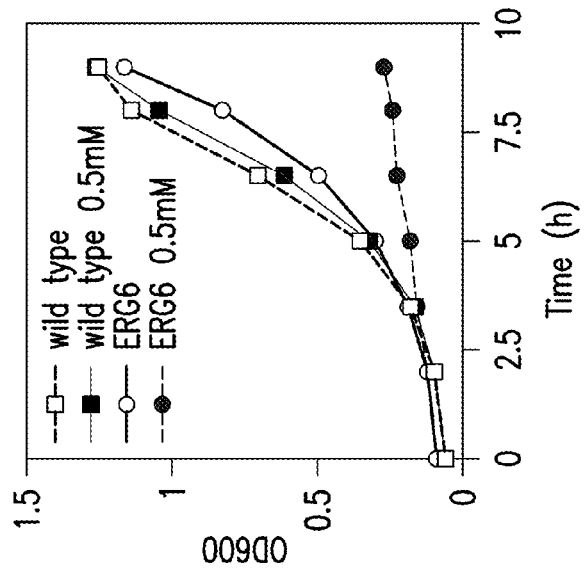
FIG. 9C is a chart illustrating the effect of 0.5 mM paraoxon on the growth (monitored at $A_{600}$) of S. cerevisiae wild-type (BY4741) and the membrane mutant strain erg6.
Figure 9B:
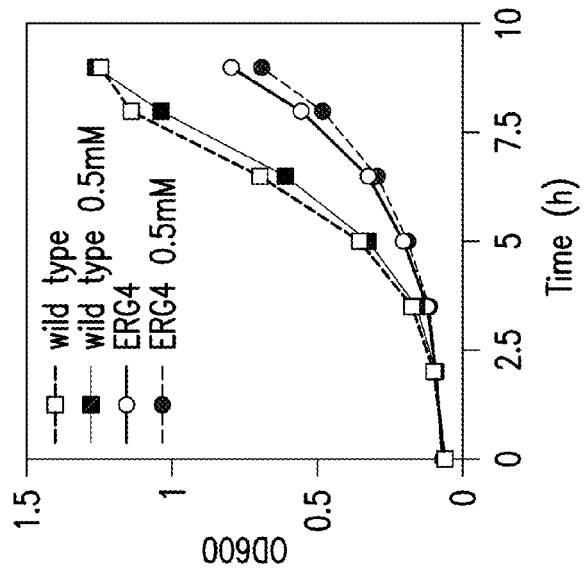
FIG. 9B is a chart illustrating the effect of 0.5 mM paraoxon on the growth (monitored at $A_{600}$) of S. cerevisiae wild-type (BY4741) and the membrane mutant strain erg4.
Figure 9A:
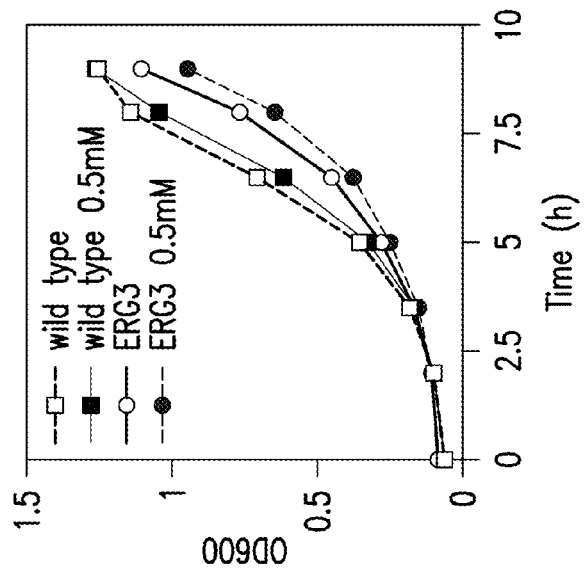
FIG. 9A is a chart illustrating the effect of 0.5 mM paraoxon on the growth (monitored at $A_{600}$) of S. cerevisiae wild-type (BY4741) and the membrane mutant strain erg3.

There was no difference in the growth rates between the wild-type and erg3 or erg4 strains in the presence or absence of 0.5 mM paraoxon, (FIGS. 9A & B). This indicated that mutations in ERG3 and ERG4, did not confer increased sensitivity to paraoxon. In contrast, 0.5 mM paraoxon resulted in a significant decrease in the growth rate of erg6, compared to the wild-type strain (FIG. 9C).

Figure 10B:
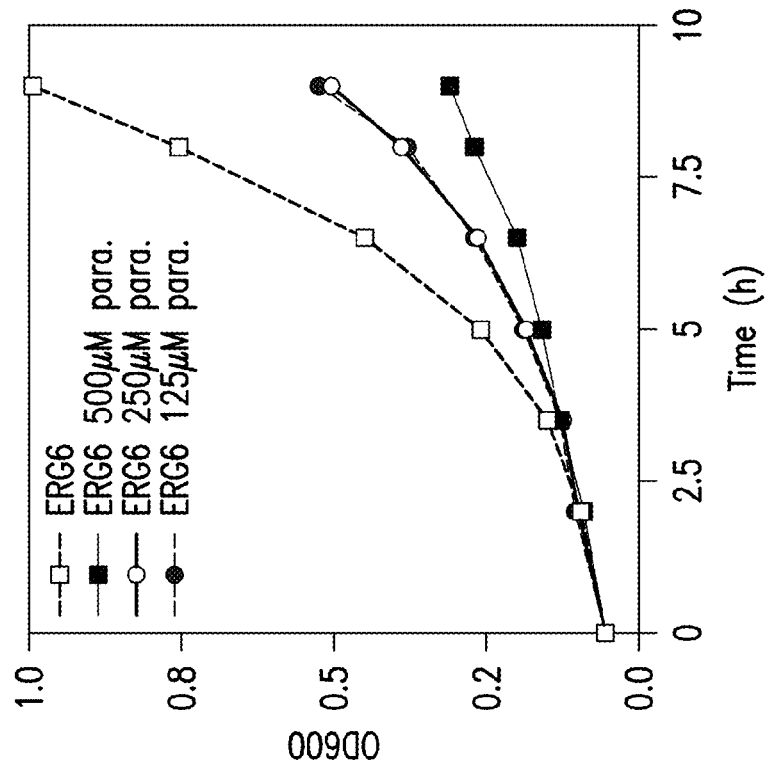
FIG. 10B is a chart illustrating the effect of 500, 250, and 125 μM paraoxon (para) on the growth of S. cerevisiae membrane mutant strain erg6.
Figure 10A:
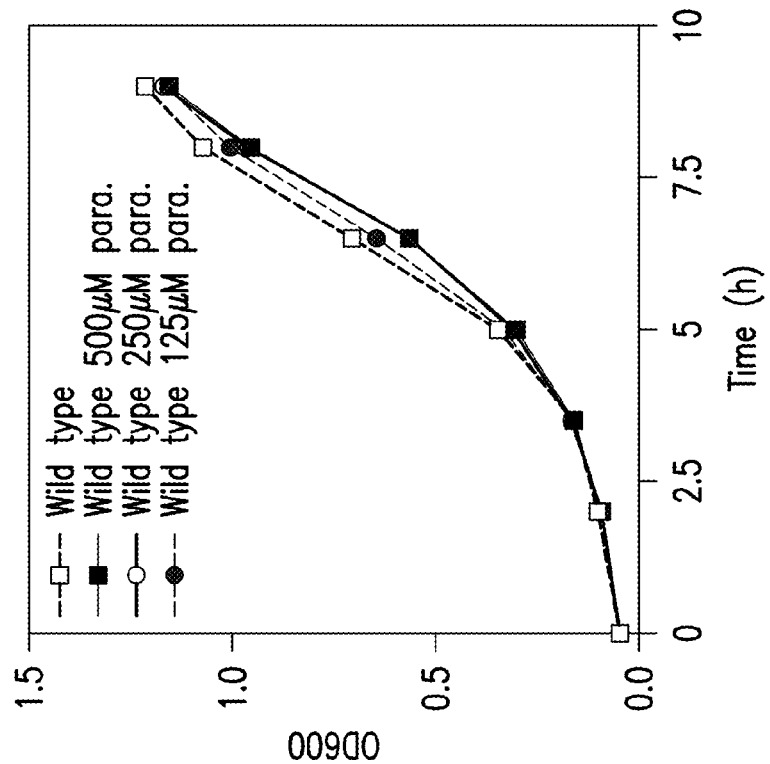
FIG. 10A is a chart illustrating the effect of 500, 250, and 125 μM paraoxon (para) on the growth of S. cerevisiae wild-type (BY4741)

To examine the degree of sensitivity of erg6 to paraoxon, additional growth curves were performed with lower (0.25 mM and 0.125 mM) paraoxon concentrations. The growth rate of erg6 was inhibited by 0.125 mM paraoxon, while this concentration had no effect on the wild-type strain (FIGS. 10A & B). Therefore, the results indicate that erg6 is hypersensitive to paraoxon and may be useful for incorporation into a yeast biocatalyst; however, a potential drawback of using the erg6 mutant is that growth rates in YPD medium are impaired compared to the wild-type strain (Welihnda A A et al., (1994) Biochim Biophys Acta 1193, 107-17).

The specific membrane mutant erg6 is hypersensitive to paraoxon, presumably due to the increased permeability of the defective membrane to paraoxon. The use of yeast membrane mutants such as erg6 may increase the efficiency of the biocatalyst.

Example 10

Microarray Analysis of Wild-Type and Recombinant OPH+ Yeast Gene Expression

Global transcription profiling (microarray analysis) was performed on *S. cerevisiae* in the presence or absence of paraoxon, and on recombinant OPH$^+$ yeast in the presence or absence of paraoxon. The comparison between wild-type cells incubated with paraoxon, and recombinant cells expressing OPH incubated with paraoxon, identified yeast genes, which were induced by the hydrolysis of paraoxon.

*S. cerevisiae* W3031A was grown at 37° C. in SDgal (induced expression) in the presence or absence of 3 mM paraoxon for 60 min; these samples were used to identify yeast genes which were upregulated in the presence of paraoxon. Cultures were also prepared from the recombinant OPH$^+$ strain in the presence or absence of 3 mM paraoxon for 60 min. These samples permitted the identification of induced genes, which were specific to paraoxon hydrolysis. RNA was prepared from triplicate cultures using TR1 reagent (Ambion) according to the manufacturers' instructions. RNA preparations were treated with DNase1 and then further purified by passing the RNA through RNeasy columns (Qiagen).

Biotin-labeled, fragmented cRNA targets was prepared from 10 µg of total RNA using standard protocols established for the Affymetrix GeneChip System (Santa Clara, Calif.). Targets were hybridized to the Affymetrix GeneChip® Yeast Genome S98 Array which contains the entire *S. cerevisiae* genome (approximately 6,200 ORFs) on a single array. Hybridizations were performed in triplicate using three RNA preparations from three independent cultures. Post-hybridization washing, staining and scanning were performed using standard conditions developed by Affymetrix. Microarray hybridization data (CEL files) were normalized using the Bioconductor implementation of GCRMA (Gentleman R C et al., (2004) Genome Biol 5, R80), and normalized hybridization data were imported into analysis program dChip for pairwise comparison of treatments. Paraoxon induced genes were defined by the following criteria: increase in expression greater than 4-fold and statistical difference (unpaired t-test, $p<0.01$) for wild-type treated versus untreated and recombinant treated versus untreated. Candidate genes associated with paraoxon hydrolysis were defined by the following criteria: increase in expression greater than 2-fold and statistical difference (unpaired t-test, $p<0.01$) for recombinant paraoxon treated versus recombinant untreated excluding paraoxon-induced genes. Hierarchical clustering was performed on each set of candidate genes with dChip using standardized expression values (z-normalization) with a distance metric of 1-correlation and linkage calculated by the centroid method.

Overall, the number of genes induced by paraoxon and the changes in expression were large. For example, pairwise comparisons for fold change ($p<0.01$) using the t-test for comparing paraoxon treated to untreated control cells, identified approximately 1,900 genes that were differentially expressed. The false discovery rate (FDR) for differential expression was low (0.3%) indicating that only about 6 of the 1,900 genes were estimated to be wrong. 65 genes were identified to be differentially expressed due to paraoxon exposure and were selected by: (i) 4-fold differential expression or greater; (ii) statistically significant based on the t-test with a p value<0.01; (iii) increased expression only (not repressed) and (iv) induced by paraoxon from both treatment sets (wild-type and recombinant yeast). A selected list of 7 paraoxon-inducible genes, based upon fold-induction, is depicted in Table 7. The level of differential expression ranged from 18 up to 1,700-fold induction (for YGR035C) and thus represented large increases in expression levels. Four out of the 7 paraoxon-inducible genes have unknown functions; however, a common theme for gene function assignment is drug resistance which is not unexpected.

TABLE 7

Selected list of paraoxon-inducible genes

| Accession | Name/ Alias | Fold-induction | P-value | Description |
|---|---|---|---|---|
| YGR035C | None | 1789.2 | 0.000 | Function unknown; activated by Yrm1p and Yrr1p along with genes involved in MDR. |
| YHR139C | SPS100 | 719.1 | 0.000 | Protein required for spore all maturation; expressed during sporulation; may be a component of the wall. |
| YOR186W | None | 269.1 | 0.000 | Hypothetical protein |
| YGR213C | RTA1 | 152.2 | 0.001 | Protein involved in 7-aminocholesterol resistance. |
| YLR346C | None | 69.6 | 0.003 | Unknown function; regulated by PDR1 (pleiotrophic drug resistance 1). |
| YIR017C | MET28 | 27.7 | 0.004 | Participates in sulfur metabolism; stress response |
| YLL056C | None | 18.5 | 0.000 | Unknown; activated by Yrm1p and Yrr1p? MDR? Similar to YGR035C. |

The number of genes and the level of differentially regulated genes associated with paraoxon hydrolysis in this specific example were not as extensive as the paraoxon-inducible genes. The reason why fewer genes were identified may be due to: (i) the 60 min paraoxon incubation time was insufficient to hydrolyze enough paraoxon to change the transcriptional profile, or (ii) the OPH$^+$ plasmid was unstable and therefore a large percentage of the population were not capable of producing paraoxon-hydrolyzed products. Nevertheless, 33 differentially expressed genes were associated with paraoxon hydrolysis. Genes were chosen on the following criteria: (i) 2-fold differential expression or greater; (ii) statistically significant based on the t-test with a p value<0.01; (iii) increased expression only (not repressed), and (iv) exclusion of genes that were induced only by paraoxon. A selected list of 4 genes associated with paraoxon hydrolysis is depicted in Table 8. Differential expression ranged from 4- to 7-fold induction. Two of the 4 gene products have unknown functions.

TABLE 8

Selected list of genes associated with paraoxon hydrolysis

| Accession | Name/ Alias | Fold-induction | P-value | Description |
|---|---|---|---|---|
| YGL205W | POX1/ FOX1 | 6.96 | 0.001 | Fatty-acyl coenzyme A oxidase, involved in the fatty acid beta-oxidation pathway; localized to the peroxisomal matrix. |

TABLE 8-continued

Selected list of genes associated with paraoxon hydrolysis

| Accession | Name/Alias | Fold-induction | P-value | Description |
|---|---|---|---|---|
| YJL219W | HXT9 | 3.94 | 0.004 | Putative hexose transporter. |
| YGR287C | None | 3.86 | 0.01 | Unknown. |
| YHL012W | None | 3.84 | 0.007 | Unknown. |

Microarray analysis identified paraoxon-inducible yeast genes and yeast genes associated with paraoxon hydrolysis. Some of these genes were massively induced and are ideal candidates for the promoter-reporter genes fusions.

Example 11

Prioritization of Paraoxon-Inducible Genes

The genes isolated by the microarray analysis were verified individually for differential expression by relative RT-PCR and quantitative real-time RT-PCR. The paraoxon-inducible genes are listed in Table 7. Prioritized genes, based on fold-induction, were analyzed to investigate whether they were induced by low concentrations of paraoxon in a dose dependent manner (0.05 to 1.0 mM). Prioritized genes, which were sensitively induced by paraoxon, were examined after various paraoxon exposure times (7.5, 15, and 30 min). Priority was given to genes that displayed characteristics that were preferential for the construction of the yeast biosensor. These included genes which displayed: (i) the greatest fold induction; (ii) sensitivity to lower concentrations of paraoxon than that used for the microarray analysis (3 mM), and (iii) quick induction response times.

Figure 11:
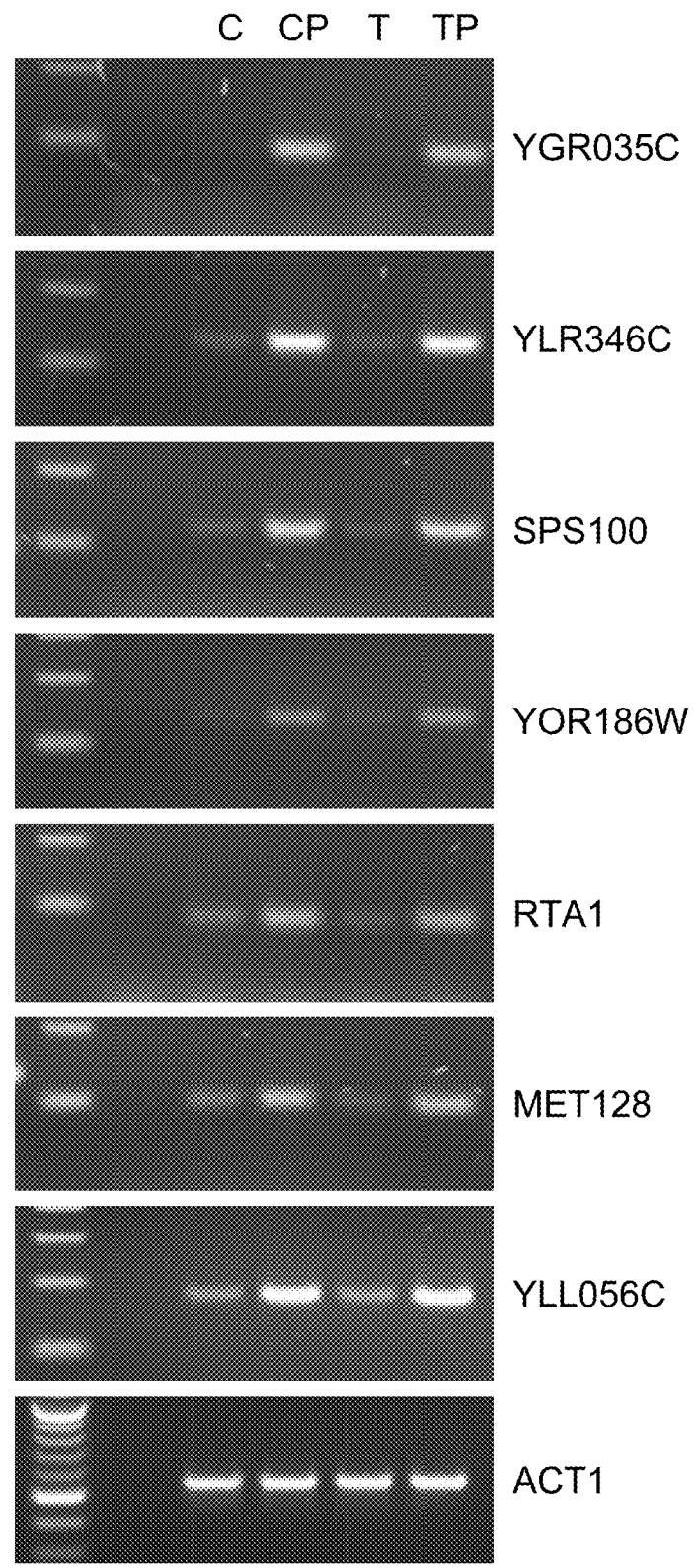
FIG. 11 is an image of gels illustrating expression of paraoxon-inducible genes (monitored by relative RT-PCR) in which RNA was prepared from wild-type or recombinant yeast incubated in the absence or presence of 3 mM paraoxon for 60 min (C, wild-type without paraoxon; CP, wild-type with paraoxon; recombinant without paraoxon (T); recombinant with paraoxon (TP))

Relative RT-PCR analysis was used to verify whether the genes identified by the microarray analysis, were differentially expressed in response to paraoxon. Primers designed against the housekeeping gene actin, were used as an internal loading control to verify that similar amounts of cDNA were used for each PCR reaction. Increased expression of YGR035C, YLR346C, SPS100, YOR186W, RTA1, MET28, and YLL056C were detected for wild-type and recombinant OPH$^+$ yeast cells grown in the presence of 3 mM paraoxon for 60 min (lanes CP and TP, FIG. 11). Therefore, relative RT-PCR was able to individually verify that the genes identified by the microarray analysis, were differentially expressed in response to paraoxon. Since YLR346C and YGR035C were shown to be significantly induced by both microarray analysis and relative RT-PCR, they were prioritized for further analysis.

Real-time RT-PCR was used to quantify changes in prioritized genes YGR035C and YLR346C in response to paraoxon. YGR035C was induced 35-fold to 190-fold in paraoxon-treated cells compared to untreated controls. YLR346C was induced 17-fold to 31-fold for the equivalent experimental samples. Therefore, real-time RT-PCR confirmed that YGR035C and YLR346C were significantly induced.

Figure 12:
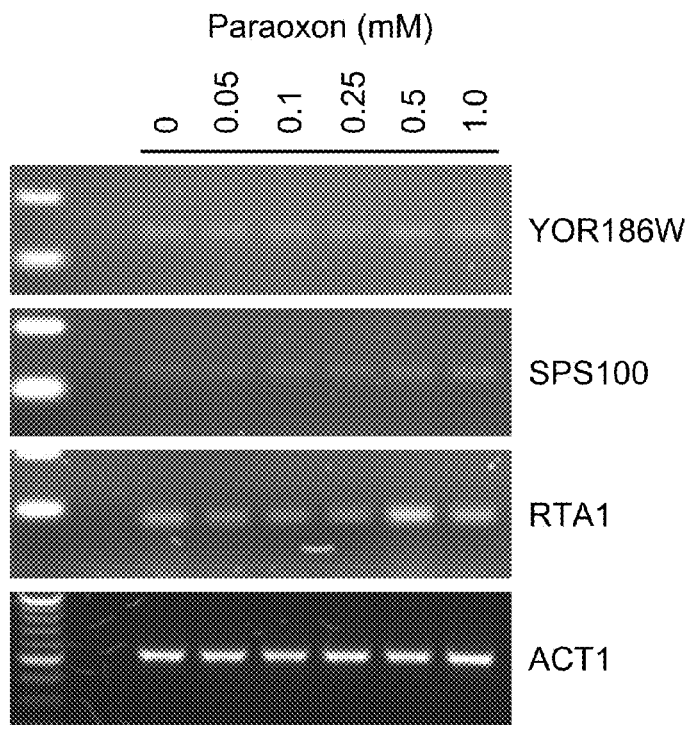
FIG. 12 is an image of gels illustrating gene expression (monitored by relative RT-PCR) of wild-type yeast incubated with varying concentrations of paraoxon for 60 min.
Figure 13:
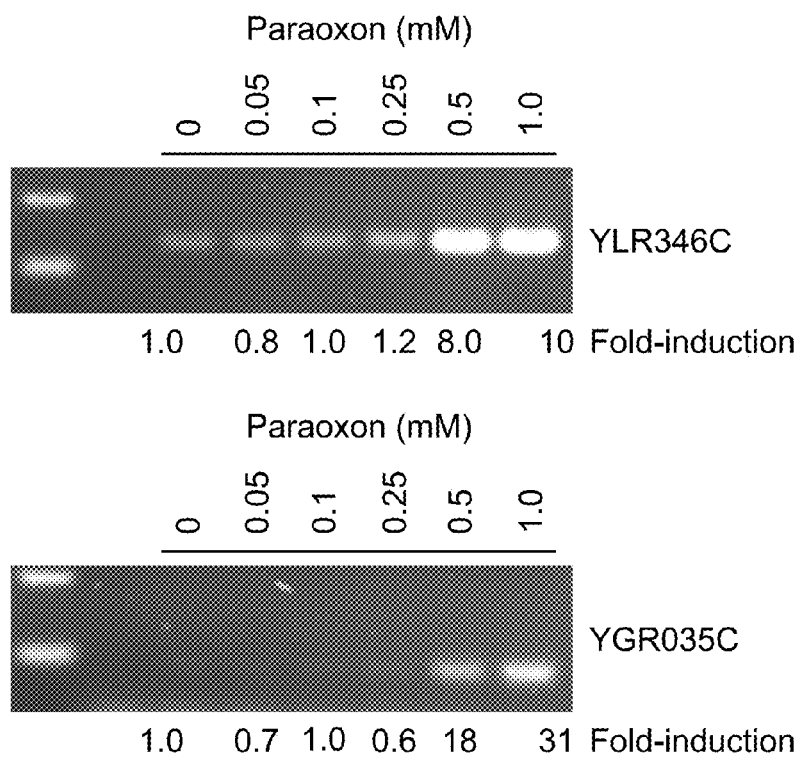
FIG. 13 is an image of gels illustrating dose response changes in gene expression monitored by relative and real-time RT-PCR in which RNA was prepared from wild-type yeast incubated with varying concentrations of paraoxon for 60 min.

To examine if the paraoxon genes were sensitively induced at paraoxon concentrations lower than that used for the microarray analysis (3 mM paraoxon), S. cerevisiae W3031A harboring pESC-URA was exposed to 0.05, 0.1, 0.25, 0.5 and 1.0 mM paraoxon for 60 min. Relative and real-time RT-PCR was performed to examine changes in gene expression. Relative RT-PCR indicated that there were no obvious changes in gene expression for YOR186W, SPS100 and RTA1 at the lower paraoxon concentrations tested (FIG. 12). In contrast, YGR035C was induced 18- and 31-fold by 0.5 and 1.0 mM paraoxon, respectively. Similarly, YLR346C was induced 8- and 10-fold by 0.5 and 1.0 mM paraoxon, respectively (FIG. 13). Therefore, YGR035C and YLR346C responded to a range of paraoxon concentrations in a sensitive manner compared to YOR186W, SPS100, and RTA1 and were prioritized for further analysis.

Figure 14:
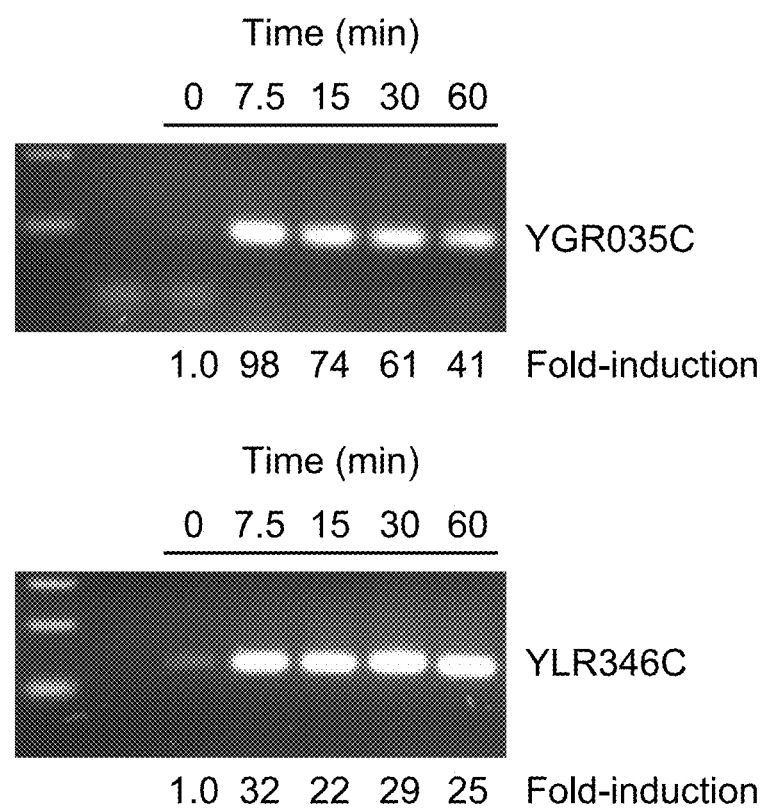
FIG. 14 is an image of gels illustrating a time course of YGR035C and YLR346C induction monitored by relative and real-time RT-PCR in which RNA was prepared from wild-type yeast incubated with 2.5 mM paraoxon.

Microarray analysis identified genes which were induced by paraoxon after 60 min exposure. Since genes which are quickly induced by paraoxon will be preferable, YGR035C and YLR346C were examined for their ability to be induced in response to short paraoxon incubations. S. cerevisiae harboring pESC-URA was exposed to 2.5 mM paraoxon for 7.5, 15, 30, and 60 min and relative and real-time RT-PCR was used to examine changes in gene expression. Both YGR035C and YLR346C were significantly and maximally (98- and 32-fold, respectively) induced after 7.5 min (FIG. 14). Continued exposure (up to 60 min) resulted in a decrease in fold-induction compared to the initial 7.5 min value.

Real-time RT-PCR was used to quantify changes in gene expression and confirmed the differential regulation of the paraoxon-inducible gene candidates identified by the microarray analysis. YGR035C and YLR346C were prioritized for use in Examples 13-14 since they: (i) are significantly induced up to 190 and 32-fold, respectively; (ii) are sensitive to a range of paraoxon concentrations, and (iii) are induced after 7.5 min exposure to paraoxon.

Example 12

Prioritization of Genes Associated with Paraoxon Hydrolysis

The genes identified by the microarray analysis (Table 8) were verified individually for differential expression by real-time RT-PCR.

Real-time RT-PCR was used to examine YHL012W, HXT9, PDX1, and YGR287C expression from wild-type yeast cells in the absence or presence of paraoxon (C and CP, respectively), and recombinant OPH$^+$ yeast in the absence or presence of paraoxon (T and TP respectively). There was no difference in YHL012 expression in the presence or absence of paraoxon, or between the wild-type and recombinant yeast (Table 9). HXT9 expression was induced approximately 3-fold by paraoxon; however paraoxon induced HXT9 expression in both wild-type and recombinant OPH$^+$ yeast cells indicating that HXT9 induction was not associated with opd expression and hence paraoxon hydrolysis. This indicates that real-time PCR was not able to verify the results of the microarray for the candidate genes YHL012 and HXT9. In contrast, an increase in PDX1 expression (2.4-fold) was detected only in recombinant OPH$^+$ yeast in the presence of paraoxon indicating that PDX1 expression was associated with paraoxon hydrolysis. Similarly, YGR287C expression was increased 9-fold in recombinant OPH$^+$ yeast cells in the presence of paraoxon; however, paraoxon also induced YGR287C in wild-type cells, albeit to a much lesser extent (2-fold).

TABLE 9

Real-time RT-PCR analysis of the candidate genes
associated with paraoxon hydrolysis

| Accession/name | Fold-induction | | | |
|---|---|---|---|---|
| | $C^a$ | $CP^b$ | $T^c$ | $TP^d$ |
| YHL012W | 1.0 | 0.8 | 1.0 | 1.0 |
| HXT9 | 1.0 | 2.8 | 1.0 | 2.7 |
| POX1 | 1.0 | 0.9 | 1.0 | 2.4 |
| YGR287C | 1.0 | 1.9 | 1.0 | 9.1 |

[a] S. cerevisiae W3031A harboring pESC-URA (empty plasmid)
[b] S. cerevisiae W3031A harboring pESC-URA (empty plasmid) incubated with 3 mM paraoxon
[c] S. cerevisiae W3031A harboring pOPD-ESC-URA (expressing opd)
[d] S. cerevisiae W3031A harboring pOPD-ESC-URA (expressing opd) incubated with 3 mM paraoxon Real-time RT-PCR confirmed that PDX1 and YGR287C were preferentially expressed in recombinant OPH+ yeast in the presence of paraoxon, suggesting induction was associated with paraoxon hydrolysis. Therefore, PDX1 and YGR287C were prioritized for use in Examples 13-14.

Example 13

A Yeast YeGFP Biosensor that Detects Paraoxon

A plasmid containing a yeast codon optimized enhanced GFP (YeGFP) gene was constructed. The promoter regions (−500 and −1000 bp upstream fragments) of the 2 prioritized paraoxon-inducible genes identified in Example 11 (YGR035C and YLR346C) were cloned, fused to YeGFP and transformed into wild-type S. cerevisiae. The sequence of YGR035C-FI-YeGFP is shown (FIG. 15A; bold, promoter sequence; underline, YeGFP gene sequence). The sequence of pYLR346C-FI-YeGFP is shown (FIG. 15B; bold, promoter sequence; underline, YeGFP gene sequence). The functionality of the yeast biosensor was examined by measuring YeGFP fluorescence after different exposure times to paraoxon, and in the presence of different concentrations of paraoxon.

Construction of a YeGFP Promoterless Yeast Vector.

YeGFP is an *Aequorea victoria* GFP variant that has 2 amino acid changes which increases fluorescence intensity 75 times more than the wild-type GFP. In addition YeGFP is codon optimized for expression in the yeast *Candida albicans*, and is also highly fluorescent in *S. cerevisiae* (Cormack B P et al., (1997) Microbiology 143, 303-11). A strain of *C. albicans* containing YeGFP was used. The 700 bp YeGFP gene was PCR-amplified using a proofreading polymerase and *C. albicans* YeGFP genomic DNA as template. The PCR primers were designed to contain BamHI and SpeI endonuclease sites for cloning into the respective sites of pESC-HIS. The resulting 'promoterless' pYeGFP-HIS plasmid, contained a multiple cloning site (MCS, BamHI, SmaI, SalI, XhoI, and Sad) for cloning the paraoxon-inducible promoters. Cloning and propagation was performed in *E. coli* ER2738. The identity of YeGFP was verified by DNA sequencing.

Construction of Paraoxon-Inducible Promoter-YeGFP Fusion Reporter Plasmids.

The promoter sequences were initially mapped using the *Saccharomyces* promoter database (SCPD) (maintained by Cold Spring Harbor Laboratories, Cold Spring Harbor, N.Y.). The SCPD has extensive information on yeast genes with previously mapped regulatory regions, has annotated putative regulatory sites of all yeast genes, and has extensive tools for the retrieval of promoter sequences and known regulatory elements for the gene of interest. Although the promoters of the 2 prioritized paraoxon-inducible genes (YGR035C and YLR346C) had not been previously mapped in the literature, analysis of the 5' upstream promoter regions using the SCPD, identified putative promoter regulatory sites involved in drug and stress resistance as expected. To encompass the YGR035C and YLR346C promoters, 2 putative promoter fragments for each gene containing approximately −1000 and −500 bp upstream sequence (relative to ATG) were cloned in front of YeGFP. The putative promoter regions were PCR-cloned using *S. cerevisiae* W3031A genomic DNA as template and a proofreading thermostable DNA polymerase. The 5' and 3' primers contained SalI and BamHI sites, respectively, for directional cloning into the same sites of pYeGFP-HIS to generate promoter-reporter gene fusions. The resulting plasmids were named F1 and F2 for the −1000, and −500 promoter fragments, respectively (Table 11).

Paraoxon-Inducible Promoter-YeGFP Biosensor Assays.

Figure 16:
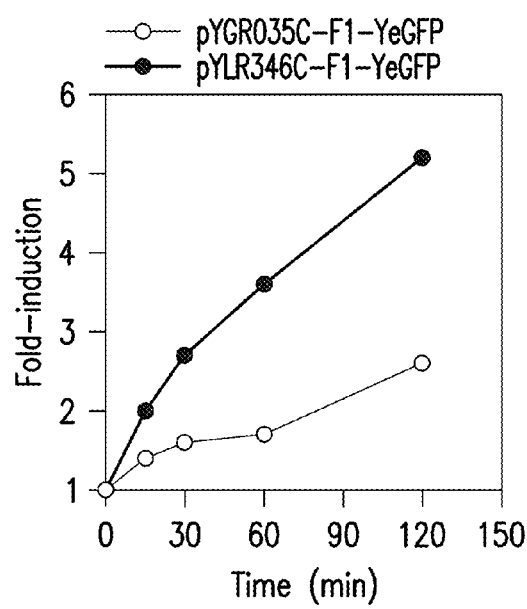
FIG. 16 is a chart illustrating a time course of YeGFP induction in *S. cerevisiae* in the presence of 3 mM paraoxon and harboring either pYGR035C-F1-YeGFP or pYLR346C-F1-YeGFP.

To test whether the promoter regions conferred sensitivity to paraoxon, YeGFP fluorescence assays were performed. *S. cerevisiae* BY4741 was transformed with the promoter-reporter constructs and the empty 'promoterless' control vector. *S. cerevisiae* BY4741 was used in preference to *S. cerevisiae* W3031A since W3031A exhibited higher autofluorescence than BY4741. Cells were grown in SDgal/suc (3% galactose, 1% sucrose) lacking histidine in the presence or absence of paraoxon for 15, 30, 60, and 120 min at 37° C. Cells were harvested by centrifugation, washed in PBS, resuspended in 10 mM Tris-HCl pH 8.5, and duplicate samples were measured for YeGFP fluorescence (excitation and emission max of 485 and 520 nm) using the FLUOstar OPTIMA (BMG). The samples were resuspended in alkaline buffer since GFP is pH sensitive. GFP is stable at pH 7 to 11.5, but may loose activity at other pHs (e.g., 50% lower at pH 6). Consequently, media and pH formulations, in some embodiments, may be optimized to maintain the pH of yeast cultures at or near a neutral pH. All results were normalized to the number of cells present ($OD_{600}$), to the 'promoterless' control vector (YeGFP-HIS) and are presented as fold-induction compared to cells lacking paraoxon. Yeast cells incubated in the presence of paraoxon exhibited increased YeGFP fluorescence compared to cells lacking paraoxon (FIG. 16). Yeast cells harboring pYLR346C and pYGR035C-YeGFP were induced 5 and 3-fold, respectively, after 2 h incubation with 3 mM paraoxon. Incubation with paraoxon for longer than 2 h (4, 6, 8, and 24 h) did not increase the fold-induction (data not shown). A time course analysis indicated that YeGFP fluorescence was quickly induced by paraoxon. For example, yeast strains harboring pYLR346 were induced 2-fold after only 15 min exposure to paraoxon.

Figure 17:
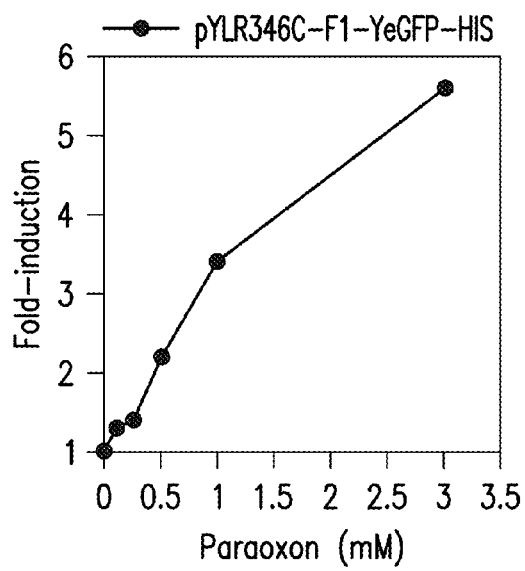
FIG. 17 is a chart illustrating a dose response of YeGFP-induction in *S. cerevisiae* harboring pYLR346C-F1-YeGFP in the presence of 0.1 to 3.0 mM paraoxon for 120 min.

To determine the sensitivity of the assay and to investigate whether the recombinant yeast responded to different paraoxon concentrations, a dose response curve was performed. *S. cerevisiae* harboring pYLR346C-F1-YeGFP was incubated with 0.1, 0.25, 0.5, 1.0, and 3 mM paraoxon for 2 h prior to assaying for YeGFP fluorescence. The construct harboring the promoter fragment YLR346C-F1 was chosen for this experiment since it was most responsive to 3 mM paraoxon (FIG. 16, 5-fold). As the concentration of paraoxon increased, the level of YeGFP induction increased (FIG. 17). In addition, the level of fluorescence increased, albeit modestly (1.3-fold), at the lowest concentration tested (0.1 mM paraoxon). Therefore, the results indicated that the yeast biosensor exhibited a dose response to paraoxon, and was responsive to 0.1 mM paraoxon.

YeGFP fluorescence was induced up to 5-fold in the presence of paraoxon. The level of YeGFP induction, however, was lower than the fold-change in gene expression observed under the same conditions (30-fold for YLR346C). Without being limited to any particular mechanism of action, this may be attributed to a sub-optimal promoter fragment driving YeGFP expression. Only 2 promoter fragments (approximately −500, and −1000 relative to the ATG) for each gene were tested. In some embodiments, additional promoter characterization may include 5' promoter deletion analysis to further identify the promoter fragment necessary to confer paraoxon inducibility. Additional promoter characterization may also include identification of sequence 3' of the ATG start site that may also contain regulatory transcriptional motifs.

In addition, the difference between YeGFP fluorescence and YeGFP expression may be reduced by providing additional transcription factor(s) required for inducing expression from the promoters located on multicopy plasmids. The YLR346C promoter is maintained at approximately 20-50 copies per cell on the multicopy plasmid while there is only a single copy of the chromosomal endogenous promoter. Consequently, the endogenous transcription factors required for paraoxon induction may be saturated by the presence of multiple transcription factor binding sites. Providing additional transcription factor(s) may include reducing the number of plasmid copies or coexpressing the required transcription factors (if known) may overcome this limitation. Background autofluorescence of yeast may lead to a reduction in the differential level of induced expression under some circumstances. In such cases, using yeast strains with lower background fluorescence, for example, S. cerevisiae BY4741 may offset or overcome autofluorescence, For example, S. cerevisiae W3031A displayed higher background autofluorescence than BY4741. Consequently, BY4741 was used as a host propagating strain for biosensor fluorescence assays.

Yeast cells harboring paraoxon-inducible promoter-YeGFP fusions displayed up to 5-fold increases in fluorescence levels compared to control cells when incubated in the presence of paraoxon. Increased YeGFP levels were detected after 15 min exposure to paraoxon. The YeGFP biosensor was sensitive to as low as 0.1 mM paraoxon and exhibited dose-dependent characteristics by increasing YeGFP fluorescence as the paraoxon concentration increased. The results demonstrate the ability of yeast cells to function as a biosensor and detect the presence of paraoxon.

Example 14

A Yeast YDsRed Biosensor that Detects Paraoxon Hydrolysis

A plasmid containing a yeast codon optimized DsRed (YDsRed) gene was constructed. The promoter regions (−500 and −1000 bp upstream fragments) of the 2 prioritized paraoxon-inducible genes identified in Examples 10-12 (PDX1 and YGR287C) were cloned, fused to YDsRed and transformed into wild-type and recombinant OPH+ S. cerevisiae. The sequence of YGR287C-FI-YDsRed is shown (FIG. 18A; bold, promoter sequence; underline, YDsRed gene sequence). The sequence of pPDX1-FI-YDsRed is shown (FIG. 18B; bold, promoter sequence; underline, YDsRed gene sequence). The ability of the yeast biosensor to increase YDsRed fluorescence was compared in wild-type (control) and recombinant yeast cultures. YDsRed fluorescence was measured after different exposure times to paraoxon, and in the presence of different concentrations of paraoxon.

Construction of a YDsRed Promoterless Yeast Vector.

DsRed-express (Clontech) is a variant of the coral reef Discoma species red fluorescent protein that has been modified to improve solubility of the protein and codon-optimized for high expression in eukaryotic cells for enhanced sensitivity. This results in high fluorescence intensity, which is comparable to EGFP. Nevertheless, DsRed express contains a number of codons that are rarely used in S. cerevisiae. Therefore, DsRed was codon optimized for expression in yeast (performed by Bio S & T) (FIG. 4B). The yeast codon optimized DsRed, YDsRed, was also designed to contain a preferred yeast ribosome binding site and BamHI and NotI restriction endonuclease sites for cloning into the corresponding sites of pESC-LEU (Stratagene). The resulting pYDsRed-LEU promoterless vector contained an adequate MCS for cloning the PDX1 and YGR287C promoters.

Construction of promoter-YDsRed fusion reporter plasmids. To encompass the PDX1 and YGR287C promoters, 2 putative promoter fragments for each gene containing approximately −1000 and −500 bp upstream sequence (relative to ATG) were cloned in front of YDsRed. The putative promoter regions were PCR-cloned using S. cerevisiae W3031A genomic DNA as template and a proofreading thermostable DNA polymerase. The 5' and 3' primers contained SalI and BamHI sites, respectively, for directional cloning into the equivalent sites of pYDsRed-LEU to generate promoter-reporter gene fusions. The resulting plasmids were named F1 and F2 for the −1000, and −500 promoter fragments, respectively.

Promoter-YDsRed Biosensor Assays.

To analyze whether the promoter regions were 'switched on' by paraoxon hydrolysis, YDsRed fluorescence assays were performed. S. cerevisiae BY4741 harboring pESC-URA (control strain lacking OPH) was transformed with the promoter-reporter constructs and the empty 'promoterless' control vector (pYDsRed-LEU). The recombinant OPH+ (test strain, expressing OPH) was transformed with the analogous plasmids. Cells were grown in SDgal/suc lacking leucine in the presence or absence of 3 mM paraoxon for 4.5 h at 37° C. Cells were harvested by centrifugation, washed in PBS, resuspended in 10 mM Tris-HCl pH 8.5, and duplicate samples were measured for YDsRed fluorescence (excitation and emission at 554 nm and 590 nm, respectively). All results were normalized to the number of cells present ($OD_{600}$), to the 'promoterless' control vector (YDsRed-LEU) and are presented as fold-induction compared to cells lacking paraoxon. Recombinant OPH+ cells, incubated in the presence of paraoxon, demonstrated induced YDsRed fluorescence compared to cells lacking paraoxon for all constructs analyzed (Table 10). Induction ranged from 2 to 8-fold, and is comparable to the induction results obtained from the quantitative real-time RT-PCR. Importantly, the same constructs demonstrated little to no paraoxon inducibility in the control strain lacking OPH (pESC-URA empty vector). Therefore, YDsRed was not induced by paraoxon per se; induction required OPH indicating that YDsRed induction was strictly associated with paraoxon hydrolysis.

TABLE 10

YDsRed fold-induction from yeast cells grown in the presence of 3 mM paraoxon for 4.5 h*.

| Control yeast (pESC-URA) | | Recombinant OPH+ yeast (pYOPD-URA) | |
|---|---|---|---|
| Promoter | Fold-induction[a] | Promoter | Fold-induction[a] |
| pYGR287C-F1 | 1.41 | pYGR287C-F1 | 2.1 |
| pYGR287C-F2 | 1.13 | pYGR287C-F2 | 2.4 |

TABLE 10-continued

YDsRed fold-induction from yeast cells grown in the presence of 3 mM paraoxon for 4.5 h*.

| Control yeast (pESC-URA) | | Recombinant OPH+ yeast (pYOPD-URA) | |
|---|---|---|---|
| Promoter | Fold-induction[a] | Promoter | Fold-induction[a] |
| pPOX1-F1 | 0.84 | pPOX1-F1 | 3.0 |
| pPOX1-F2 | 0.74 | pPOX1-F2 | 8.3 |

*S. cerevisiae BY4741 control (pESC-URA) and recombinant OPH+ strains harboring the different promoter-YDsRed fusions
[a]Samples read in duplicate and normalized to $OD_{600}$ and the promoterless empty control vector (pYDsRed-LEU).

Figure 19:
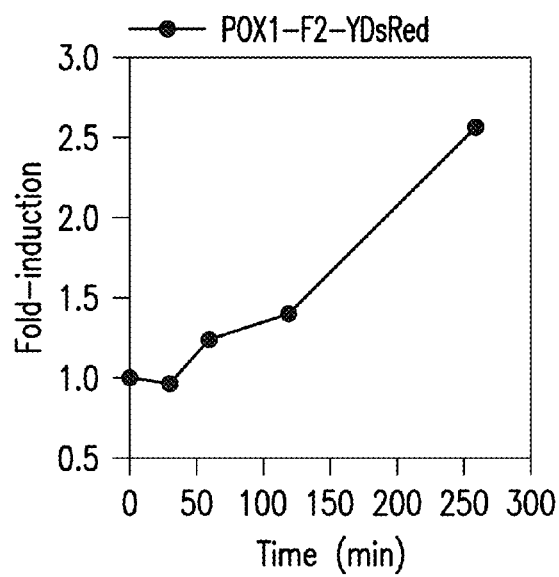
FIG. 19 is a chart illustrating a time course of YDsRed induction in recombinant OPH+ yeast harboring pPDX1-F2-YDsRed in the presence of 3 mM paraoxon.
Figure 20:
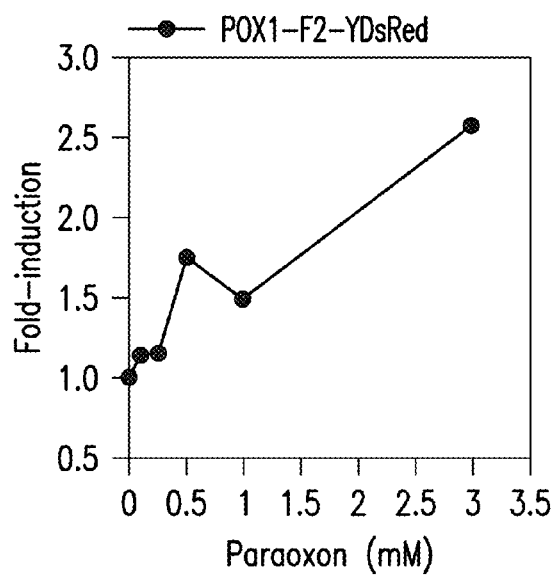
FIG. 20 is a chart illustrating a dose response of YDsRed-induction in *S. cerevisiae* OPH+ harboring pPDX1-F2-YDsRed in the presence of 0.1 to 3.0 mM paraoxon for 255 min.

A time course analysis examining YDsRed induction was performed using the pPDX1-F2 YDsRed fusion construct. YsDsRed fluorescence was measured 30, 60, 120, and 260 min after the addition of paraoxon for recombinant OPH+ cultures harboring the pPDX1-F2-YDsRed fusion (FIG. 19). A steady increase in YDsRed-induction was observed as the exposure time to paraoxon increased. YDsRed fluorescence was induced 2.5-fold after 260 min exposure to paraoxon. To determine the sensitivity of the assay and to investigate whether the recombinant yeast responded to different paraoxon concentrations, a dose response curve was performed. S. cerevisiae OPH+ harboring pPDX1-F2-YDsRed was incubated with 0.1, 0.25, 0.5, 1.0, and 3 mM paraoxon for 255 min prior to assaying for YDsRed fluorescence. As the concentration of paraoxon increased, YDsRed-induction increased, albeit modestly (FIG. 20). Therefore, the results suggest that the yeast biosensor exhibited dose response characteristics to paraoxon hydrolysis.

The fluorescent protein DsRed was chosen for these experiments since: (i) it has been successfully used as a reporter protein in yeast (Bevis B J & Glick B S (2002) Nat Biotechnol 20, 83-7); (ii) it is a stable protein and (iii) it emits distinct spectral properties compared to YeGFP; however, the differential level of fluorescence between yeast cultures expressing YDsRed, and background autofluorescence levels (lacking YDsRed) was minimal. The low level of YDsRed expression may be overcome following further experiments and optimization. To overcome this potential limitation and to increase the 'signal to noise ratio', the Vibrio harveyi luxAB reporter genes may be used to create a yeast biosensor that bioluminesces following OP hydrolysis. Bioluminescent yeast displaying similar light intensities to bacterial systems have been generated (Szittner R et al., (2003) Biochem Biophys Res Commun 309, 66-70). Since yeast cells do not naturally bioluminesce, bioluminescent signals approaching 900.000-fold above background levels have been achieved (Gupta R K et al., (2003) Fems Yeast Res 4, 305-13). In addition, the use of a 'transient' luminescent signal (as opposed to a stable YDsRed fluorescent protein) may enable the detection of increases and decreases in light emission. Consequently, a bioluminescent signal may be more suitable for monitoring the decontamination process.

Recombinant OPH+ yeast cells harboring promoters associated with paraoxon hydrolysis and fused to YDsRed, displayed between 2.5- to 8-fold YDsRed-induction levels in the presence of paraoxon. YDsRed induction was not observed in wild-type yeast cells (lacking OPH) suggesting that YDsRed induction was strictly associated with paraoxon hydrolysis. YDsRed induction increased with higher paraoxon concentrations indicating that the yeast biosensor responded to the amount of paraoxon hydrolyzed.

TABLE 11

Plasmids used and constructed in this study.

| Plasmid name | Host species | Features |
|---|---|---|
| pJK33 | E. coli | Flavobacterium OPD gene |
| pP1-SK | E. coli | E. coli optimized promoter (PI) in pBluescript SK– |
| pPI-SCOPD-SK | E. coli | PI driving OPD with yeast RBS |
| pPI-ECOPD-SK | E. coli | PI driving OPD with E. coli RBS |
| pOPD-OPT-SK | E. coli | Yeast codon optimized OPD in pSKII+ |
| pESC-URA | E. coli/S. cerevisiae | Yeast expression vector/URA marker |
| pSCOPD-ESC-URA | E. coli/S. cerevisiae | GAL1 promoter driving OPD |
| pOPD-OPT-ESC-URA (pYOPD-ESC-URA) | E. coli/S. cerevisiae | GAL1 promoter driving yeast codon optimized OPD |
| pYDsRed-SKII+ | E. coli | Yeast codon optimized DsRed express (YDsRed) |
| pESC-HIS | E. coli/S. cerevisiae | Yeast expression vector/HIS marker |
| pEGFP-NI | E. coli/S. cerevisiae | Mammalian vector containing 'enhanced' GFP |
| pEGFP-ESC-HIS | E. coli/S. cerevisiae | 'promoterless' EGFP reporter plasmid |
| pGAL-EGFP-ESC-HIS | E. coli/S. cerevisiae | pGAL10 driving EGFP |
| pEGFP-YDsRed-ESC-HIS | E. coli/S. cerevisiae | Dual EGFP-YDsRed 'promoterless' reporter plasmid |
| pYeGFP-ESC-HIS | E. coli/S. cerevisiae | 'promoterless' reporter plasmid containing the yeast codon optimized enhanced GFP (YeGFP) |
| pGAL-YeGFP-ESC-HIS | E. coli/S. cerevisiae | pGAL10 driving YeGFP |
| pESC-LEU | E. coli/S. cerevisiae | Yeast expression vector/LEU marker |
| pYDsRed-ESC-LEU | E. coli/S. cerevisiae | 'promoterless' YDsRed reporter plasmid |
| pPOX1-F1-YDsRed-LEU | E. coli/S. cerevisiae | POX1 promoter (1002 bp upstream of ATG) driving YDsRed |
| pPOX1-F2-YDsRed-LEU | E. coli/S. cerevisiae | POX1 promoter (525 bp upstream of ATG) driving YDsRed |
| pYGR287C-F1-YDsRed-LEU | E. coli/S. cerevisiae | YGR287C promoter (993 bp upstream of ATG) driving YDsRed |
| pYGR287C-F2-YDsRed-LEU | E. coli/S. cerevisiae | YGR287C promoter (570 bp upstream of ATG) driving YDsRed |
| pGAL-YDsRed-ESC-LEU | E. coli/S. cerevisiae | pGAL1 driving YDsRed |
| pYGR035C-F1-YeGFP-ESC-HIS | E. coli/S. cerevisiae | YGR035C promoter (991 bp upstream of ATG) driving YeGFP |
| pYGR035C-F2-YeGFP-ESC-HIS | E. coli/S. cerevisiae | YGR035C promoter (455 bp upstream of ATG) driving YeGFP |
| pYLR346C-F1-YeGFP-ESC-HIS | E. coli/S. cerevisiae | YLR346C promoter (973 bp upstream of ATG) driving YeGFP |
| pYLR346C-F2-YeGFP-ESC-HIS | E. coli/S. cerevisiae | YLR346C promoter (476 bp upstream of ATG) driving YeGFP |

TABLE 12

Strains used in this study.

| Species/strain | Genotype | Source | Features |
|---|---|---|---|
| E. coli ER2738 | F'proA+B+lacIqΔ(lacZ)M15zzf.:Tn10(TetR)/fhuA2 glnVΔ(lac-proAB)thi-1Δ(hsdS-mcrB)5 | New England Biolabs | General lab cloning strain |
| S. cerevisiae W3031A | MATa ade2-1 ura3-1 his3-11 trp1-1 leu2-3 leu2-112 can1-100 | Guild stock collection | Wild-type strain |
| S. cerevisiae BY4741 | MATa his3Δ1 leu2Δ0 met15Δ0 ura3Δ0 | Guild stock collection | Wild-type strain |
| S. cerevisiae erg3 | MATa his3Δ1 leu2Δ0 met15Δ0 ura3Δ0 ΔERG3 | ATCC4002667 | erg3 mutant strain |
| S. cerevisiae erg4 | MATa his3Δ1 leu2Δ0 met15Δ0 ura3Δ0 ΔERG4 | ATCC4004380 | erg4 mutant strain |
| S. cerevisiae erg6 | MATa his3Δ1 leu2Δ0 met15Δ0 ura3Δ0 ΔERG6 | ATCC4000568 | erg6 mutant strain |

TABLE 13

Real-time PCR primers used in this study

| Gene | Primers (forward and reverse) | SEQ ID NO | PCR product size (bp) |
|---|---|---|---|
| YGR035C | 5'-GCGTGCCATAGTTTCTTCC | 7 | 169 |
|  | 5'-TCGTCCCTGAGACTTACTC | 8 |  |
| SPS100 | 5'-AGTACCGTGGCATCATGGAC | 9 | 128 |
|  | 5'-GCAGAAATTGCACCTTGTGG | 10 |  |
| YOR186W | 5'-TTTAAGTCCGCCATACGAGC | 11 | 139 |
|  | 5'-CTGCCTACATCGCCAATCAC | 12 |  |
| RTA1 | 5'-AATGGCTACTCTGCTGTTCG | 13 | 87 |
|  | 5'-CTGCCTACATCGCCAATCAC | 14 |  |
| YLR346C | 5'-TGTCCCATCGGGTTAGTTTC | 15 | 161 |
|  | 5'-TGGGCAGCCTTGAGTAAATC | 16 |  |
| MET28 | 5'-AAGCAGGAAGGGTATGAACG | 17 | 100 |
|  | 5'-CAGCAGCAATGATAGCAAGC | 18 |  |
| YLL056C | 5'-CAGCAGCAATGATAGCAAGC | 19 | 189 |
|  | 5'-CGGTCAATTTCGCAGCACTG | 20 |  |
| POX1 | 5'-AAGCTGCTCTGGTTACCGTG | 21 | 134 |
|  | 5'-ATACCCATGTCCTCCGCAAG | 22 |  |
| HXT9 | 5'-AAGTTGTGGCCTCAAGGAAG | 23 | 183 |
|  | 5'-TGTTGCGATTGCCATTCCTC | 24 |  |
| YGR287C | 5'-ACTTGGCAATCCAGTGATCC | 25 | 140 |
|  | 5'-TCGGAGGCATGTTGCATTTC | 26 |  |
| YHL012W | 5'-TTGCCTTCTTTCCGAACAGT | 27 | 173 |
|  | 5'-GCCCAAGTCGATTGAAGGTA | 28 |  |
| ACT1 | 5'-TTCCAGCCTTCTACGTTTCC | 29 | 100 |
|  | 5'-ACGTGAGTAACACCATCACC | 30 |  |

TABLE 14

PCR primers used in promoter fragment cloning procedures

| Gene | Primers (2 forward and 1 reverse) | SEQ ID NO | PCR product size (bp) |
|---|---|---|---|
| YGR035C | 5'-TTAAGTCGACAGAGTTTACTTGCACTACC | 31 | 991 |
|  | 5'-TTAAGTCGACGGAGATAATACCCTCTG | 32 | 455 |
|  | 5'-AATTGGATCCTACGTATTGTTTCTGTAGAG | 33 |  |
| YLR346C | 5'-AATTGTCGACTTTCTTCCTTTTCTACTATC | 34 | 973 |
|  | 5'-TTAAGTCGACCAACCATCCTTAGCTTCC | 35 | 476 |
|  | 5'-TTATGGATCCTATTAAAGGTGATAAATAATCC | 36 |  |
| POX1 | 5'-AATTGTCGACTTTCACTCAACCACCTCC | 37 | 1002 |
|  | 5'-TATAGTCGACTAGATTCCTTCAGTTCCAC | 38 | 525 |
|  | 5'-TTAAGGATCCATCGCAATACTAATTTATTATAT | 39 |  |
| HXT9 | 5'-TTAAGTCGACACTTGGGTTCTGTTTCTGG | 40 | 1000 |
|  | 5'-ATTAGTCGACATACGGAGCGTAAACAACC | 41 | 583 |
|  | 5'-ATATGGATCCGATATTGGGTAAGATACGAA | 42 |  |

TABLE 14-continued

PCR primers used in promoter fragment cloning procedures

| Gene | Primers (2 forward and 1 reverse) | SEQ ID NO | PCR product size (bp) |
|---|---|---|---|
| YLR287C | 5'-TTAAGTCGACGGCTGTATGTTTATGATTGC | 43 | 993 |
| | 5'-TTAAGTCGACGCTCTTAACTGCGTTTACC | 44 | 570 |
| | 5'-TTAAGGATCCGATAGTAAATATTACGTTGA | 45 | |
| YHL012W | 5'-TATTGTCGACGCCTCTTCTTTCATTTTAGC | 46 | 1000 |
| | 5'-ATTAGTCGACATTAGATGCTTTCGAGATGC | 47 | 523 |
| | 5'-TAATGGATCCTGATCTTGTATATACTATGTAG | 48 | |

Bold indicates the BamHI or SalI restriction site for cloning into the corresponding sites of YeGFP-His or YDsRed-LEU.
Underlined sequence designates the homologous complementary sequence.

TABLE 15

Organophosphate Degrading Enzymes

| Species/source | Genename/ abbreviation | Enzyme name | Genbank accession number |
|---|---|---|---|
| Flavobacterium | Organophosphate degrading (opd) | Organophosphorus hydrolase (OPH) | M29593 |
| Pseudomonas diminuta | opd | Phosphotriesterase | M20392 |
| Agrobacterium tumefaciens | opdA | OpdA | AY043245 |
| Alteromonas | OpaA | Organophosphorus acid anhydrolase (OPAA) | ASU29240 U56398 |
| Loligo vulgaris (squid) | | DFPase | |
| Mammalian | PON | Paraoxonase (PON) | NM 000446 NM 001013082 NM 032077 NM 183308 NM 173006 NM 011134 NM 000940 XM 418669 |

TABLE 16

Organophosphate degrading enzymes hydrolyze (detoxify) different bonds within the different organophosphates

| | Bond cleaved by enzyme | | | | |
|---|---|---|---|---|---|
| Enzyme | P—C | P—O | P—F | P—S | P—CN |
| OPH | | + | + | + | + |
| OPAA | − | + | + | − | + |
| PON | + | + | + | + | + |
| DFPase | | − | + | − | |

TABLE 17

OPH cleaves the following organophosphate nerve agents and pesticides by hydrolyzing the designated bond.

| Organosphosphate | Bond type |
|---|---|
| Nerve agent | |
| VX | P—S |
| Sarin | P—F |
| Soman | P—F |
| Tabun | P—CN |
| Pesticide | |
| Paraoxon | P—O |
| DFP* | P—F |
| Parathion | P—O |
| Methyl parathion | P—O |
| Coumaphos | P—O |
| Diazinon | P—O |
| Fensulfothion | P—O |
| Acephate | P—S |
| Demeton-S | P—S |
| Phosalone | P—S |
| Malathion | P—S |

*DFP, diisopropyl fluorophosphate

Example 15

Mutagenesis Strategy

The OP pesticides demeton-S methyl and malathion were used in an initial screening process to minimize safety and laboratory issues associated with VX. Without limiting any specific embodiment to a particular theory or mechanism of action, it was believed that variant enzymes with increased hydrolytic activity toward demeton-S methyl and/or malathion would also display increased hydrolytic activity toward VX because demeton-S methyl and malathion, like VX, are hydrolyzed at a P—S bond.

Specific amino acids have been identified that are associated with increased expression of the OPH protein, namely K185R, D208G, and R319S. In addition, specific amino acids have been identified that are associated with increased hydrolytic activity against different OP compounds, namely A80V and I274N. Accordingly, these changes were introduced into OPH by site directed mutagenesis. The specific activity of lysates prepared from cells harboring a plasmid-borne copy of the mutated opd gene was significantly higher than the wild-type for both demeton-S methyl and malathion (Table 18). Consequently, this variant gene was used as the starting template for saturation mutagenesis at the active site residues.

Example 16

Mutagenesis

Mutagenesis was performed using the plasmid pPI-OPD-SK− as template which contains: (i) the *Flavobacterium* spp. organophosphate degrading (opd) gene lacking the first 33 residues for enhanced activity in *E. coli*, and (ii) a strong consensus *E. coli* promoter and ribosome binding site for efficient expression in *E. coli*. Site-directed mutagenesis incorporating specific nucleotide changes and saturation mutagenesis of specific codons was performed using the QuikChange site-directed kit and the QuikChange Multi-site directed mutagenesis kit, respectively according to the manufacturers' instructions (Stratagene) using the oligonucleotides described in Table 19. Mutagenized plasmids were transformed into *E. coli* ER2738. A mutation efficiency of 60% was routinely produced. The identity of the specific changes were confirmed by DNA sequencing.

Example 17

Whole Cell *E. coli* Screening Assays

*E. coli* colonies, harboring an empty plasmid control, the wild-type (pP1-ECOPD-SK−), or mutagenized plasmids were grown overnight in Luria Bertani (LB) broth supplemented with 100 µg/mL ampicillin at 37° C. Saturated overnight cultures were diluted 1:100 in fresh media (3 mL) and grown for 3 h at 37° C. After an additional 60 min incubation in the presence of 50 µM $CoCl_2$ and 0.1 mM IPTG, the cultures were harvested by centrifugation (8,000×g, 5 min), washed with 50 mM HEPES pH 7.5, and resuspended in 100 µL of the same buffer. An aliquot (25 µL) of the resulting cell suspension was analyzed for the ability to hydrolyze demeton-S methyl (Chemservice) or malathion (Cerilliant). Reactions consisted of 50 mM HEPES buffer pH 7.5, 0.5 mM DTNB (Ellman's reagent, 5',5'-dithiobis(2-nitrobenzoic acid)) (Ellman, 1961, *Biochem Pharmacol* 7:88-95) and either 1 mM demeton-S methyl or 0.4 mM malathion. The rate of hydrolysis was measured by following the appearance of 2-nitro-5-thiobenzoate at 412 nm at RT (~25° C.) using a BioTek Synergy 2 microplate reader. Results were normalized to the $OD_{600}$ of the assay mix. Approximately 100 colonies were screened for each round of amino acid saturation. Putative *E. coli* clones displaying an increased ability to hydrolyze demeton-S methyl or malathion were rescreened in triplicate before proceeding to the lysate assays.

Example 18

Cell Lysate Assays

*E. coli* cells harboring the different constructs were prepared as described above (Example 17) except the cultures were grown for an additional hour before the addition of 50 µM $CoCl_2$ and 0.1 mM IPTG. Cultures were harvested at an $OD_{600}$ of 0.6. Enzyme lysates were prepared by incubating the cells with Y-MER dialyzable lysis buffer (Pierce Biotechnology) for 20 min at room temperature (RT), followed by centrifugation at 24,000×g for 15 min. The ability of cytosolic enzyme to hydrolyze demeton-S methyl or malathion was assessed as described above using ~250 µg of enzyme extract. Control enzymatic hydrolysis reactions lacking OPH were measured and subtracted from enzymatic hydrolysis rates. Each clone was measured using triplicate lysates prepared from triplicate cultures and the specific activity was measured as µmoles hydrolyzed/min/mg protein.

Example 19

Protein Expression and Purification

To prepare the wild-type opd (gene encoding the wild-type OPH) and variant sequences for cloning into a protein overexpression vector, the plasmids were digested with BamHI/EcoRI which dropped out the ribosome binding site and the opd ATG start codon. This small fragment was replaced with an oligonucleotide containing BamHI/EcoRI overhang ends and the 5' end of opd (5'-gatccatgaccatgattacg) but lacking a designated ribosome binding site. Cloning and propagation was performed using *E. coli* ER2738 as the host. The coding sequences were then cloned into the BamHI/HindIII sites of the protein overexpression vector pET-30a (Novagen). This cloning strategy ensured that opd was cloned in frame with the His-Tag sequence and the vector ribosome binding site was used to initiate translation of the fused protein (N-terminal fusion). The wild-type and variant opd expression plasmids were transformed into *E. coli* BL21(DE3)pLysS (Novagen). Cultures were grown in LB supplemented with 50 µg/mL kanamycin and 50 µg/mL chloramphenicol until an $OD_{600}$ of 0.5, and then incubated in the presence of 1 mM IPTG for 120 min before harvesting. One mL aliquots of the cultures were lysed in SDS-PAGE sample buffer and boiled for 5 min. Cell lysates were applied to a 12% SDS-PAGE gel, electrophoresed using the Laemmli buffer system, and stained using silver nitrate. A clear band of the correct size (~40 kD) was evident in lysates prepared from *E. coli* BL21 (DE3)pLysS harboring the wild-type plasmid but absent in lysates prepared from cells lacking IPTG (non-inducing conditions) or from control cells (data not shown). The remainder of the culture (~50 mL) was used for the extraction of the wild-type and OPH variants using the Ni-NTA purification system (Invitrogen) for the purification of polyhistidine-containing recombinant proteins. Following cell lysis, the resulting aqueous fraction was passed across a Nickel agarose affinity column. The column was washed with 50 mM sodium phosphate buffer (pH 8.0), 0.5 M NaCl, 30 mM imidazole, and the protein eluted with 50 mM sodium phosphate buffer (pH 8.0) containing 0.5 M NaCl and 250 mM imidazole. Aliquots from flowthrough, wash, and elution were be taken for SDS-PAGE analysis to monitor each purification step. Recombinant protein was concentrated using Ultra 4 centrifugal concentraters, and quantified by the Bradford dye binding assay. Purity was estimated by SDS-PAGE with 3 concentrations of an internal quantification standard.

Example 20

Enzyme Kinetics

The kinetic constants ($K_M$ and $k_{cat}$) for the wild-type, G60V, I106V, F306V and S308L for demeton-S methyl and malathion were determined. The assays were performed using the conditions described above except DTNB was used at a final concentration of 10 µM. Different substrate and enzyme concentrations were tested to determine the most robust kinetic parameters possible for each variant. The $K_M$ and $k_{at}$ values were obtained by fitting the data to Lineweaver-Burk reciprocal plots and Hanes-Woolf plot. Similar data was obtained by both methods. The data presented represents the data obtained from the Hanes-Woolf plot.

Example 21

VX Hydrolysis Assays

The VX assays were performed at a suitable testing and containment facility. VX P—S bond cleavage was detected using Ellman's reagent essentially as described previously (Gopal, 2000, Biochem Biophys Res Commun 279:516-9). Assay conditions consisted of 0.5 mM VX, 10 mM TAPS (pH 8.0), purified enzyme (~5-15 μg), 5 mM HEPES (pH 7.5), 100 μM $CoCl_2$, and 1 mM DTNB. Thiol release was measured at 412 nm at room temperature. Non-enzymatic reaction rates were also measured and subtracted from the enzymatic rates.

Example 22

AChE Hydrolysis Assays

To demonstrate that the wild-type and S308L OPH variant hydrolyzed, and thereby detoxified demeton-S methyl, AChE assays were performed. Triplicate aliquots of the hydrolysis assays (after 0, 2, 3, 4, 6 and 9 h incubation) were mixed with purified human AChE (8.56 nM) for 30 min at RT. Demeton-S methyl controls (in reaction buffer) lacking OPH enzyme and AChE positive controls were run in parallel. The AChE assay mix was then diluted and mixed with the substrate, acetylcholine (ACh, 0.5 mM), and 0.5 mM DTNB in 100 mM sodium phosphate buffer (pH 7.4). Absorbance changes due to ACh hydrolysis were monitored at 412 nm every 2 min for 30 min and the slope of the regression line of the reaction was used for calculating percentage inhibition.

Example 23

Results

Saturation mutagenesis was sequentially performed at active site residues H257, H254, W131, F132, C59, I106, L271, G60, L303, Y309, M317, S61, F306, and S308 (Example 16) followed by screening against both malathion and demeton-S methyl. Randomization mutagenesis of a single amino acid enabled screening of all possible permutations of the 20 amino acids at that site. Approximately 100 colonies for each round of mutagenesis, each harboring a plasmid-borne copy of the mutated opd gene, were initially screened using a whole cell assay (Example 17). Colonies that displayed an increased ability to hydrolyze the OP agent were rescreened in triplicate, and further rescreened using cell lysates (Example 18). This process was sequentially repeated for each amino acid using (when applicable) the previously identified improved variant as the starting template in order to potentially progressively improve the activity of the variant after each round of screening. This saturation mutagenesis identified amino acid changes of H257W, F132C, F132D, I106V, G60V, F306V and S308L, which increased the specific activity of cell lysates against demeton-S methyl or malathion, or against both OP substrates (Table 18). In most cases however, changes at a specific amino acid increased the activity against one of the substrates, but decreased the activity against the other substrate. For example, the H257W mutation increased the specific activity of the lysate against demeton-S methyl 3-fold, but was approximately 2-fold less active against malathion, compared to the parental lysates. Nevertheless, the specific activity of all the lysates were significantly increased against both malathion and demeton-S methyl compared to the wild-type lysates. The protein sequences of wild-type and variant OPH enzymes are presented in FIG. 21. In this figure, the 'Wild-type' OPH is the lacZ-OPD fusion from plasmid pJK33 as described in Mulbry and Karns, 1989: J. Bacteriology 171: 6740-6746). (the first five codons of lacZ were fused to the opd codon (at the codon Gly), thus deleting the 29-residue signal peptide along with the first four residues of the native mature protein).

Increases in the specific activities of the variant lysates may be due to changes in the expression, solubility, stability and/or activity of the variant proteins. Therefore, the wild-type and variant OPH proteins identified in Table 18 were purified and the specific activities against demeton-S methyl and malathion were measured (Table 20). The specific activities of the purified variants I274N, H257W, F132D, and F132C were similar to the wild-type and suggests that the observed changes in the corresponding cell lysates were not due to an increase in the activity of the protein. This is probably not surprising since at least some of the incorporated amino acid changes (K185R, D208G, and R319S) may increase the solubility of the protein. In contrast, the specific activities of the I106V, G60V, F306V, and S308L variants were significantly increased compared to the wild-type (Table 20). In particular, the specific activity of the S308L variant was improved 35- and 42-fold against malathion and demeton-S methyl, respectively, compared to the wild-type.

The variant enzymes G60V, I106V, F306V and S308L exhibited the greatest improvement in the specific activity against demeton-S methyl and malathion compared to the wild-type enzyme (Table 20, up to 77-fold). Therefore, the kinetic constants ($K_M$ and $K_{cat}$) for the wild-type, G60V, I106V, F306V and S308L for demeton-S methyl and malathion were determined (Example 20). The catalytic rates ($k_{at}$) of all the variants against demeton-S methyl were improved compared to the wild-type enzyme (Table 21). In particular, the $k_{cat}$ values for S308L, G60V, and I106V increased 3.5 to 5.3-fold compared to the wild-type enzyme. The $K_m$ for G60V, however, was much higher than for the wild-type enzyme resulting in very similar specificity constant to the wild-type enzyme ($k_{cat}/K_m$). In contrast, the $K_m$ values for I106V and S308L were much lower than the wild-type enzyme. Thus, the specificity constant of I106V and S308L were improved 11.7- and 24.7-fold, respectively, for demeton-S methyl compared to the wild-type enzyme. The specific constant for the wild-type enzyme is in agreement with other reports.

The kinetic constants of the wild-type, G60V, I106V, F306V and S308L against malathion were determined (Table 21). The catalytic rates ($k_{cat}$) of all the variants against malathion were improved compared to the wild-type enzyme, while the Michaelis constants, with the exception of F306V, were slightly higher than the wild-type enzyme. The specificity constants for all the variants were improved compared to the wild-type enzyme with the greatest increase of 25-fold for the F306V variant. The variant with the greatest improvement in the specificity constant for both demeton-S methyl and malathion was S308L.

To demonstrate that the variant OPH enzymes have increased efficiency against VX, the specific activity of the variant OPH enzymes and wild-type enzyme towards VX was determined (Table 22). The prioritized variants I106V, F306V, and S308L were chosen since they displayed the greatest increase in activity against both demeton-S methyl and malathion. The F306V variant, which displayed a 77-fold improvement in the specific activity against malathion, exhibited only ~10% of the specific activity against VX compared to the wild-type enzyme. This suggests that the improved (both $k_{cat}$ and $K_m$) ability of F306V to hydrolyze malathion is not a good predictor for increased activity against VX. In contrast, the specific activities of I106V and S308L against VX were improved 8- and 26-fold, respectively, compared to the wild-type enzyme. Therefore, 2 variant enzymes, with significantly improved activity against VX compared to the wild-type, were generated.

Figure 22:
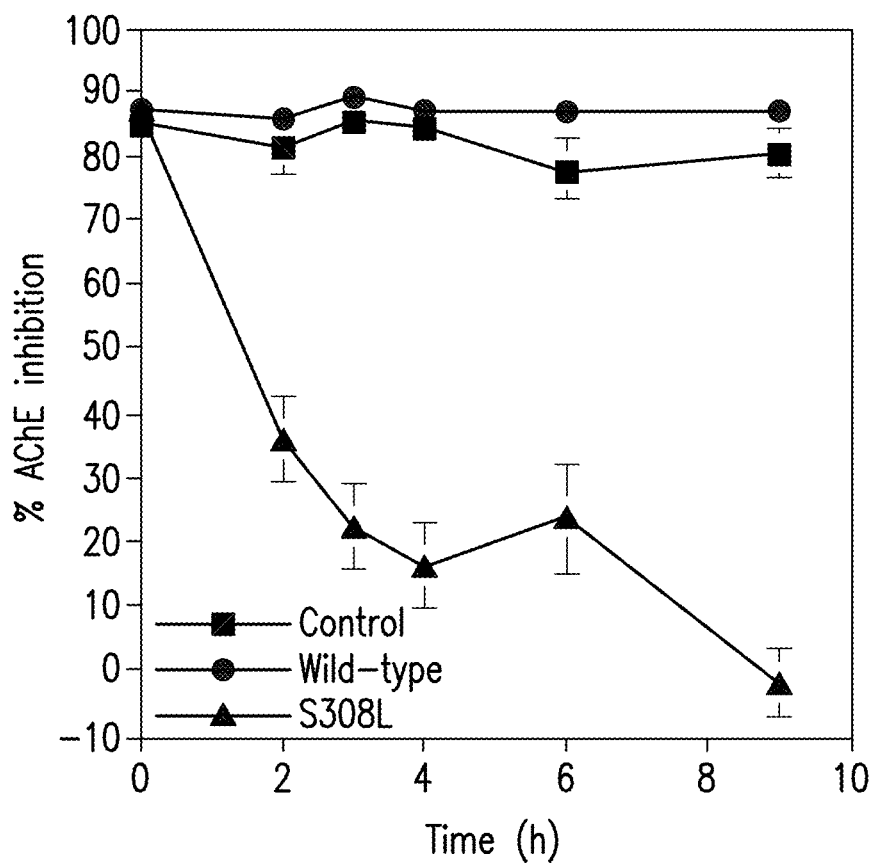
FIG. 22 is a chart illustrating the relative ability of wild-type OPH and a variant OPH to detoxify dementon-5-methyl in an AchE assay (readings represent the mean and SD of three assays.)

OP compounds act by inhibiting the enzyme acetylcholinesterase (AChE). To confirm the S308L variant activity resulted in an improved ability to reduce OP toxicity compared to the wild-type enzyme, samples from the demeton-S methyl hydrolysis assays were analyzed for a reduction in the ability of the OP agent to inhibit AchE (Example 22). Briefly, demeton-S methyl hydrolysis assays were performed in the absence of enzyme (control), or in the presence of wild-type OPH or the variant S308L. After varying incubation periods, the ability of demeton-S methyl to inhibit AChE was measured. The S30L-mediated reduction in AChE activity is directly indicative of the reduced toxicity of the OP agent. Over the time period analyzed (9 h), there was no difference in AChE activity between control (demeton-S methyl) and wild-type samples (FIG. 22). In contrast, over the same time period, the S308L resulted in near complete detoxification of demeton-S methyl. The results confirmed the improved ability of S308L to hydrolyze demeton-S methyl compared to the wild-type enzyme.

Perhaps due to the limitations, restrictions and safety concerns of using the chemical warfare agent VX, applicants are aware of only 1 original report and 1 review describing the generation of a mutated OPH enzyme with improved activity against VX. In the review paper, DiSioudi et al. (1999, *Chem Biol Interact* 119-120:211-23) generated a H254R and H257L OPH mutant, which displayed a 4 to 5-fold improvement in activity against VX, although no data was presented. Gopal et al. (2000, *Biochem Biophys Res Commun* 279:516-9) generated a L136Y OPH mutant (based on rational design between the crystal structure of OPH and its similarities to acetylcholinesterase), which displayed a 33% increase in the relative VX hydrolysis rate compared to the wild-type enzyme. Although the Gopal et al. report tested a number of different OP compounds as possible surrogates to VX (paraoxon, demeton-S methyl, EPN, ethyl parathion, and DFP), a direct relationship between VX hydrolysis rates and the hydrolysis rates of these OP compounds was not evident, and the conclusion was that none of them were a valid surrogate. The results presented here suggest that there was no correlation between the ability to hydrolyze malathion and the ability to hydrolyze VX since the specific activity of F306V was improved over 70-fold against malathion compared to the wild-type while the same enzyme against VX was approximately 10-fold lower than the wild-type. In contrast, the variant enzymes (I106V and S308L), which displayed increased hydrolysis of demeton-S methyl, also displayed increased hydrolysis of VX (up to 26-fold) compared to the wild-type and suggests that there was a good correlation between hydrolysis of demeton-S methyl and VX. To the best of our knowledge, this represents a significant advancement in the ability of the OPH enzyme to hydrolyze VX. Such improvements represent an important contribution to the success of bioremediation strategies.

TABLE 18

Specific activities of lysates against demeton-S methyl and malathion

| OPH | Name | Specific activity$^{abc}$ Demeton-S methyl | Malathion |
|---|---|---|---|
| Wild-type | OPH | $1.5 \times 10^{-4}$ ($0.9 \times 10^{-4}$)$^{(n=18)}$ | $0.8 \times 10^{-5}$ ($1.7 \times 10^{-5}$)$^{(n=6)}$ |
| A80V.K185R.D208G.I274N.R319S | I274N | $15.1 \times 10^{-4}$ ($3.3 \times 10^{-4}$)$^{(n=6)}$ | $47.7 \times 10^{-5}$ ($1.5 \times 10^{-5}$)$^{(n=3)}$ |
| A80V.K185R.D208G.H257W.I274N.R319S | H257W | $50.9 \times 10^{-4}$ ($27.6 \times 10^{-4}$)$^{(n=6)}$ | $22.4 \times 10^{-5}$ ($11.9 \times 10^{-5}$)$^{(n=6)}$ |
| A80V.F132D.K185R.D208G.H257W.I274N.R319S | F132D | $194.0 \times 10^{-4}$ ($115.3 \times 10^{-4}$)$^{(n=6)}$ | $45.0 \times 10^{-5}$ ($12.9 \times 10^{-5}$)$^{(n=6)}$ |
| A80V.F132C.K185R.D208G.H257W.I274N.R319S | F132C | $267.7 \times 10^{-4}$ ($138.1 \times 10^{-4}$)$^{(n=3)}$ | $19.3 \times 10^{-5}$ ($0.6 \times 10^{-5}$)$^{(n=3)}$ |
| A80V.I106V.F132D.K185R.D208G.H257W.I274N.R319S | I106V | $140.4 \times 10^{-4}$ ($115.3 \times 10^{-4}$)$^{(n=6)}$ | $75.4 \times 10^{-5}$ ($39.3 \times 10^{-5}$)$^{(n=6)}$ |
| G60V.A80V.I106V.F132D.K185R.D208G.H257W.I274N.R319S | G60V | $47.2 \times 10^{-4}$ ($17.4 \times 10^{-4}$)$^{(n=6)}$ | $616.8 \times 10^{-5}$ ($180.3 \times 10^{-5}$)$^{(n=6)}$ |
| G60V.A80V.I106V.F132D.K185R.D208G.H257W.I274N.F306V.R319S | F306V | $42.9 \times 10^{-4}$ ($6.2 \times 10^{-4}$)$^{(n=3)}$ | $1511.3 \times 10^{-5}$ ($226.1 \times 10^{-5}$)$^{(n=3)}$ |
| A80V.I106V.F132D.K185R.D208G.H257W.I274N.S308L.R319S | S308L | $115.9 \times 10^{-4}$ ($73.4 \times 10^{-4}$)$^{(n=5)}$ | $414.4 \times 10^{-5}$ ($272.1 \times 10^{-5}$)$^{(n=5)}$ |

$^a$μmoles hydrolyzed/min/mg total protein after correction from control lysates
$^b$average (standard deviation)(n = number of individual lysates measured)
$^c$p < 0.05 for the variants compared to the wild-type (Student's t test)
"Wild-type" refers to the lacZ-OPD fusion protein described by Mulby and Karns, 1989, J. Bacteriol 171: 6740-6746 (29 amino acid signal peptide deleted and replaced by the first 5 amino acids of lacZ).
The numbering scheme refers to the Flavobacterium OPH protein from GenBank M29593 (SEQ ID NO: 84).

TABLE 19

Opd mutagenesis oligonucleotides

| Oligonucleotide | Amino acid change (from/to) | SEQ ID NO |
|---|---|---|
| 5'-gagttagtgttaaGggcggccgcccgg | Lys185Arg | 49 |
| 5'-gcaagtcagcgcgGtggtgagcagcag | Asp208Gly | 50 |
| 5'-gacgtgatggatAgcgtgaacccgac | Arg319Ser | 51 |
| 5'-gccctcctgggcaAccgttcgtgcaaac | Iso274Asp | 52 |
| 5'-cgcaaagctctagTggaaaaggctgtg | Ala80Val | 53 |
| 5'-gaccacatcccgNNNagtgcgattggtc | His257X | 54 |
| 5'-gaccggcttgtggNNNacccgccactttc | Phe132X | 55 |
| 5'-tgtcgactttcgatNNNggtcgcgacgtc | Iso106X | 56 |
| 5'-cgaccggcttgNNNttcgacccgcc | Trp131X | 57 |
| 5'-tcatcggtctagaNNNatcccgtggagtg | His254X.His257Trp | 58 |
| 5'-actcacgagcacatcNNNggcagctcggcag | Cys59X | 59 |
| 5'-cgagtgcatcagccNNNctgggcaaccgttc | Leu271X | 60 |
| 5'-tcgaatgactggNNNttcgggttttcg | Leu303X | 61 |
| 5'-gggttttcgagcNNNgtcaccaacatc | Tyr309X | 62 |
| 5'-catcatggacgtgNNNgatagcgtgaacc | Met317X | 63 |
| 5'-gagcacatctgcNNNagctcggcagg | Gly60X | 64 |
| 5'-gctgttcgggNNNtcgagctatgtc | Phe306X | 65 |
| 5'-tgttcgggttttcgNNNtatgtcaccaacatc | Ser308X | 66 |
| 5'-cacatctgcgtcNNNtcggcaggattc | Gly60Val.Ser61X | 67 |

CAPITOL/bold indicates the nucleotide change from the wild-type opd sequence (GenBank accession number M29593)(SEQ ID NO: 84).
Number represents the amino position in the wild-type OPH protein.
N, represents either of the 4 possible nucleotides, G, A, T, or C.
X, represents a degenerate codon for any of the possible 20 amino acids.

TABLE 20

Specific activities of purified OPH and variant proteins against demeton-S methyl and malathion

| | Specific activity[b,c] | | | |
|---|---|---|---|---|
| OPH[a] | Demeton-S methyl | Fold-increase to wt | Malathion | Fold-increase to wt |
| Wild-type | 0.033 (0.002) | n/a | 0.019 (0.001) | n/a |
| I274N[a] | 0.016 (0.001) | 0.48 | 0.032 (0.001) | 1.68 |
| H257W[a] | 0.032 (0.001) | 0.97 | 0.007 (0.001) | 0.37 |
| F132D[a] | 0.210 (0.002) | 6.36 | 0.041 (0.001) | 2.16 |
| F132C[a] | 0.061 (0.002) | 1.85 | 0.006 (0.001) | 0.32 |
| I106V[a] | 0.890 (0.065) | 26.97 | 0.115 (0.003) | 6.05 |
| G60V[a] | 0.049 (0.001) | 1.49 | 0.293 (0.014) | 15.4 |
| F306V[a] | 0.139 (0.002) | 4.21 | 1.469 (0.034) | 77.31 |
| S308L[a] | 1.172 (0.013) | 35.51 | 0.794 (0.016) | 41.80 |

[a]Abbreviated amino acid change. Full list of changes in Table 18
[b]µmoles hydrolyzed/min/mg protein
[c]average of three replicates (standard deviation)

TABLE 21

Kinetic parameters of the OPH enzymes against demeton-S methyl and malathion[a]

| Compound | OPH | $k_{cat}$ (s$^{-1}$) | $K_m$ (mM) | $k_{cat}/K_m$ (mM$^{-1}$s$^{-1}$) |
|---|---|---|---|---|
| Demeton-S methyl | Wild-type | 13.16 | 8.09 | 1.63 |
| | I106V[b] | 69.44 | 3.64 | 19.08 |
| | G60V[b] | 45.95 | 23.31 | 1.97 |
| | F306V[b] | 14.62 | 4.18 | 3.50 |
| | S308L[b] | 48.27 | 1.20 | 40.23 |
| Malathion | Wild-type | 2.55 | 0.41 | 6.21 |
| | I106V[b] | 23.01 | 1.16 | 19.83 |
| | G60V[b] | 40.63 | 0.82 | 49.54 |
| | F306V[b] | 44.92 | 0.29 | 154.91 |
| | S308L[b] | 73.29 | 0.67 | 109.39 |

[a]coefficient of variation between the individual replicates was on average 5.5%
[b]Abbreviated amino acid change. Full list of changes in Table 18

TABLE 22

Specific activities of purified wild-type OPH and OPH variants against VX

| OPH | Specific activity[b,c] | Fold increase compared to wild-type |
|---|---|---|
| Wild-type | 0.097 (0.006) | n/a |
| I106V[a] | 0.803 (0.012)[d] | 8.3 |
| F306V[a] | 0.007 (0.006) | 0.1 |
| S308L[a] | 2.500 (0.130)[d] | 26.0 |

[a]Abbreviated amino acid change. Full list of changes in Table 18
[b]µmoles VX hydrolyzed/min/mg protein
[c]average of three replicates (standard deviation)
[d]Significant increase compared to the wild-type (p < 0.05, Student's t-test)
n/a, not applicable

Example 24

Summary

The S308L variant was integrated into the yeast genome by homologous recombination to generate a stable yeast biocatalyst. The recombinant yeast S308L produced functional enzyme capable of hydrolyzing and detoxifying the organophosphates demeton-S methyl and malathion. Yeast S308L lysates hydrolyzed demeton-S methyl approximately 100- fold faster than wild-type OPH lysates. In addition, intact S308L yeast cells were able to hydrolyze and detoxify demeton-S methyl and malathion and function as a biocatalyst. The ability of the yeast biocatalyst to hydrolyze demeton-S methyl translated to the ability to hydrolyze the chemical warfare agent VX.

Example 25

Generation of a Stable Yeast Biocatalyst

Figure 23:
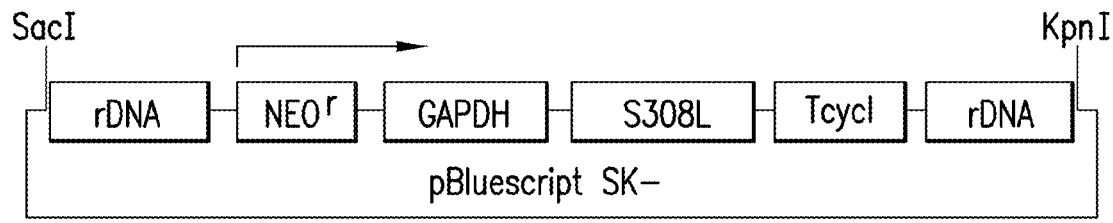
FIG. 23 is a schematic of the S308L integration/expression cassette in pBluescript SK−.

In order to generate an efficient yeast biocatalyst, the variant S308L encoding gene was integrated into the yeast chromosome. An integration/expression cassette consisting of a yeast codon optimized variant S308L gene (SEQ ID NO:77), NEO resistance gene (SEQ ID NO:78), the GAPDH promoter (SEQ ID NO:79), and the TcycI transcriptional terminator (SEQ ID NO:80) was constructed (FIG. 23). The expression cassette was flanked at the 5' (SEQ ID NO:81) and 3' (SEQ ID NO:82) end by yeast rDNA sequence to allow targeted homologous recombination at the rDNA locus between the 5S and 18S subunits (located on chromosome XII). Since there are approximately 140 copies of the rDNA unit, integration at this site has yielded recombinant strains with a similar number of integrated sequences (Lopes, T. S., J. Klootwijk, A. E. Veenstra, P. C. van der Aar, H. van Heerikhuizen, H. A. Raue, and R. J. Planta. 1989. High-copy-number integration into the ribosomal DNA of *Saccharomyces cerevisiae*: a new vector for high-level expression. Gene 79:199-206). A similar integration cassette was constructed for the wild-type codon-optimized OPD gene.

*S. cerevisiae* BY4741 (MATa his3D1 leu2DO met15DO ura3DO) was transformed with the integrations cassettes using a high-efficiency LiAc/PEG yeast transformation method (Gietz, R. D., and R. H. Schiestl. 2007. High-efficiency yeast transformation using the LiAc/SS carrier DNA/PEG method. Nat Protoc 2:31-4). The transformation mixes were plated onto YPD plates supplemented with 200 μg/ml G418 to select for NEO$^r$ colonies. After incubation at 30° C. for 72 to 96 h, NEO$^r$ colonies were restreaked onto master plates. PCR analysis was used to confirm that the S308L and opd genes were integrated into the yeast genome, and at the predicted chromosomal location. The number of S308L gene copies within the recombinant yeast strain was determined by quantitative real time PCR to be between 25 and 34.

Example 26

OP Hydrolysis Assays

*S. cerevisiae* BY4741 (control cells), OPD (wild-type OPH), and S308L (optimized variant) were grown in YPD media (+/−G418 when appropriate) supplemented with 0.1 mM CoCl$_2$ at 30° C. at 225 rpm until an OD$_{600}$ of between 0.6 to 0.8 was reached. The yeast cells were harvested by centrifugation (10,000×g, 2 min), washed with 35 mM HEPES pH 8.0, and the cell pellets were stored frozen at −70° C. until used. Yeast protein lysates were prepared by incubating the cells with 0.5 mL Y-MER dialyzable lysis buffer (Pierce Biotechnology) for 20 min at room temperature (RT), followed by centrifugation at 24,000×g for 10 min at 4° C. The ability of yeast lysates to hydrolyze demeton-S methyl or malathion were measured in reactions consisting of 50 mM HEPES pH 7.5, 1.0 mM DTNB (Ellman's reagent), 0.1 mM CoCl$_2$ and either 1 mM demeton-S methyl or 0.4 mM malathion. The rate of hydrolysis was measured by following the appearance of 2-nitro-5-thiobenzoate at 412 nm at RT (~25° C.) using a BioTek Synergy 2 microplate reader. Control rates of hydrolysis from lysates lacking OPH were measured and subtracted from enzymatic hydrolysis rates. Each clone was measured using triplicate lysates prepared from triplicate cultures and the specific activity of yeast lysates to hydrolyze demeton-S methyl or malathion was measured as μmoles hydrolyzed/min/mg protein.

Lysates prepared from yeast cells harboring integrated copies of the wild-type OPD or variant S308L were able to hydrolyze demeton-S methyl and malathion (Table 23). The specific activity of the variant S308L lysates were approximately 100- and 37-fold higher for demeton-S methyl and malathion, respectively, compared to the wild-type lysates. The results indicated that the recombinant yeast generated functional protein.

TABLE 23

Activity of *S. cerevisiae* BY4741 lysates against demeton-S methyl and malathion

| OPH | Specific activity$^{a,b}$ | | Fold-difference compared to wild-type OPD | |
|---|---|---|---|---|
| | Demeton-S methyl | Malathion | Demeton-S methyl | Malathion |
| BY4741.OPD (wild-type) | $1.1 \times 10^{-4}$ ($0.68 \times 10^{-4}$) | $1.0 \times 10^{-4}$ ($0.49 \times 10^{-4}$) | N/A | N/A |
| BY4741.S308L.C33 | $116.8 \times 10^{-4}$ ($0.5 \times 10^{-4}$) | $37.1 \times 10^{-4}$ ($0.1 \times 10^{-4}$) | 106.2 | 37.1 |

$^a$μmoles hydrolyzed/min/mg total protein
$^b$averages of three independent lysates (standard deviation)

Figure 24:
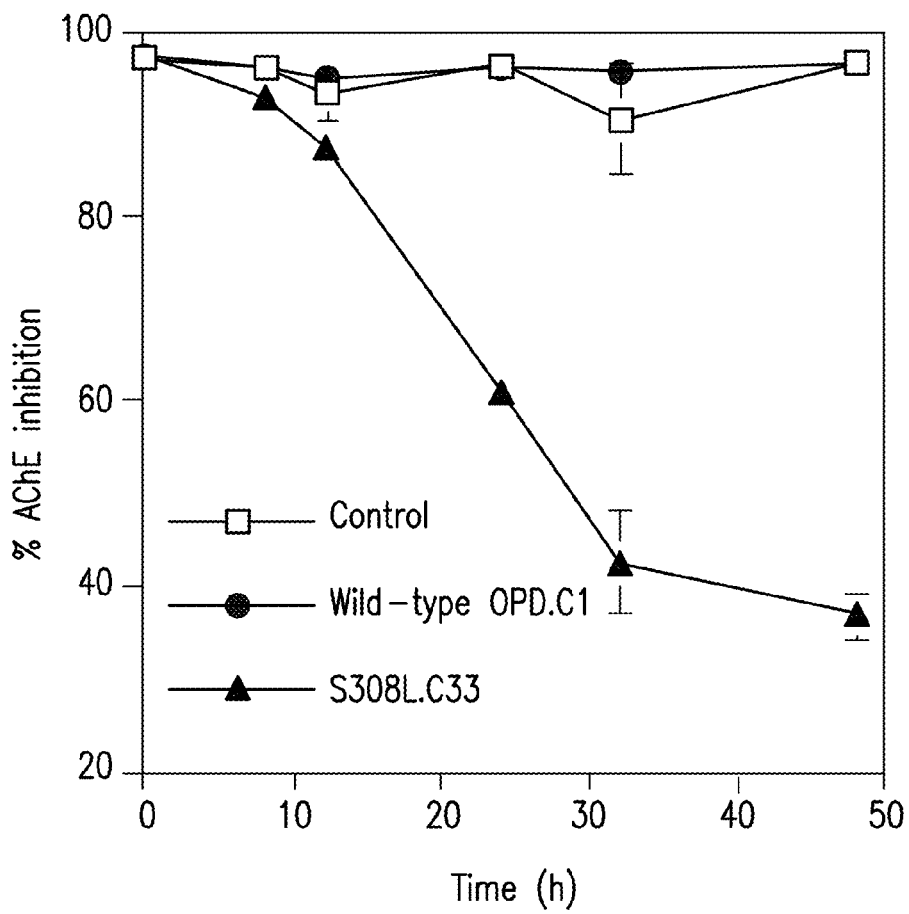
FIG. 24 is a chart illustrating demeton-S methyl detoxification measured by the reduced ability of the OP to inhibit AChE activity.

All OP compounds act by inhibiting the enzyme acetylcholinesterase (AChE). To confirm the S308L yeast lysates hydrolyzed demeton-S methyl and thereby detoxified the OP, samples from the demeton-S methyl hydrolysis assays were analyzed for a reduction in the ability of the OP agent to inhibit AChE. Lysates (10 μg) prepared in triplicate from control (no OPD), wild-type (OPD) or variant S308L yeast and mixed with 50 mM HEPES pH 7.5, 0.1 mM CoCl$_2$, and 50 μM demeton-S methyl. Aliquots of the hydrolysis assays (after 0, 8, 12, 24, 32 and 48 h incubation at 25° C.) were mixed with purified human AChE (8.56 nM) for 30 min at RT. The AChE assay mix was then diluted and mixed with the substrate, acetylcholine iodide (ACh, 0.5 mM), and DTNB (1.0 mM) in 100 mM Na$_2$HPO$_4$ buffer (pH 7.4). Absorbance changes due to ACh hydrolysis were monitored at 412 nm every 2 min for 30 min and the slope of the regression line of the reaction was used for calculating percentage AChE inhibition. The S308L-mediated reduction in AChE activity is directly indicative of the reduced toxicity of the OP agent. Readings represent the mean and SD of three independent lysates. AChE inhibition was approximately 95% for lysates prepared from control and wild-type (OPD) yeast over the time period analyzed (FIG. 24). After varying incubation periods at 25° C., the ability of demeton-S methyl to inhibit AChE was measured.

Therefore, these lysates were unable to prevent demeton-S methyl from inhibiting AChE activity. In contrast, yeast lysates harboring S308L resulted in a significant reduction in AChE inhibition. Therefore, the results demonstrated the ability of yeast S308L lysates to hydrolyze and thereby detoxify demeton-S methyl.

Example 27

Dementon-S Methyl Hydrolysis Assay

The ability of intact yeast cells to hydrolyze demeton-S methyl and function as a biocatalyst was determined. *S. cer-* evisiae BY4741 harboring integrated copies of the wild-type (OPD) or variant (S308L) OPH genes were grown in YPD media supplemented with 200 µg/mL G418 and 0.1 mM CoCl$_2$ at 30° C. Exponentially growing yeast cells were harvested by centrifugation, washed with 35 mM HEPES pH 8.0, and the specific activity of the yeast cultures against demeton-S methyl was measured using the same assay conditions as for the enzyme lysates (50 mM HEPES pH 7.5, 1.0 mM DTNB, 1 mM demeton-S methyl, 25° C.). The specific activity of yeast cells harboring the wild-type OPH enzyme (OPD) against demeton-S methyl was negligible and similar to control yeast cultures (lacking the OPH enzyme) (Table 24). In contrast, the S308L cells were capable of hydrolyzing demeton-S methyl and functioning as a biocatalyst.

TABLE 24

Activity of *S. cerevisiae* BY4741 whole cells against demeton-S methyl

| OPH | Specific activity[a,b] |
|---|---|
| Wild-type OPD | −0.03 × 10$^{-5}$ (0.024 × 10$^{-5}$) |
| S308L | 2.17 × 10$^{-5}$ (0.37 × 10$^{-5}$) |

[a]µmoles hydrolyzed/min/OD$_{600}$ of 1 (after correction to control cultures)
[b]averages of three independent cultures (standard deviation)

To investigate whether the yeast biocatalyst could also function against OP agents other than demeton-S methy, the ability of intact yeast cells to hydrolyze malathion was determined (Table 25). The specific activity of the S308L yeast cells against malathion was similar to that obtained against demeton-S methyl. Therefore, the results indicated that the yeast biocatalyst may be used against both malathion and demeton-S methyl.

TABLE 25

Activity of *S. cerevisiae* whole cells against malathion

| OPH | Specific activity[a,b] |
|---|---|
| Wild-type OPD | 0.14 × 10$^{-5}$ (0.09 × 10$^{-5}$) |
| S308L | 2.02 × 10$^{-5}$ (0.10 × 10$^{-5}$) |

Figure 25A:
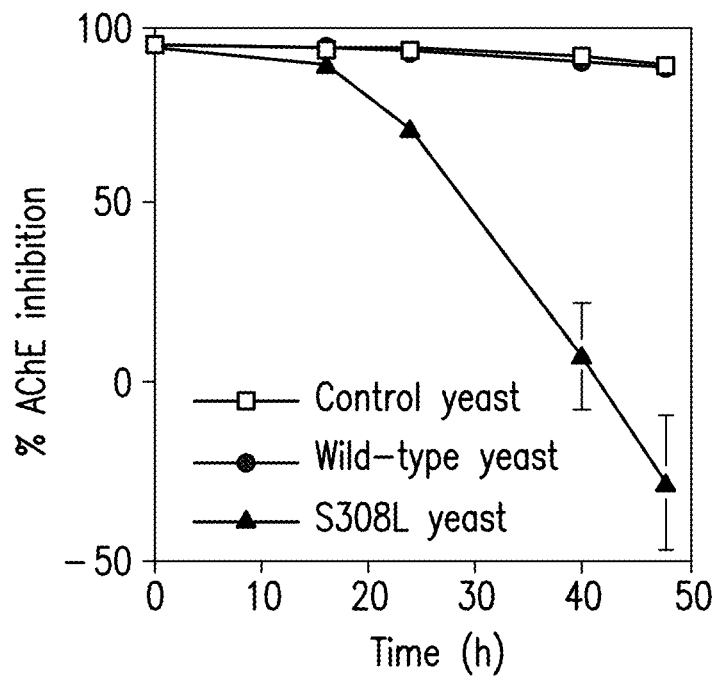
FIG. 25A is a chart illustrating demeton-S methyl detoxification measured by the reduced ability of the OP to inhibit AChE activity using 50 μM demeton-S methyl.
Figure 25B:
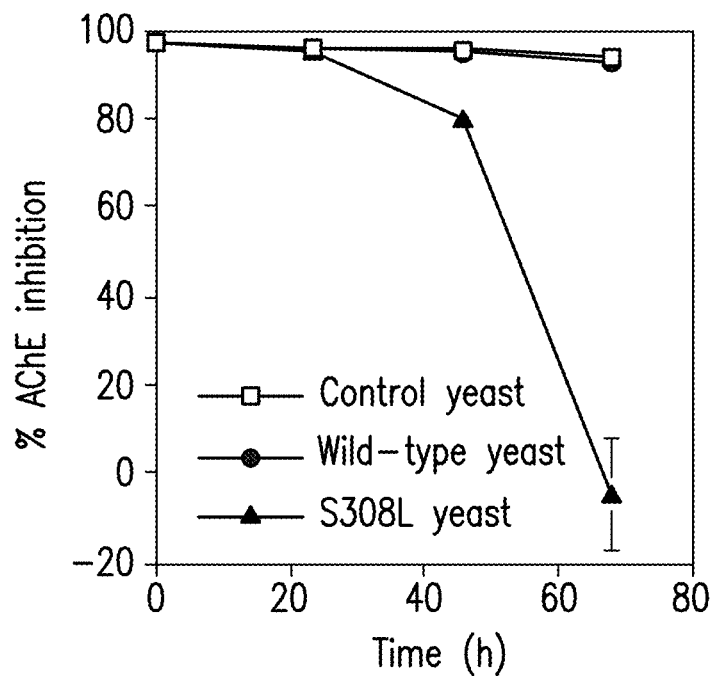
FIG. 25B is a chart illustrating demeton-S methyl detoxification measured by the reduced ability of the OP to inhibit AChE activity using 250 μM demeton-S methyl.

[a]µmoles hydrolyzed/min/OD$_{600}$ of 1 (after correction to control cultures)
[b]averages of three independent cultures (standard deviation)
Reaction mix. 50 mM HEPES pH7.5, 0.1 mM CoCl$_2$, 0.4 mM malathion, 1 mM DTNB To confirm that the S308L yeast biocatalyst hydrolyzed demeton-S methyl and thereby detoxified the OP, samples from the demeton-S methyl hydrolysis assays were analyzed for a reduction in the ability of the OP agent to inhibit AChE. Hydrolysis assays with 50 µM (FIG. 25A) or 250 µM (FIG. 25B) demeton-S methyl were performed with control yeast (no OPH), wild-type yeast (OPH) or S308L yeast. After varying incubation periods at 25° C., the ability of demeton-S methyl to inhibit AChE was measured. The S308L-mediated reduction in AChE activity is directly indicative of the reduced toxicity of the OP agent. Readings represent the mean and SD of three independent cultures. At both demeton-S concentrations, S308L yeast mediated a complete reduction in AChE inhibition. As may be expected, the time required to alleviate AChE inhibition was longer for the assays containing the higher concentration of demeton-S methyl. In contrast, yeast harboring wild-type OPH did not cause a reduction in AChE inhibition over the time period analyzed. Therefore, the results conform the ability of the yeast S308L biocatalyst to hydrolyze and thereby detoxify demeton-S methyl. OPH enzyme detoxifies a wide variety of OP agents by hydrolyzing the various P—O, P—CN, P—F, and P—S containing bonds. The S308L enzyme was generated by screening for improved activity against the P—S class of OPs (such as malathion and demeton-S methyl). To examine whether the improved activity is specific to this class of OP agent (P—S bond), or whether the S308L demonstrates improved activity against other classes of OP agents, the ability of the S308L yeast lysates to hydrolyze paraoxon (P—O bond) was examined. The specific activity of the yeast S308L lysates against paraoxon was 30-fold higher than the control lysates (harboring the wild-type OPH) (Table 26). This suggests that the S308L enzyme demonstrates improved activity against P—S, as well as P—O OP agents compared to the wild-type. It should be noted that differences in the activity of the lysates however, may be due to differences in the catalytic ability of the enzyme, but also due to differences in enzyme stability and solubility.

TABLE 26

Activity of recombinant *S. cerevisiae* lysates against paraoxon

| OPH | Specific activity[a,b] | Fold difference |
|---|---|---|
| Wild-type OPD | 1.42 (0.13) | n/a |
| S308L | 43.61 (3.75) | 30.7 |

[a]µmoles hydrolyzed/min/mg protein (after correction to control lysates)
[b]averages of three independent lysates (standard deviation)
Reaction mix. 50 mM HEPES pH 7.5, 0.1 mM CoCl$_2$, 0.1 mM paraoxon Example 28

VX Hydrolysis Assay

The specific activity of the biocatalyst to hydrolyze VX was determined. The results demonstrated that the yeast biocatalyst was able to hydrolyze VX (Table 27). The specific activity of the biocatalyst against VX was similar, if not greater, than the activity against the demeton-S methyl.

TABLE 27

Activity of *S. cerevisiae* BY4741 S308L whole cells against VX

| Yeast | Specific activity[ab] |
|---|---|
| S308L | $35.7 \times 10^{-5}$ ($5.0 \times 10^{-5}$) |

[a]μmoles hydrolyzed/min/$OD_{600}$ of 1 (after correction to control cultures)
[b]averages of three independent cultures (standard deviation)
Reaction mix. 50 mM HEPES pH7.5, 0.1 mM CoCl2, 0.512 mM VX (in 5% methanol final conc.), 1 mM DTNB. OD415 nm measurements, 37° C., static.

Example 29

Results

The results demonstrated that: (i) recombinant yeast lysates were able to hydrolyze and detoxify the OP agents demeton-S methyl and malathion; (ii) recombinant intact yeast (biocatalyst) were able to hydrolyze and detoxify demeton-S methyl and malathion, and (iii) the recombinant yeast were able to hydrolyze the warfare agent VX.

What is claimed is:

1. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: A80V, I106V, F132D, K185R, D208G, H257W, I274N, S308L, R319S.

2. The isolated organophosphorus hydrolase according to claim 1, wherein the organophosphorus hydrolase has a specific activity of at least about 0.5 µmoles VX hydrolyzed/min/mg protein.

3. The isolated organophosphorus hydrolase according to claim 1, wherein the organophosphorus hydrolase has a specific activity of at least about 1.0 µmole VX hydrolyzed/min/mg protein.

4. The isolated organophosphorus hydrolase according to claim 1, wherein the organophosphorus hydrolase has a specific activity of at least about 1.5 μmoles VX hydrolyzed/min/mg protein.

5. The isolated organophosphorus hydrolase according to claim 1, wherein the organophosphorus hydrolase has a specific activity of at least about 10-fold more than the specific activity of a wild-type organophosphorus hydrolase for the same substrate.

6. The isolated organophosphorus hydrolase according to claim 1, wherein the substrate is selected from the group consisting of malathion and demeton-S methyl.

7. The isolated organophosphorus hydrolase according to claim 1, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

8. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: A80V, K185R, D208G, I274N, R319S.

9. The isolated organophosphorus hydrolase according to claim 8, wherein the organophosphorus hydrolase has a specific activity of at least about 0.5 μmoles VX hydrolyzed/min/mg protein.

10. The isolated organophosphorus hydrolase according to claim 8, wherein the organophosphorus hydrolase has a specific activity of at least about 1.0 μmole VX hydrolyzed/min/mg protein.

11. The isolated organophosphorus hydrolase according to claim 8, wherein the organophosphorus hydrolase has a specific activity of at least about 1.5 μmoles VX hydrolyzed/min/mg protein.

12. The isolated organophosphorus hydrolase according to claim 8, wherein the organophosphorus hydrolase has a specific activity of at least about 10-fold more than the specific activity of a wild-type organophosphorus hydrolase for the same substrate.

13. The isolated organophosphorus hydrolase according to claim 8, wherein the substrate is selected from the group consisting of malathion and demeton-S methyl.

14. The isolated organophosphorus hydrolase according to claim 8, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

15. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: A80V, K185R, D208G, H257W, I274N, R319S.

16. The isolated organophosphorus hydrolase according to claim 15, wherein the organophosphorus hydrolase has a specific activity of at least about 0.5 μmoles VX hydrolyzed/min/mg protein.

17. The isolated organophosphorus hydrolase according to claim 15, wherein the organophosphorus hydrolase has a specific activity of at least about 1.0 μmole VX hydrolyzed/min/mg protein.

18. The isolated organophosphorus hydrolase according to claim 15, wherein the organophosphorus hydrolase has a specific activity of at least about 1.5 μmoles VX hydrolyzed/min/mg protein.

19. The isolated organophosphorus hydrolase according to claim 15, wherein the organophosphorus hydrolase has a specific activity of at least about 10-fold more than the specific activity of a wild-type organophosphorus hydrolase for the same substrate.

20. The isolated organophosphorus hydrolase according to claim 15, wherein the substrate is selected from the group consisting of malathion and demeton-S methyl.

21. The isolated organophosphorus hydrolase according to claim 15, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

22. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: A80V, F132D, K185R, D208G, H257W, I274N, R319S.

23. The isolated organophosphorus hydrolase according to claim 22, wherein the organophosphorus hydrolase has a specific activity of at least about 0.5 μmoles VX hydrolyzed/min/mg protein.

24. The isolated organophosphorus hydrolase according to claim 22, wherein the organophosphorus hydrolase has a specific activity of at least about 1.0 μmole VX hydrolyzed/min/mg protein.

25. The isolated organophosphorus hydrolase according to claim 22, wherein the organophosphorus hydrolase has a specific activity of at least about 1.5 μmoles VX hydrolyzed/min/mg protein.

26. The isolated organophosphorus hydrolase according to claim 22, wherein the organophosphorus hydrolase has a specific activity of at least about 10-fold more than the specific activity of a wild-type organophosphorus hydrolase for the same substrate.

27. The isolated organophosphorus hydrolase according to claim 22, wherein the substrate is selected from the group consisting of malathion and demeton-S methyl.

28. The isolated organophosphorus hydrolase according to claim 22, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

29. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: A80V, F132C, K185R, D208G, H257W, I274N, R319S.

30. The isolated organophosphorus hydrolase according to claim 29, wherein the organophosphorus hydrolase has a specific activity of at least about 0.5 μmoles VX hydrolyzed/min/mg protein.

31. The isolated organophosphorus hydrolase according to claim 29, wherein the organophosphorus hydrolase has a specific activity of at least about 1.0 μmole VX hydrolyzed/min/mg protein.

32. The isolated organophosphorus hydrolase according to claim 29, wherein the organophosphorus hydrolase has a specific activity of at least about 1.5 μmoles VX hydrolyzed/min/mg protein.

33. The isolated organophosphorus hydrolase according to claim 29, wherein the organophosphorus hydrolase has a specific activity of at least about 10-fold more than the specific activity of a wild-type organophosphorus hydrolase for the same substrate.

34. The isolated organophosphorus hydrolase according to claim 29, wherein the substrate is selected from the group consisting of malathion and demeton-S methyl.

35. The isolated organophosphorus hydrolase according to claim 29, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

36. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: A80V, I106V, F132D, K185R, D208G, H257W, I274N, R319S.

37. The isolated organophosphorus hydrolase according to claim 36, wherein the organophosphorus hydrolase has a specific activity of at least about 0.5 μmoles VX hydrolyzed/min/mg protein.

38. The isolated organophosphorus hydrolase according to claim 36, wherein the organophosphorus hydrolase has a specific activity of at least about 1.0 μmole VX hydrolyzed/min/mg protein.

39. The isolated organophosphorus hydrolase according to claim 36, wherein the organophosphorus hydrolase has a specific activity of at least about 1.5 μmoles VX hydrolyzed/min/mg protein.

40. The isolated organophosphorus hydrolase according to claim 36, wherein the organophosphorus hydrolase has a specific activity of at least about 10-fold more than the specific activity of a wild-type organophosphorus hydrolase for the same substrate.

41. The isolated organophosphorus hydrolase according to claim 36, wherein the substrate is selected from the group consisting of malathion and demeton-S methyl.

42. The isolated organophosphorus hydrolase according to claim 36, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

43. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: G60V, A80V, I106V, F132D, K185R, D208G, H257W, I274N, R319S.

44. The isolated organophosphorus hydrolase according to claim 43, wherein the organophosphorus hydrolase has a specific activity of at least about 0.5 μmoles VX hydrolyzed/min/mg protein.

45. The isolated organophosphorus hydrolase according to claim 43, wherein the organophosphorus hydrolase has a specific activity of at least about 1.0 μmole VX hydrolyzed/min/mg protein.

46. The isolated organophosphorus hydrolase according to claim 43, wherein the organophosphorus hydrolase has a specific activity of at least about 1.5 μmoles VX hydrolyzed/min/mg protein.

47. The isolated organophosphorus hydrolase according to claim 43, wherein the organophosphorus hydrolase has a specific activity of at least about 10-fold more than the specific activity of a wild-type organophosphorus hydrolase for the same substrate.

48. The isolated organophosphorus hydrolase according to claim 43, wherein the substrate is selected from the group consisting of malathion and demeton-S methyl.

49. The isolated organophosphorus hydrolase according to claim 43, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

50. An isolated organophosphorus hydrolase comprising a full-length amino acid sequence or a truncated amino acid sequence, truncated at an amino terminus of the sequence, containing the active site of *Flavobacterium* spp. Organophosphate hydrolase and the following set of substitutions as compared to wild type *Flavobacterium* spp. Organophosphate hydrolase: G60V, A80V, I106V, F132D, K185R, D208G, H257W, I274N, F306V, R319S.

51. The isolated organophosphorus hydrolase according to claim 50, wherein the organophosphorus hydrolase has a specific activity of at least about 0.5 μmoles VX hydrolyzed/min/mg protein.

52. The isolated organophosphorus hydrolase according to claim 50, wherein the organophosphorus hydrolase has a specific activity of at least about 1.0 μmole VX hydrolyzed/min/mg protein.

53. The isolated organophosphorus hydrolase according to claim 50, wherein the organophosphorus hydrolase has a specific activity of at least about 1.5 μmoles VX hydrolyzed/min/mg protein.

54. The isolated organophosphorus hydrolase according to claim 50, wherein the organophosphorus hydrolase has a specific activity of at least about 10-fold more than the specific activity of a wild-type organophosphorus hydrolase for the same substrate.

55. The isolated organophosphorus hydrolase according to claim 50, wherein the substrate is selected from the group consisting of malathion and demeton-S methyl.

56. The isolated organophosphorus hydrolase according to claim 50, wherein the substrate is selected from the group consisting of VX, sarin, soman, tabun, paraoxon, diisopropyl fluorophosphate, parathion, methyl parathion, coumaphos, diazinon, fensulfothion, acephate, demeton-S, phosalone, malathion, and combinations thereof.

* * * * *